(12) United States Patent
Shiao et al.

(10) Patent No.: US 10,973,910 B1
(45) Date of Patent: Apr. 13, 2021

(54) NEOGLYCOCONJUGATES AS VACCINES AND THERAPEUTIC TOOLS

(71) Applicant: KORANEX CAPITAL, Montreal (CA)

(72) Inventors: Tze Chieh Shiao, Montreal (CA); Serge Moffett, St-Laurent (CA); Serge Mignani, Chatenay-Malabry (FR); Rene Roy, Terrebonne (CA)

(73) Assignee: Koranex Capital, Montreal (CA)

( * ) Notice: Subject to any disclaimer, the term of this patent is extended or adjusted under 35 U.S.C. 154(b) by 0 days.

(21) Appl. No.: 17/025,978

(22) Filed: Sep. 18, 2020

Related U.S. Application Data

(60) Provisional application No. 62/904,312, filed on Sep. 23, 2019, provisional application No. 63/060,452, filed on Aug. 3, 2020.

(51) Int. Cl.
| | | |
|---|---|---|
| *A61K 47/68* | (2017.01) | |
| *C07F 9/30* | (2006.01) | |
| *C07F 9/32* | (2006.01) | |
| *C07F 9/572* | (2006.01) | |
| *C07F 9/58* | (2006.01) | |
| *A61K 39/215* | (2006.01) | |
| *A61K 39/00* | (2006.01) | |

(52) U.S. Cl.
CPC .... *A61K 39/215* (2013.01); *A61K 2039/6037* (2013.01); *A61K 2039/6056* (2013.01)

(58) Field of Classification Search
CPC .......... A61P 35/00; A61P 37/00; A61P 31/00; A61K 47/6889; C07F 9/301
See application file for complete search history.

(56) References Cited

U.S. PATENT DOCUMENTS

2017/0333568 A1  11/2017  Almeida et al.

FOREIGN PATENT DOCUMENTS

WO         2019178699         9/2019

OTHER PUBLICATIONS

Hoyle and Bowman (2010) "Thiol-Ene Click Chemistry" Agnew. Chem. Int. Ed. 49: 1540-1573.
Kleski et al. (2020) "Enhanced Immune Response Against the Thomsen-Friedenreich Tumor Antigen Using a Bivalent Entirely Carbohydrate Conjugate" Molecules 25: 1319 (14 pages).
Lin et al. (2020) "Site-selective reactions for the synthesis of glycoconjugates in polysaccharide vaccine development" Carbohydrate Polymers 230: 11564 (9 pages).
Schocker et al. (2016) "Synthesis of Galα(1,3)Galβ(1,4)GlcNAcα-, Galβ(1,4)GlcNAcα- and GlcNAc-containing neoglycoproteins and their immunological evaluation in the context of Chagas disease" Glycobiology 26(1): 39-50.
Cipolla et al. (2000) "Stereoselective synthesis of α-C-glycosides of N-acetylgalactosamine" Tetrahedron Asymm., 11: 295-303.
Cui et al. (1998) "Stereocontrolled allylation of 2-amino-2-deoxy sugar derivatives by a free-radical procedure" Carbohydr. Res., 309: 319-330.
Danishefsky et al. (2015) "Development of Globo-H Cancer Vaccine" Acc. Chem Res., 48(3): 643-652.
Demian et al. (2014) "Direct targeted glycation of the free sulfhydryl group of cysteine residue (CYS-34) of BSA. Mapping of the glycation sites of the anti-tumor Thomsen-Friedenreich neoneoglycoconjugate vaccine prepared by Michael addition reaction" J. Mass Spectrom., 49: 1223-1233.
Dondoni et al. (2009) "A new ligation strategy for peptide and protein glycosylation: Photoinduced thiol-ene coupling" Chem. Eur. J., 15: 11444-11449.
Dondoni et al. (2012) "Recent applications in thiol-ene coupling as a click process for glycoconjugation" Chem. Soc. Rev., 41: 573-586.
Feng et al. (2004) "Chemo-enzymatic synthesis of fluorinated 2-N-acetamidosugar nucleotides using UDP-GlcNAc pyrophosphorylase" Org. Biomol. Chem., 2: 1617-1623.
Grant et al. (2020) "Analysis of the SARS-CoV-2 Spike Protein Glycan Shield: Implications for Immune Recognition" bioRxiv., 10: 14991.
Heimburg et al. (2006) "Inhibition of spontaneous breast cancer metastasis by anti-Thomsen-Friedenreich antigen monoclonal antibody JAA-F11" Neoplasia, 8(11): 939-48.
Jeyaprakash et al. (2002) "Crystal structure of the jacalin-T-antigen complex and a comparative study of lectin-T-antigen complexes" J Mol Biol., 321(4): 637-645.
Knapp et al. (2002) "Synthesis of α-GalNAc Thioconjugates from an α-GalNAc Mercaptan" J. Org. Chem., 67: 2995-2999.
Li et al. (2010) "The Thomsen-Friedenreich Antigen-Binding Lectin Jacalin Interacts with Desmoglein-1 and Abrogates the Pathogenicity of Pemphigus Foliaceus Autoantibodies In Vivo" Journal of Investigative Dermatology, 130(12): 2773-2780.

(Continued)

*Primary Examiner* — Barry A Chestnut
(74) *Attorney, Agent, or Firm* — Edward J. Baba; Bozicevic, Field & Francis LLP

(57) ABSTRACT

Neoglycoconjugates as immunogens and therapeutic/diagnostic tools are described herein. The neoglycoconjugates are produced by conjugating a carbohydrate antigen intermediate to a free amine group of a carrier material (e.g., carrier protein). The intermediate comprises a linker having a first end and a second end, the first end being conjugated to a carbohydrate antigen via a thio ether bond and the second end comprising a functional group reactable with a free amine group. Following coupling, the carbohydrate antigen becomes covalently bound to the carrier material via an amide, a carbamate, a sulfonamide, a urea, or a thiourea bond, thereby producing the neoglycoconjugate. Applications of the neoglycoconjugates as antigens, immunogens, vaccines, and in diagnostics are also described. Specifically, the use of (neo)glycoconjugates as vaccine candidates and other therapeutic tools against cancers, viruses such as SARS-CoV-2, and other diseases characterized by expression of aberrant glycosylation are also described.

20 Claims, 37 Drawing Sheets
Specification includes a Sequence Listing.

(56) References Cited

OTHER PUBLICATIONS

Papadopoulous et al. (2012) "Diazo transfer and click chemistry in the solid phase syntheses of lysine-based glycodendrimers as antagonists against *Escherichia coli* FimH" Molecular Pharmaceutics, 9(3): 394-403.

Ress et al. (2005) "Synthesis of Double C-Glycoside Analogue of sTn" Journal of Organic Chemistry, 70(20): 8197-200.

Rittenhouse-Diakun et al. (1998) "Development and characterization of monoclonal antibody to T-antigen: (gal beta1-3GalNAc-alpha-O)" Hybridoma, 17: 165-173.

Roy et al. (2002) "Glycodendrimers: novel glycotope isosteres unmasking sugar coding. Case study with T-antigen markers from breast cancer MUC1 glycoprotein" Reviews in Molecular Biotechnology, 90: 291-309.

Sanda et al. (2002) "N and O glycosylation of the SARS-CoV-2 spike protein", bioRxiv doi: https://doi.org/10.1101/2020.07.05.187344.

Sankaranarayanan et al. (1996) "A novel mode of carbohydrate recognition in jacalin, a Moraceae plant lectin with a β-prism fold" Nat Struct Mol Biol, 3: 596-603.

Shajahan et al. (2020) "Deducing the N- and O-glycosylation profile of the spike protein of novel coronavirus SARS-CoV-2", Glycobiology, 1-8.

Tati et al. (2017) "Humanization of JAA-F11, a Highly Specific Anti-Thomsen-Friedenreich Pancarcinoma Antibody and InVitro Efficacy Analysis" Neoplasia, 19(9): 716-733.

Thompson et al. (2015) "Linear synthesis and immunological properties of a fully synthetic vaccine candidate containing a sialylated MUC1 glycopeptide" Chem. Commun., 51: 10214-10217.

Varki et al. (2015) "Symbol Nomenclature for Graphical Representations of Glycans" Glycobiology, 25(12): 1323-4.

Watanabe et al. (2020) "Site-specific glycan analysis of the SARS-CoV-2 spike" Science, 369(6501): 330-333.

Wu et al. (2019) "Synthesis and Immunological Evaluation of Disaccharide Bearing MUC-1 Glycopeptide Conjugates with Virus-like Particles" ACS Chemical Biology, 14: 2176-2184.

Yang et al. (2011) "Enhancement of the Immunogenicity of Synthetic Carbohydrate Vaccines by Chemical Modifications of STn Antigen" ACS Chem. Biol., 6: 252-259.

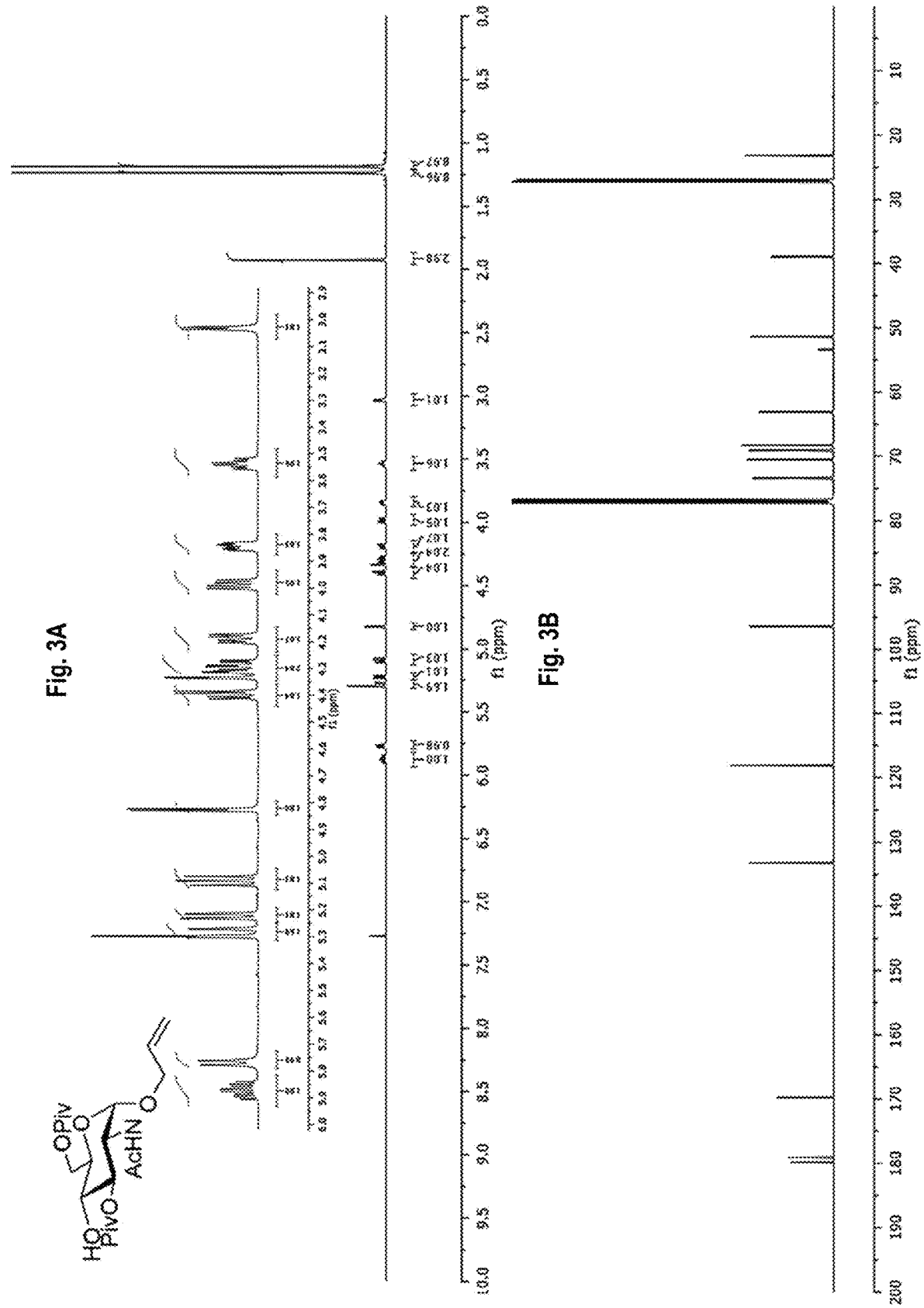

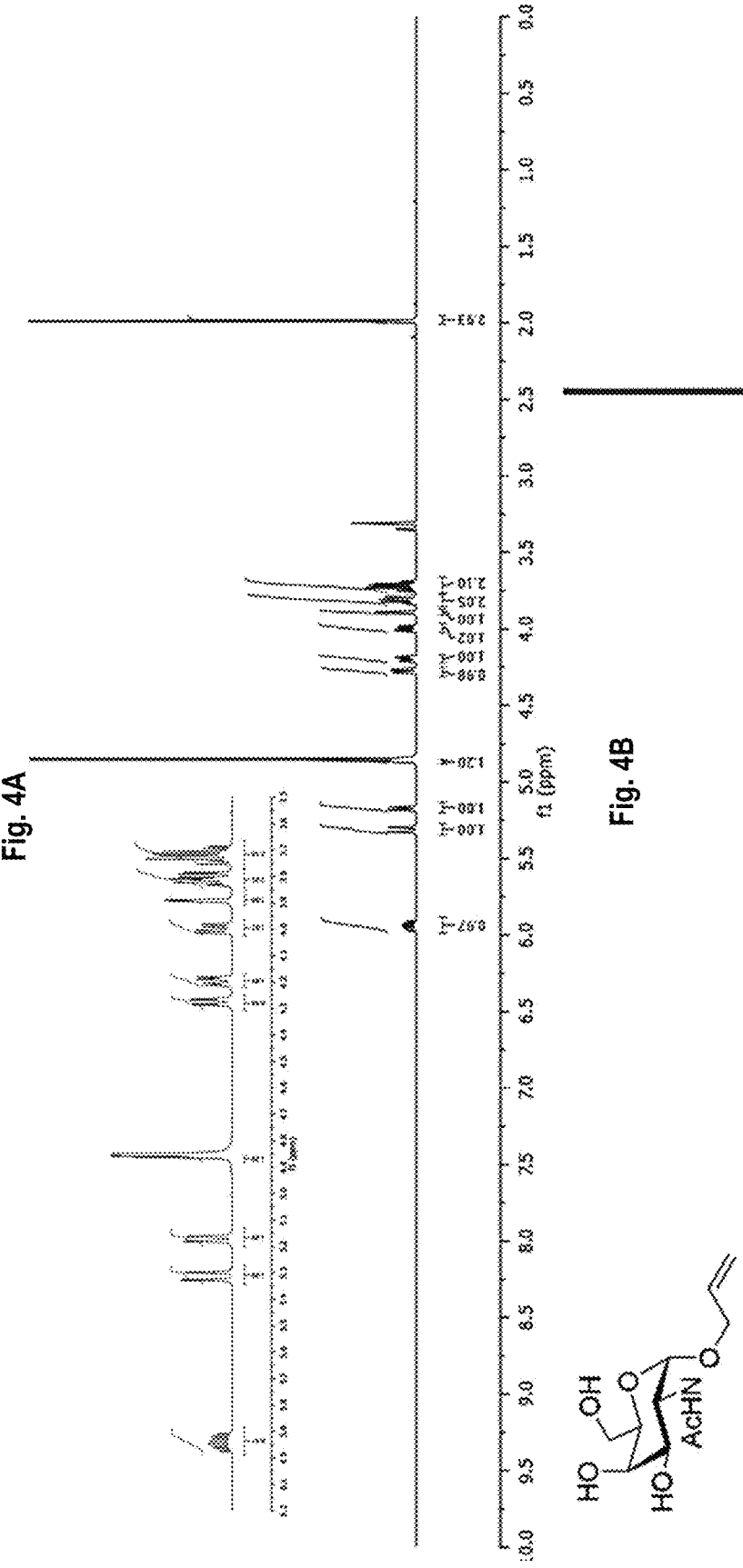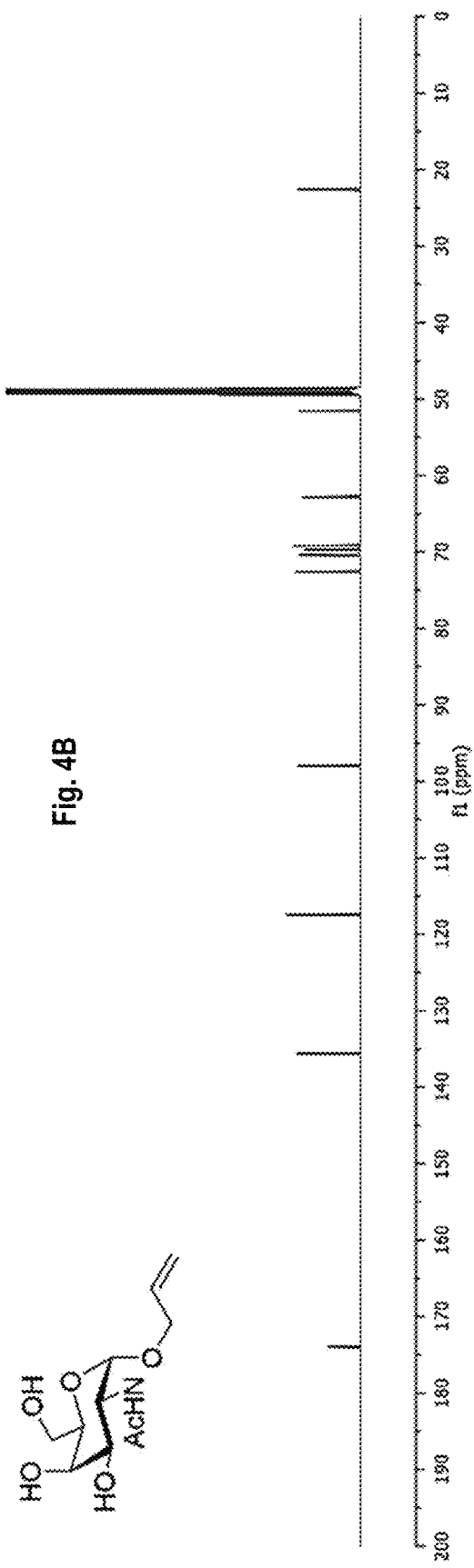
Fig. 4A
Fig. 4B

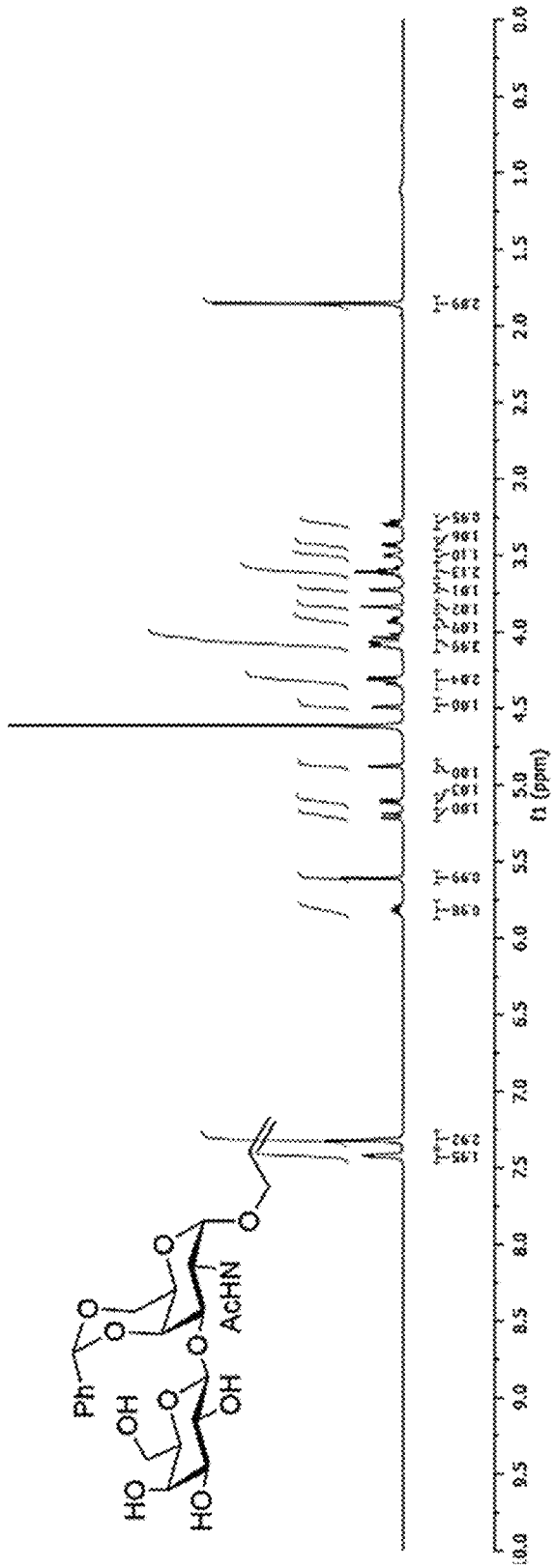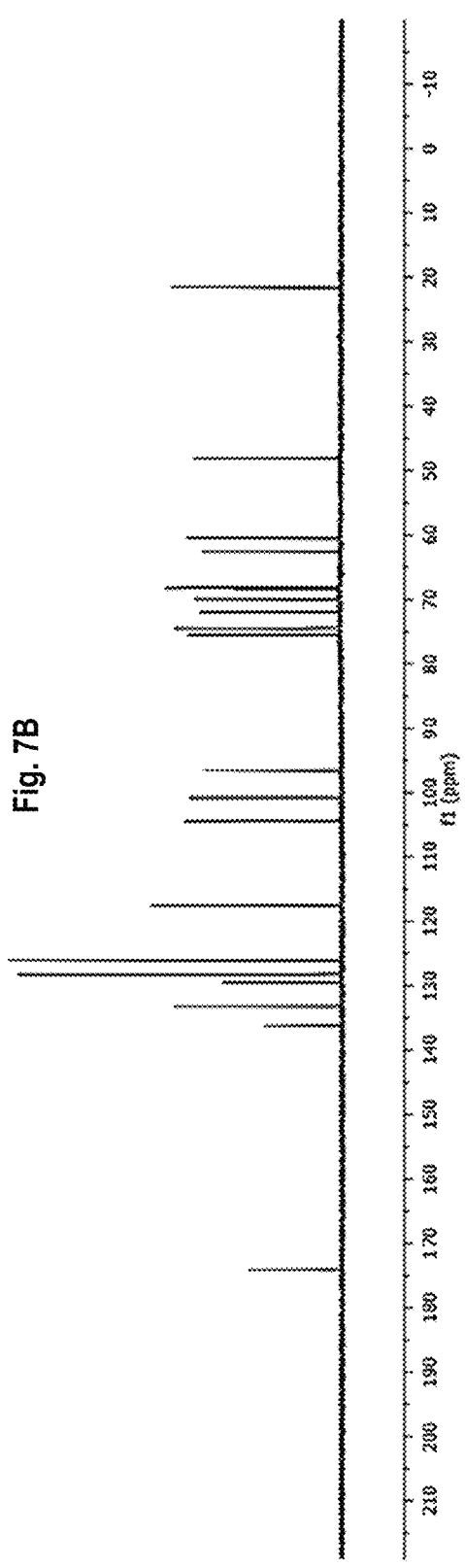
Fig. 7A
Fig. 7B

Fig. 7C

| Compound Table | | | | | | |
|---|---|---|---|---|---|---|
| Compound Label | RT | Mass | Abund | Formula | Tgt Mass | Diff (ppm) |
| Cpd 1: C24 H33 N O11 | 0.1 | 511.205 | 166749 | C24 H33 N O11 | 511.2054 | -0.72 |

| Compound Label | RT | Algorithm | Mass |
|---|---|---|---|
| Cpd 1: C24 H33 N O11 | 0.1 | Find By Formula | 511.205 |

Cpd 1: C24 H33 N O11: +ESI EIC(494.2021, 495.2054, 511.2286...

Counts vs. Acquisition Time (min)

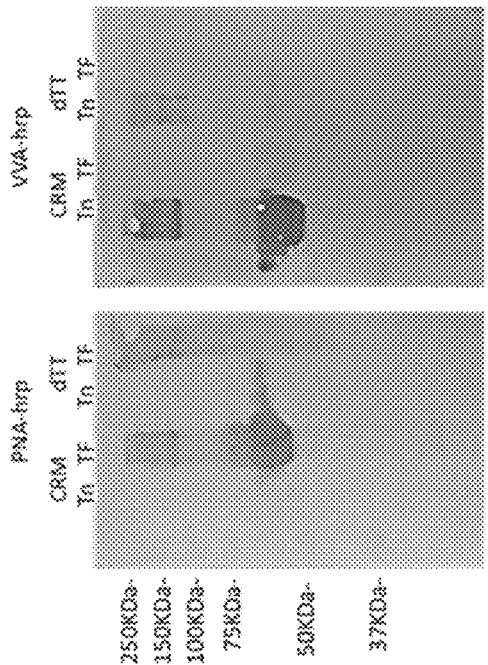
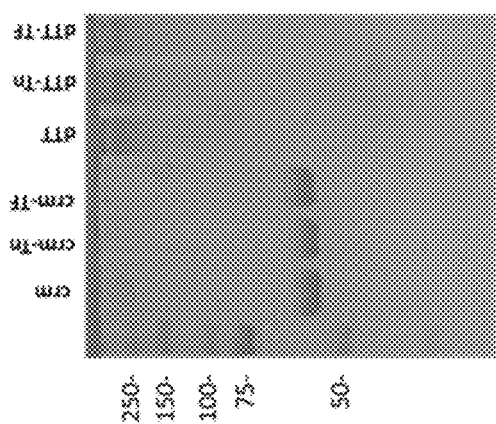
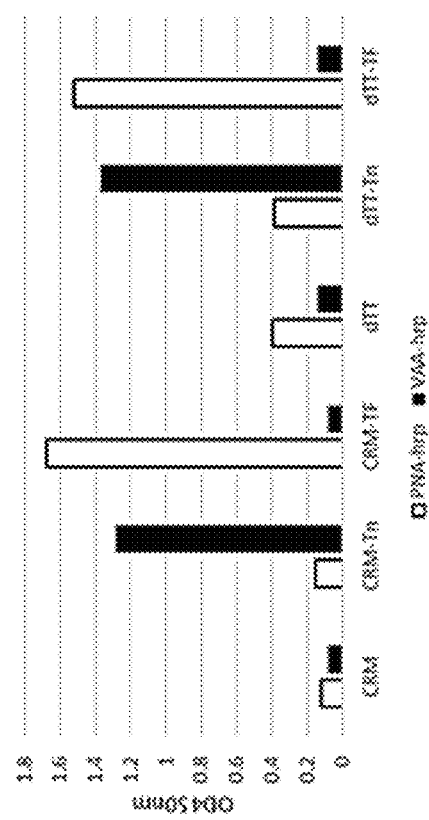

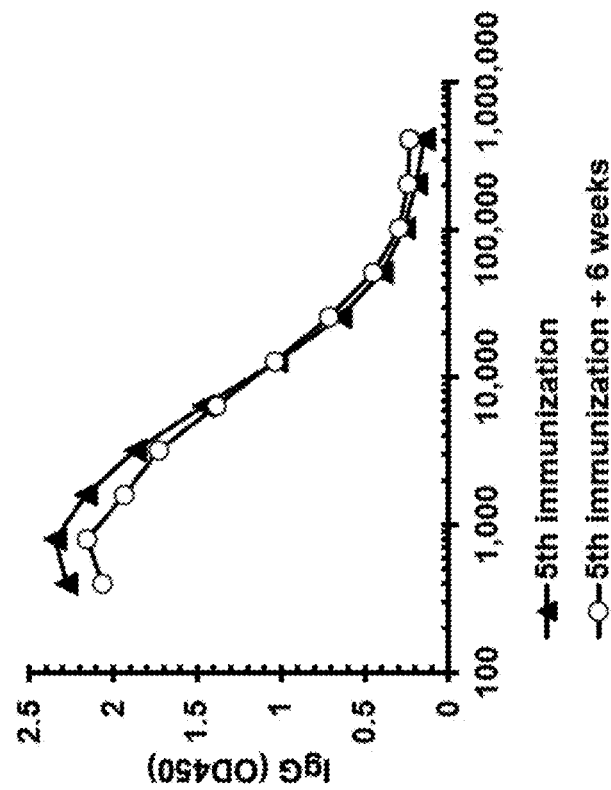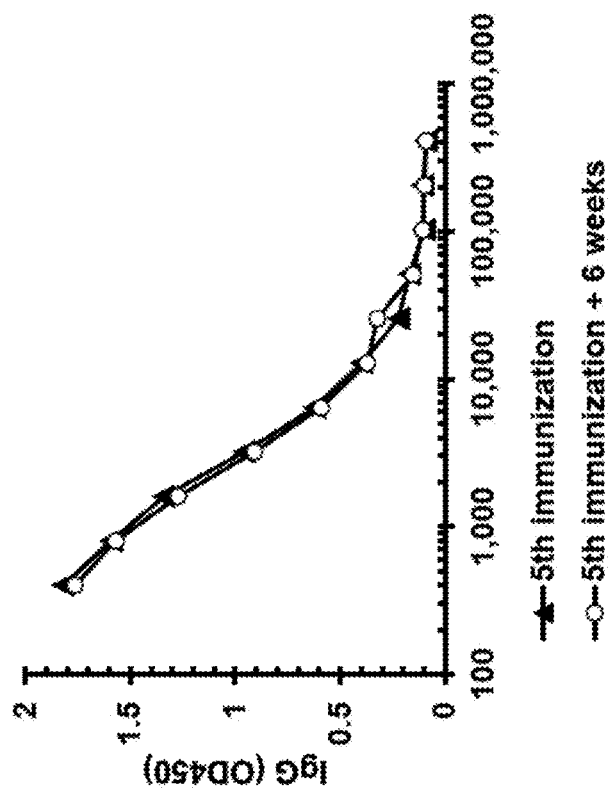

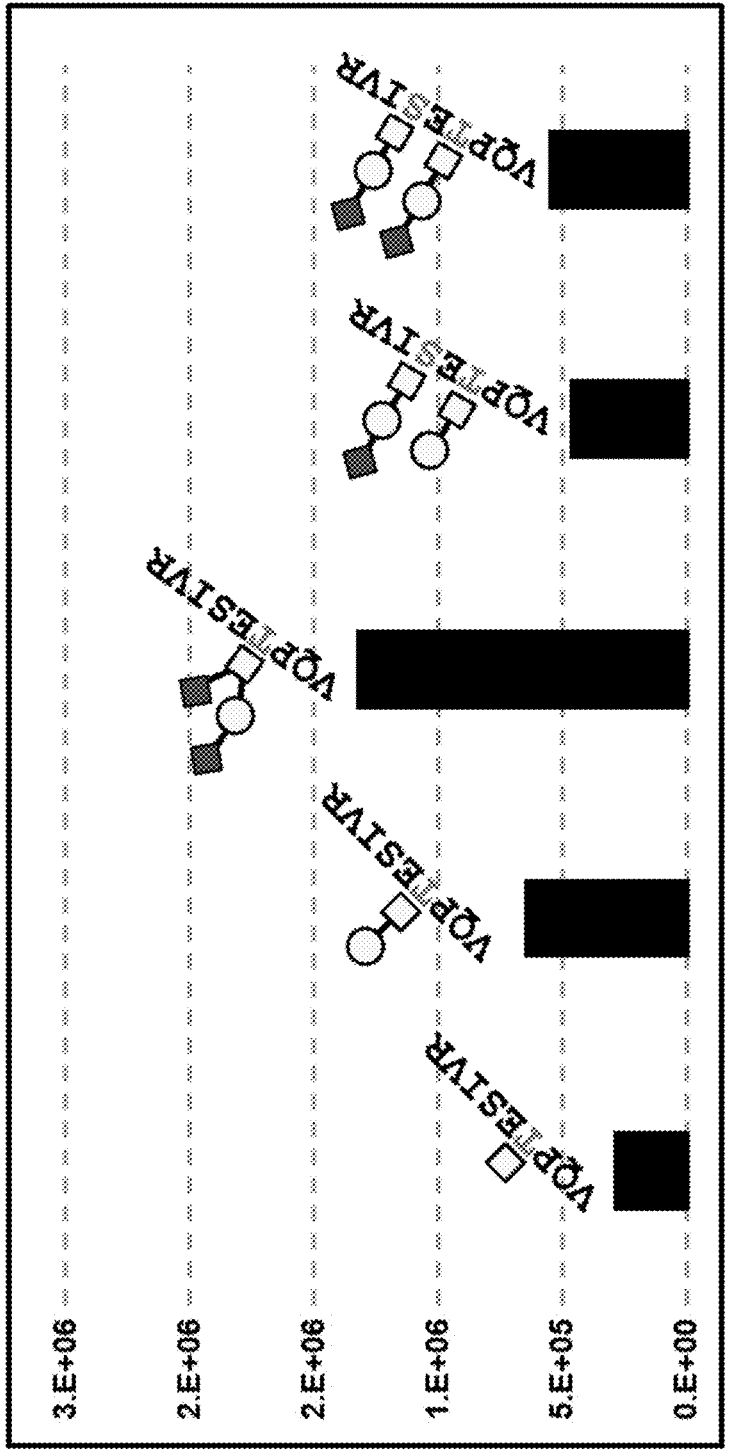

Fig. 23

Reactivity of lectins by ELISA to O-glycans present on SARS-CoV-2 S1 and S proteins expressed in transfected mammalian cells □ S1 fragment  ■ S protein

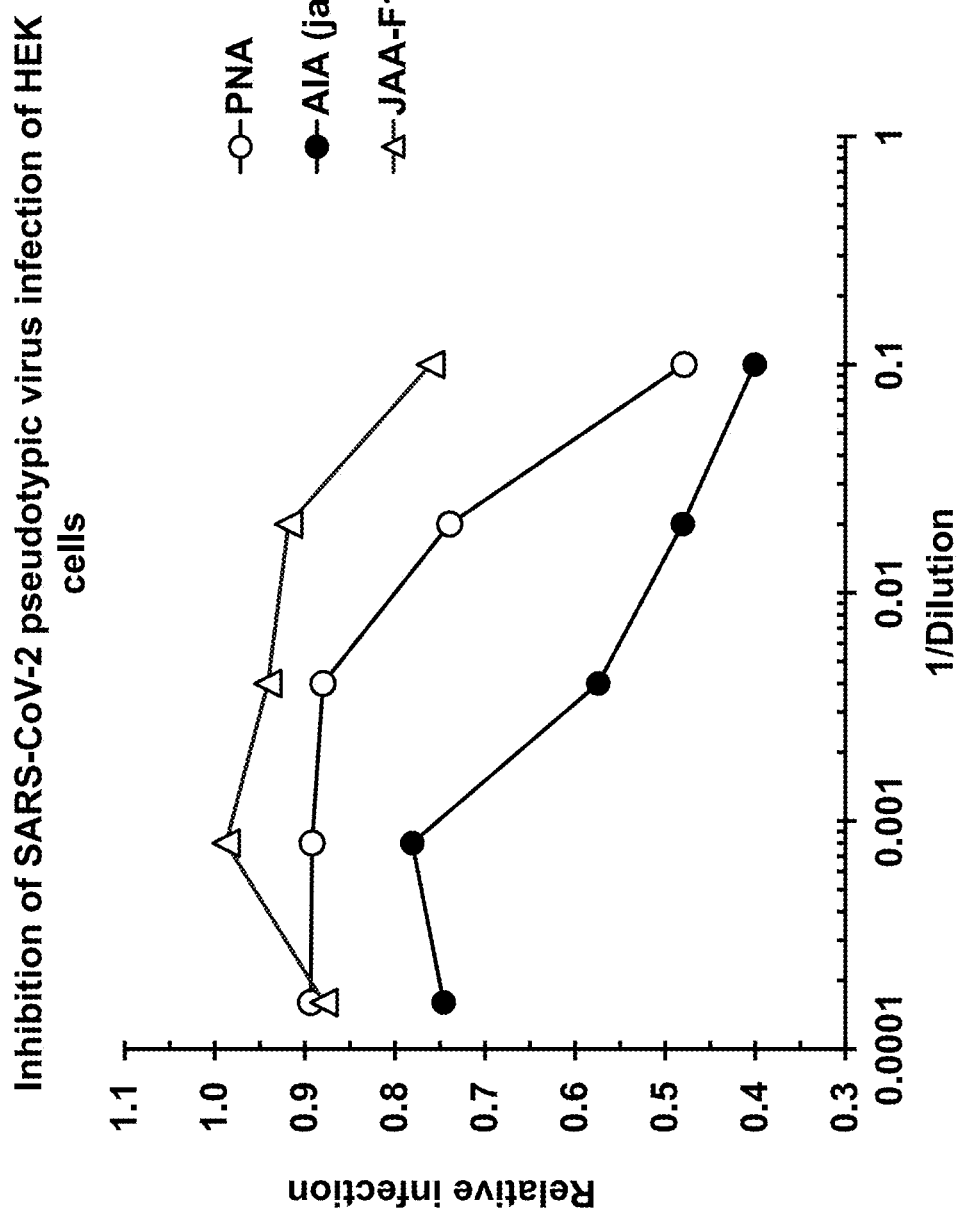

SEQUENCE LISTING

<160> NUMBER OF SEQ ID NOS: 4

<210> SEQ ID NO 1
<211> LENGTH: 14
<212> TYPE: PRT
<213> ORGANISM: Clostridium tetani

<400> SEQUENCE: 1

Tyr Ile Lys Ala Asn Ser Lys Phe Ile Gly Ile Thr Glu Leu
1               5                   10

<210> SEQ ID NO 2
<211> LENGTH: 16
<212> TYPE: PRT
<213> ORGANISM: Artificial Sequence
<220> FEATURE:
<223> OTHER INFORMATION: dTT831-844-Cys-beta-Ala
<220> FEATURE:
<221> NAME/KEY: MOD_RES
<222> LOCATION: (1)..(1)
<223> OTHER INFORMATION: ACETYLATION

<400> SEQUENCE: 2

Tyr Ile Lys Ala Asn Ser Lys Phe Ile Gly Ile Thr Glu Leu Cys Ala
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: O-glycosylated peptide from S1 protein of SARS-
      CoV-2

<400> SEQUENCE: 3

Val Gln Pro Thr Glu Ser Ile Val Arg
1               5

<210> SEQ ID NO 4
<211> LENGTH: 1273
<212> TYPE: PRT
<213> ORGANISM: SARS-CoV-2

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

-continued

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
    195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val

```
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
                660                 665                 670
Ser Tyr Gln Thr Gln Thr Asn Ser Pro Arg Arg Ala Arg Ser Val Ala
                675                 680                 685
Ser Gln Ser Ile Ile Ala Tyr Thr Met Ser Leu Gly Ala Glu Asn Ser
            690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
            755                 760                 765
Gly Ile Ala Val Glu Gln Asp Lys Asn Thr Gln Glu Val Phe Ala Gln
            770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
            835                 840                 845
Leu Ile Cys Ala Gln Lys Phe Asn Gly Leu Thr Val Leu Pro Pro Leu
            850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
            900                 905                 910
Gln Asn Val Leu Tyr Glu Asn Gln Lys Leu Ile Ala Asn Gln Phe Asn
            915                 920                 925
Ser Ala Ile Gly Lys Ile Gln Asp Ser Leu Ser Ser Thr Ala Ser Ala
            930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
                965                 970                 975
Leu Asn Asp Ile Leu Ser Arg Leu Asp Lys Val Glu Ala Glu Val Gln
            980                 985                 990
```

-continued

```
Ile Asp Arg Leu Ile Thr Gly Arg  Leu Gln Ser Leu Gln  Thr Tyr Val
        995              1000              1005

Thr Gln  Gln Leu Ile Arg Ala  Ala Glu Ile Arg Ala  Ser Ala Asn
    1010             1015              1020

Leu Ala  Ala Thr Lys Met Ser  Glu Cys Val Leu Gly  Gln Ser Lys
    1025             1030              1035

Arg Val  Asp Phe Cys Gly Lys  Gly Tyr His Leu Met  Ser Phe Pro
    1040             1045              1050

Gln Ser  Ala Pro His Gly Val  Val Phe Leu His Val  Thr Tyr Val
    1055             1060              1065

Pro Ala  Gln Glu Lys Asn Phe  Thr Thr Ala Pro Ala  Ile Cys His
    1070             1075              1080

Asp Gly  Lys Ala His Phe Pro  Arg Glu Gly Val Phe  Val Ser Asn
    1085             1090              1095

Gly Thr  His Trp Phe Val Thr  Gln Arg Asn Phe Tyr  Glu Pro Gln
    1100             1105              1110

Ile Ile  Thr Thr Asp Asn Thr  Phe Val Ser Gly Asn  Cys Asp Val
    1115             1120              1125

Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Val Val Asn Ile Gln  Lys Glu Ile Asp Arg  Leu Asn Glu
    1175             1180              1185

Val Ala  Lys Asn Leu Asn Glu  Ser Leu Ile Asp Leu  Gln Glu Leu
    1190             1195              1200

Gly Lys  Tyr Glu Gln Tyr Ile  Lys Trp Pro Trp Tyr  Ile Trp Leu
    1205             1210              1215

Gly Phe  Ile Ala Gly Leu Ile  Ala Ile Val Met Val  Thr Ile Met
    1220             1225              1230

Leu Cys  Cys Met Thr Ser Cys  Cys Ser Cys Leu Lys  Gly Cys Cys
    1235             1240              1245

Ser Cys  Gly Ser Cys Cys Lys  Phe Asp Glu Asp Asp  Ser Glu Pro
    1250             1255              1260

Val Leu  Lys Gly Val Lys Leu  His Tyr Thr
    1265             1270
```

NEOGLYCOCONJUGATES AS VACCINES AND THERAPEUTIC TOOLS

CROSS-REFERENCE TO RELATED APPLICATIONS

This application claims the benefit of U.S. Provisional Application Ser. No. 62/904,312, filed on Sep. 23, 2019, and U.S. Provisional Application Ser. No. 63/060,452, filed on Aug. 3, 2020, which applications are incorporated herein by reference in their entirety.

INTRODUCTION

The present description relates to neoglycoconjugates useful as immunogens and as therapeutic/diagnostic tools. More specifically, the present description relates to the conjugation between carbohydrate antigens and free amine groups of a carrier material (e.g., immunogenic and antigenic carrier peptides and proteins). The present description also relates to improved methods of producing the neoglycoconjugates toward applications as antigens, immunogens, vaccines, and in diagnostics. Further, the present description relates to glycoconjugates as vaccine candidates and other therapeutic tools against cancer and viruses, such as SARS-CoV-2, which are associated with aberrant glycosylation.

The present description refers to a plurality of documents, the contents of which are herein incorporated by reference in their entirety.

BACKGROUND

The ultimate objective of immunotherapy is to treat diseases like infections or cancers by modulating the innate and adaptive responses of the immune system to improve its ability to fight foreign substances such as bacteria, viruses, and cancer cells. Innate immunity is considered the first line of immune defense which is triggered in the early phases of exposure to pathogens. The cellular players include natural killer (NK) cells, dendritic cells (DCs), macrophages, monocytes, γδ T-cells and natural killer T (NKT)-cells. Unlike the innate immune system, adaptive immunity is slower to develop upon initial exposure to a foreign antigen but develops a highly specific response and creates immunological memory for a long-lasting protection. It involves the clonal expansion of T cells and B cells and their humoral and cellular mediators, cytokines and antibodies. The principal interfaces between the innate and adaptive immune responses are the professional antigen-presenting cells (pAPCs); macrophages, B cells and particularly dendritic cells (DCs). pAPCs are able to process and present antigens from endogenic and exogenic sources to T cells. They recognize microorganisms through pattern recognition receptors (PRRs) such as Toll-like receptors (TLRs). On recognition of microbial surface determinants or aberrant and unnatural antigens, the microorganisms or tumors and their related antigenic markers can be engulfed by the pAPC through an endocytic pathway where it is typically degraded into peptide fragments and the released antigen is bound onto intracellular MHC class I or class II molecules (pMHC). The pAPCs undergo maturation and activation leading to a redistribution of the pMHC complexes from intracellular compartments to the cell surface, secretion of cytokines and chemokines. In addition to pAPC, all nucleated cells types display only endogenous peptides on the cell membranes. In contrast to pAPC, these peptides originating from within the cell itself, including virus and intracellular pathogens, are displayed by MHC class I molecules coupled to b2-miccroglobulin. APC do not typically express MHC class II.

The peptides displayed on MHC class II molecules are typically recognized by the T cell antigen receptor (TCR) on CD4+ T helper cells which in turn undergo functional maturation into different subsets, such as Th1 or Th2 cells, upon co-stimulatory signals received from the pAPC. Th1 cells lead to a predominantly pro-inflammatory response with the secretion of IFN-γ and TNF-α, whereas Th2 cells secrete typical cytokines. Albeit Th1 cells are mainly associated with a cell-mediated response, both types of Th cells support the production of antibodies by B cells, which in turn influences antibody isotype and function. For example, IL-12 and TNF-α are associated with the differentiation of Th1 cells and production of type 1 IgG subclasses, whereas IL-6 and other Th2 cytokines contribute to the type 2 IgG subclass (IgG1) production.

The APC that display peptides on MHC class I molecules are recognized by the TCR of the CD8+ cytotoxic T cells. Several additional interactions between co-stimulator molecules expressed by the two cell types trigger the activation of the cytotoxic T cells into effector cells, while a strong and long lasting memory T cells is generated when dendritic cells interact with both the activated T-helper and the T-cytotoxic cells. Once activated, the T cell undergoes clonal selection and expansion with the help of the cytokine. This increases the number of cells specific for the dysfunctional target antigen can then travel throughout the body in search of the dysfunctional antigen-positive somatic cells. When docked onto the target cell, the activated cytotoxic T cell release payload of cytotoxins such as perforin and ganzymes. Through the action of perforin, granzymes penetrate the target cells and its proteases trigger the cell death. The cytotoxic T cell can also trigger the target cell death by the FAS signaling pathway. It is thus desirable to be able to tailor vaccine-induced immunity to an appropriate response to deal with a pathogen or tumor antigen of interest.

Carbohydrates, as opposed to proteins and peptides, are T cell independent antigens not properly equipped to trigger the participation of Th cells and hence, cannot induce immune cell proliferation, antibody class switching, and affinity/specificity maturation. The major early advances initially encountered with carbohydrate-based vaccines have been supported by the discovery that, when properly conjugated to carrier proteins, serving as T cell dependent epitopes, bacterial capsular polysaccharides became capable of acquiring the requisite immunochemical ability to produce opsonophagocytic antibodies.

Traditionally, strategies for conjugating carbohydrate antigens to carrier proteins have relied on either reductive amination of aldehyde-derived sugars onto the s-amino groups of the lysine residues, or simply amide coupling reactions. In both cases, partial and random carbohydrate antigen conjugation generally occurs. Furthermore, if all amide partners (amines from lysine or acid from glutamic/ aspartic acids) are used for carbohydrate conjugation, far too many carbohydrate antigens become attached to the carrier proteins, thus resulting in masking potentially essential T cell peptide epitopes with the inherent diminution/elimination of immunogenicity. Thus, current strategies for preparing glycoconjugate vaccines are inadequate and face significant regulatory and/or commercial obstacles, since the preparations lack the necessary homogeneity in terms of their carbohydrate distribution and reproducibility (i.e., the attachment points of the sugars onto the proteins are randomly distributed and in various densities from batch to batch). Thus, glycoconjugate vaccines having greater carbohydrate antigen homogeneity, more precisely characterizable structures, and reproducibility from batch to batch would be highly desirable.

SARS-CoV-2, the causative agent of the COVID-19 pandemic that began in late 2019, represents an ongoing threat to global human health that has also crippled global economies. Initial vaccine development efforts have largely focused on protein antigens and epitopes present on the spike (S) glycoprotein, which mediates cell entry and membrane fusion of SARS-CoV-2 into host cells. However, global health experts have strongly recommended that scientists explore different strategies in parallel for developing therapeutic interventions against SARS-CoV-2 to mitigate against potential failures or complications that may arise for a single strategy. Thus, there remains a need for developing vaccines and other therapeutic tools against SARS-CoV-2 in parallel to those focused on the protein antigens present on the S protein of SARS-CoV-2.

SUMMARY

In a first aspect, described herein is a method for producing a neoglycoconjugate, the method comprising: (a) providing a neocarbohydrate antigen or neocarbohydrate antigen intermediate comprising a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group; (b) providing a carrier material (e.g., carrier protein or peptide) having one or more free amine groups; and (c) performing a coupling reaction to conjugate one or more of the purified neocarbohydrate antigens or neocarbohydrate antigen intermediates to the carrier material (e.g., carrier protein or peptide) at the one or more free amine groups via an amide, a carbamate, a sulfonamide, a urea, or a thiourea bond, thereby producing the neoglycoconjugate.

In some embodiments, prior to step (a), the neocarbohydrate antigen or neocarbohydrate antigen intermediate in (a) is prepared by a method comprising: (i) providing a carbohydrate antigen covalently linked to a terminal alkene (alkenyl carbohydrate antigen), the terminal alkene being directly conjugatable to a thiol group via a thiol-ene reaction; (ii) providing a thio-linker comprising a first functional group at a first end and a second functional group at a second end, the first functional group being a free thiol group and the second functional group being a carboxyl group, sulfinic acid group, carbonic acid group, isocyanate group, or thiocyanate group; (iii) performing a photocatalytic thiol-ene reaction to directly conjugate the alkenyl carbohydrate antigen to the thio-linker at the first end, thereby producing a neocarbohydrate antigen comprising the carbohydrate antigen at the first end and the second functional group at a second end; (iv) when the second functional group is a carboxyl group, sulfinic acid group, or carbonic acid group, converting the neocarbohydrate antigen to a neocarbohydrate antigen intermediate by replacing the carboxyl group's, sulfinic acid group's, or carbonic acid group's terminal hydroxyl group with a better leaving group for conjugation to a free amine group of a polypeptide; and (v) purifying the neocarbohydrate antigen or the neocarbohydrate antigen intermediate.

In a further aspect, described herein is a neocarbohydrate antigen or neocarbohydrate antigen intermediate comprising a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group.

In a further aspect, described herein is a synthetic neoglycoconjugate comprising a linker having a first end and a second end, wherein the first end is conjugated to a carbohydrate antigen via a thio ether bond and the second end is conjugated to a carrier protein or peptide at one or more free amine groups therein via an amide, a carbamate, a sulfonamide, a urea, or a thiourea bond.

In a further aspect, described herein is a synthetic neoglycoconjugate comprising one or more carbohydrate antigens (CA) conjugated to one or more amine groups of a carrier protein or peptide (CP-NH) via a linker, the synthetic neoglycoconjugate having the structure:

$$\left[ \text{CA} - X \underset{m}{\overbrace{\phantom{xxxx}}} S \underset{o}{\overbrace{\phantom{xxxx}}} Y \underset{}{\phantom{x}} Z - \overset{H}{\underset{}{N}} \text{CP} \right]_p$$

wherein: X is O, S, NR$_1$, or CH$_2$; R$_1$ is H, COH (formamide), COMe, or COEt; m is 1, 2, 3, 4, or 5; Y is —(CH$_2$)$_n$— or —(OCH$_2$CH$_2$O)$_n$—; n is 0, 1, 2, 3, 4, or 5; o is 0, 1, 2, 3, 4, or 5; or o is 0 and Z is —CO— and Y is —(OCH$_2$CH$_2$O)$_n$—; or o is 0 and Z is —SO$_2$— and Y is —(OCH$_2$CH$_2$O)$_n$—; Z is —CO—, —NR$_2$SO$_2$—, —OCO—, —NR$_2$CO—, or —NR$_2$CS—, R$_2$ is H, Me, or Et; and p is an integer corresponding to the total number of carbohydrate antigens conjugated to the carrier protein or peptide at said one or more amine groups (e.g., p=1 to 50). In embodiments, the carrier protein or peptide in the synthetic neoglycoconjugate has a native or non-denatured conformation, and conjugation of the carbohydrate antigen to the carrier protein or peptide increases the immunogenicity of the carbohydrate antigen upon administration to the subject as compared to a corresponding administration of the unconjugated carbohydrate antigen.

In a further aspect, described herein is a method for producing a neoglycoconjugate vaccine or an immune response-triggering composition. The method may comprise formulating a neoglycoconjugate as described herein or prepared by a method as described herein with a pharmaceutically acceptable excipient, and/or an adjuvant.

In a further aspect, described herein is a neoglycoconjugate vaccine or an adaptive immune response-triggering composition produced by a method described herein and/or comprising a neoglycoconjugate as described herein and a pharmaceutically acceptable excipient and/or adjuvant as described herein.

In some aspects, described herein is a method of immunizing, vaccinating, or treating a subject comprising administering to the subject a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein.

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for use in immunizing, vaccinating, or treating a subject having a disease, or for detecting the presence of an antibody that specifically binds to the neoglycoconjugate or for detecting said immunization, vaccination, or treatment (e.g., in a biological sample from the subject).

In some embodiments, described herein is a neoglycoconjugate produced by a method as described herein, a synthetic neoglycoconjugate as described herein, or an adaptive immune response-triggering composition produced by a method as described herein, for the manufacture of a vaccine for immunizing or treating a subject having a disease, or for detecting the presence of an antibody that specifically binds to the neoglycoconjugate or for detecting said immunization or treatment (e.g., in a biological sample from the subject).

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for use in the treatment of a subject having a disease associated with increased expression of said carbohydrate antigen.

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for detecting or screening for the presence of an antibody that specifically binds to the carbohydrate antigen or a tumor-circulating cell comprising the carbohydrate antigen, or for detecting the presence of antibodies resulting from an immunization or vaccination with the carbohydrate antigen.

In further aspects, described herein is a method of treating a subject comprising administering a neoglycoconjugate or neoglycoconjugate immunogen as defined herein or produced by a method as described herein, to generate an immune response in said subject to a carbohydrate antigen, and optionally screening a biological sample from said subject for the presence of antibodies that specifically binds to the carbohydrate antigen.

In further aspects, described herein is a glycoconjugate for use in immunizing a subject against SARS-CoV-2, for use in triggering the production of anti-SARS-CoV-2 antibodies in a subject, or for use in detecting the presence of anti-SARS-CoV-2 antibodies in a sample from a subject, the glycoconjugate comprising carbohydrate antigens conjugated to a suitable carrier material (e.g., a carrier protein or peptide), wherein the carbohydrate antigens comprise or consist of sialylated Thomsen-Friedenreich (TF) antigen, unsialylated TF antigen, sialylated Tn antigen, unsialylated Tn antigen, or any combination thereof.

In further aspects, described herein is a SARS-CoV-2 vaccine comprising one or more glycoconjugates as described herein, and a pharmaceutically acceptable excipient and/or an adjuvant.

In further aspects, described herein is a method for vaccinating a subject for SARS-CoV-2 or for triggering the production of anti-SARS-CoV-2 antibodies in a subject, the method comprising administering the glycoconjugates or the SARS-CoV-2 vaccine as described herein.

In further aspects, described herein is a composition for protecting a subject from infection by a SARS-CoV-2 virus, or for treating COVID-19, the composition comprising one or more ligands (e.g., an antibody, antibody fragment, or lectin) that bind to an O-linked glycan expressed on the SARS-CoV-2 S protein, the O-linked glycan comprising sialylated TF antigen (mono- or di-sialylated TF antigen), unsialylated TF antigen, sialylated Tn antigen, unsialylated Tn antigen, or any combination thereof.

In further aspects, described herein is a complex comprising: (a) a SARS-CoV-2 S protein, or fragment thereof, expressing an O-linked glycan comprising sialylated TF antigen (mono- or di-sialylated TF antigen), unsialylated TF antigen, sialylated Tn antigen, unsialylated Tn antigen, or any combination thereof; and (b) a ligand as described herein that is bound to the SARS-CoV-2 S protein, or fragment thereof, at the O-linked glycan.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "protein" (e.g., in the expression "carrier protein") means any peptide-linked chain of amino acids, which may or may not comprise any type of modification (e.g., chemical or post-translational modifications such as acetylation, phosphorylation, glycosylation, sulfation, sumoylation, prenylation, ubiquitination, etc.), so long as the modifications do not destroy the immunogenicity of the neoglycoconjugate immunogens and neoglycoconjugate vaccines described herein. For further clarity, the terms "protein" and "carrier protein" as used herein encompass both peptides and polypeptides, even though both embodiments may be recited together such as in the expression "carrier protein(s) or peptide(s)".

As used herein, the term "neoglycoconjugate" refers to a carbohydrate antigen (e.g., an antigenic monosaccharide, di-saccharide, oligo-saccharide, or polysaccharide, preferably a natural antigen) coupled to a carrier protein or peptide in order to enhance the immunogenicity of carbohydrate antigen in a subject of interest. The expressions "carbohydrate antigen" and "sugar antigen" carry the same meaning as used herein. The term "immunogen" refers to an agent that is capable of being specifically bound by components of the immune system (e.g., by an antibody and/or lymphocytes), and generating a humoral and/or cell-mediated immune response in a subject of interest. As used herein, the term "immunogen" in an expression such as "neoglycoconjugate immunogen" refers to the ability (i.e., physical characteristic or property) of the neoglycoconjugate without limiting the neoglycoconjugate itself to a particular use (e.g., as an immunogen for generating an immune response in a subject). For example, in some embodiments, a neoglycoconjugate immunogen described herein may be employed in diagnostic assays or methods (e.g., in vitro methods) to detect the presence or absence of an antibody that binds to the neoglycoconjugate immunogen in a biological sample (e.g., from a subject). In some embodiments, the neoglycoconjugate immunogens described herein may be used for screening, identifying, or evaluating antibodies that bind specifically to the neoglycoconjugate immunogen (e.g., monoclonal antibodies that are diagnostically or therapeutically applicable).

As use herein, the term "synthetic" refers to a compound that is not a product of nature, which is produced by human intervention.

As used herein, the term "conjugatable" refers to the ability or capability of at least two molecules (e.g., a carbohydrate antigen and a thio-linker; or a neocarbohydrate antigen and a carrier protein or peptide) to be covalently bonded to one another via a chemical reaction, regardless of whether the molecules are actually covalently bonded to one another. In contrast, the term "conjugated" refers to at least two molecules (e.g., a carbohydrate antigen and a thio-linker, or a neocarbohydrate antigen and a carrier protein or peptide) which are covalently bonded to one another.

As used herein, the term "administration" may comprise administration routes such as parenteral (e.g., subcutaneously, intradermally, intramuscularly, or intravenously), oral, transdermal, intranasal, etc., so long as the route of administration results in the generation of an immune response in the subject.

As used herein, the term "subject" generally refers to a living being (e.g., animal or human) that is able to mount an immune response to a neoglycoconjugate as described herein, preferably leading to the production of antibodies and/or lymphocytes that specifically bind to the neoglycoconjugate and/or cells presenting the neoglycoconjugate. In some embodiments, a subject described herein may be a patient to be treated therapeutically (e.g., via vaccination with a neoglycoconjugate immunogen described herein) or may be employed as a means for generating tools (e.g., antibodies) for research, diagnostic, and/or therapeutic purposes.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3A-3D shows the $^1$H-NMR (FIG. 3A) and $^{13}$C-NMR (FIG. 3B) spectra, as well as mass spectrometry results (FIGS. 3C and 3D) for allyl 2-acetamido-3,6-di-O-pivaloyl-2-deoxy-α-D-glucopyranoside (Compound 2).

FIG. 4A-4D shows the $^1$H-NMR (FIG. 4A) and $^{13}$C-NMR (FIG. 4B) spectra, as well as mass spectrometry results (FIGS. 4C and 4D) for allyl 2-acetamido-2-deoxy-α-D-galactopyranoside (allyl Tn).

FIG. 7A-7D shows the $^1$H-NMR (FIG. 7A) and $^{13}$C-NMR (FIG. 7B) spectra, as well as mass spectrometry results (FIGS. 7C and 7D) for Compound 7.

FIG. 15A shows a Western blot showing different BSA-Tn conjugates produced in buffers ranging from pH 6 to 10. A corresponding ELISA analysis is shown in FIG. 15B. FIG. 15C is a Western blot showing the titration of PFP-Tn (compound 9) on conjugation to BSA at the optimal pH of 8. A corresponding ELISA analysis is shown in FIG. 15D. FIG. 15E shows Western blot analysis of CRM197-Tn. The blot revealed a single VVA reactive band in the range of the molecular weight of CRM197 (about 58.4 kDa) for the 3 conjugation ratios of PFP-Tn tested (i.e., 3.4, 9.7, and 15), with the most reactive species of the three generated at the highest PFP-Tn ratio of 15 equivalents.

FIG. 16A shows a Western blot revealed a predominant band reactive to PNA in the range of the expected molecular weight of the BSA monomer indicating the coupling of TF to BSA. A corresponding ELISA analysis is shown in FIG. 16B using PNA-hrp. The conjugation of TF to BSA was also demonstrated by measuring the galactose associated to BSA by the method of Dubois (bar graph in FIG. 16B).

FIG. 17A-17C shows the conjugation of COOH-Tn and COOH-TF to the carrier proteins CRM197 and dTT. FIG. 17A shows a Coomassie stained SDS-PAGE gel, indicating that the conjugated proteins ("-Tn" and "-TF") appear to have slightly increased molecular weight relative to their corresponding unconjugated proteins ("crm" and "dTT"). Corresponding Western blots shown in FIG. 17B show specific reactivity of each -Tn and -TF protein conjugates to the VVA and PNA lectins, respectively. The same pattern of specific reactivity to lectins was also observed by ELISA (FIG. 17C).

FIG. 19A-19B show the reactivity to the screening antigen BSA-TF of a titration of sera from mice immunized five times with dTT-TF, as well as 6 weeks post-5th immunization. FIG. 19A shows results from mouse "A1", and FIG. 19B shows results from mouse "A2".

FIG. 20 shows the relative abundance of all O-glycosylated forms of peptide VQPTESIVR (SEQ ID NO: 3) on recombinant S1 protein of SARS-CoV-2, analyzed by high-resolution LC-MS/MS on proteins over 75 kDA.

FIG. 21 shows the relative abundance of all O-glycosylated forms of peptide VQPTESIVR (SEQ ID NO: 3) on recombinant S1 protein of SARS-CoV-2, analyzed by high-resolution LC-MS/MS on proteins between 75-100 kDA.

FIG. 23 shows the reactivity of a panel of lectins to culture supernatant from mammalian cells transfected with SARS-CoV-2 S1 protein or full length S protein. Results are shown as fold increases over the same monoclonal antibodies exposed to culture supernatant from corresponding mammalian cells transfected with empty vector.

FIG. 24 shows the effect of different anti-carbohydrate ligands to inhibit the infectivity of a pseudotyped lenti-luc-SARS-CoV-2-S virus to host cells expressing human angiotensin-converting enzyme 2. "PNA" and "AIA (jac)" are lectins that have different carbohydrate antigen binding specificities, with the latter being known to have binding specificities for both the TF and Tn antigens in either their sialylated or unsialylated forms. "JAA-F11" is a monoclonal antibody that binds only to the unsialylated form of TF antigen.

SEQUENCE LISTING

Figure 1:
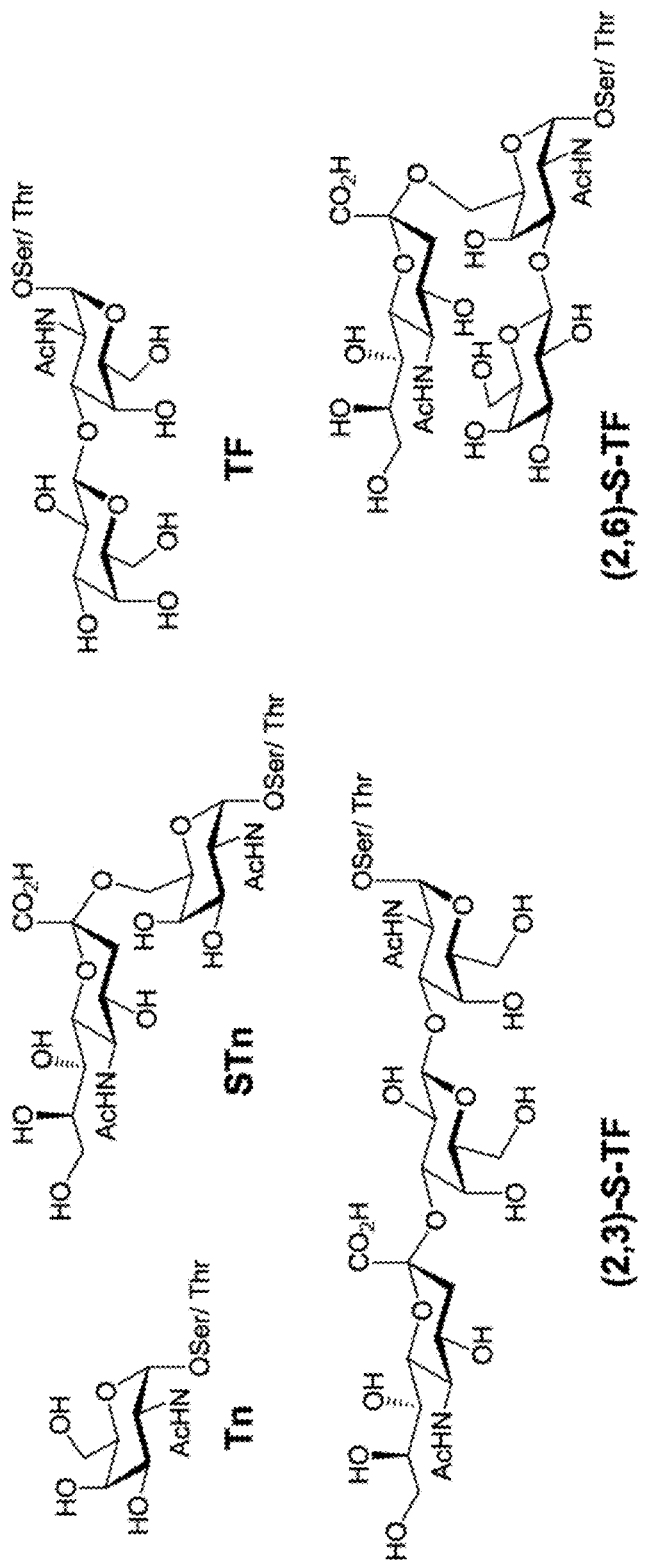
FIG. 1 shows examples of typical chemical structures of key tumor-associated carbohydrate antigens (TACAs), such as from human mucin glycoproteins (MUCs).

This application contains a Sequence Listing in computer readable form created Sep. 17, 2020 having a size of about 12 KB. The computer readable form is incorporated herein by reference.

DETAILED DESCRIPTION

The present description relates to neoglycoconjugates suitable for use such as immunogens, vaccines, in diagnostics, or for generating analytic or therapeutic tools (e.g., generating novel anti-neoglycoconjugate antibodies), as well as improved method for producing same.

Conjugating carbohydrate antigens ending in terminal acid functionalities to amine groups of carrier proteins is traditionally done through random activation with succinimide or carbodiimide reagents. One of the major disadvantages of such carbohydrate antigen-carrier protein conjugation methods is the uncontrolled/undesired self-crosslinking that occurs within the carrier protein itself, wherein the side chains of the carrier protein's own aspartic/glutamic acid residues become coupled to the ε-amine groups of the carrier protein's own lysine residues. This approach leads to perturbation or destruction of the native structure of the carrier protein, often resulting in substantial loss of key peptide sequences that would otherwise be highly immunogenic, as well as potential undesirable cross-linking of the carrier protein. In addition, carbohydrate antigen-carrier protein conjugation methods described in the art often employ linkers such as squaric acids and the like, that may trigger immune responses against the linkers themselves rather than to only the carbohydrate antigens to which they are coupled. Furthermore, carbohydrate antigen-carrier protein conjugation methods described in the art do not allow for adequate control over the extent to which the carrier proteins are glycosylated, often resulting in heterogenous glycoconjugate species, which is a significant barrier to production for human therapeutics.

In contrast, the carbohydrate antigen-carrier protein conjugation strategies described herein differ from those previously described. First, in some embodiments, a carbohydrate antigen possessing an alkenyl functionality is coupled to a non-immunogenic linker by a reagent-free photolytic thiol-ene reaction to produce herein described neocarbohydrate antigens, which upstream step does not affect the structure of the carrier proteins and peptides. Second, in some embodiments, the neocarbohydrate antigens or neocarbohydrate antigen intermediates described herein are made to end with a better leaving group such as an active ester group and are purified prior to conjugation to the carrier proteins or peptides, thus improving conjugation efficacy and at the same time avoiding self-crosslinking within the carrier protein or peptide. Third, the efficacy and stoichiometry of the reacting partners in the carbohydrate antigen-carrier protein conjugation strategies described herein enable more precise control of the number of carbohydrate antigens conjugated to the carrier proteins or peptides, thus avoiding potential masking key immunogenic peptide sequences.

In a first aspect, the present description relates to improved methods for producing neoglycoconjugates. The method generally comprises providing a carbohydrate antigen covalently linked to a terminal alkene (alkenyl carbohydrate antigen), the terminal alkene being directly conjugatable to a thiol group via a thiol-ene reaction. The method further comprises providing a thio-1 inker comprising a first functional group at a first end and a second functional group at a second end, the first functional group being a free thiol group and the second functional group being a group such as a carboxyl group, sulfinic acid group, carbonic acid group, isocyanate group, or thiocyanate group. A photocatalytic thiol-ene reaction is then performed to directly conjugate the alkenyl carbohydrate antigen to the thio-linker at the first end, thereby producing a neocarbohydrate antigen comprising the carbohydrate antigen at the first end and the second functional group at a second end. When the second functional group is a carboxyl group, sulfinic acid group, or carbonic acid group, the methods described herein further comprise converting the neocarbohydrate antigen to a neocarbohydrate antigen intermediate by replacing the carboxyl group's, sulfinic acid group's, or carbonic acid group's terminal hydroxyl group with a better leaving group for conjugation to a free amine group of a polypeptide. The neocarbohydrate antigen or the neocarbohydrate antigen intermediate may then be purified and subsequently employed in a coupling reaction with a carrier material (e.g., carrier protein or peptide) having one or more free amine groups.

The coupling reaction conjugates one or more of the purified neocarbohydrate antigens or neocarbohydrate antigen intermediates to the carrier material at the one or more free amine groups (e.g., via an amide, a carbamate, a sulfonamide, a urea, or a thiourea bond), thereby producing the neoglycoconjugate.

In a further aspect, described herein is a method for producing a neoglycoconjugate, the method comprising: providing a neocarbohydrate antigen or neocarbohydrate antigen intermediate comprising a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group. The method further comprises providing a carrier material (e.g., carrier protein or peptide) having one or more free amine groups; and performing a coupling reaction to conjugate one or more of the purified neocarbohydrate antigens or neocarbohydrate antigen intermediates to the carrier material at the one or more free amine groups via an amide, a carbamate, a sulfonamide, a urea, or a thiourea bond, thereby producing the neoglycoconjugate.

In a further aspect, described herein is a novel neocarbohydrate antigen or neocarbohydrate antigen intermediate. In some embodiments, the neocarbohydrate antigen or neocarbohydrate antigen intermediate comprises a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group.

In a further aspect, described herein is a novel synthetic neoglycoconjugate comprising a linker having a first end and a second end, wherein the first end is conjugated to a carbohydrate antigen via a thio ether bond and the second end is conjugated to a carrier material (e.g., carrier protein or peptide) at one or more free amine groups therein via an amide, a carbamate, a sulfonamide, a urea, or a thiourea bond.

In a further aspect, described herein is a novel synthetic neoglycoconjugate comprising one or more carbohydrate antigens (CA) conjugated to one or more amine groups of a carrier protein or peptide (CP-NH) via a linker, the synthetic neoglycoconjugate having the structure:

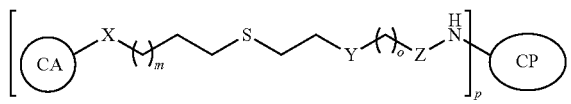

wherein: X is O, S, NR$_1$, or CH$_2$; R$_1$ is H, COH (formamide), COMe, or COEt; m is 1, 2, 3, 4, or 5; Y is —(CH$_2$)$_n$— or —(OCH$_2$CH$_2$O)$_n$—; n is 0, 1, 2, 3, 4, or 5; o is 0, 1, 2, 3, 4, or 5; or o is 0 and Z is —CO— and Y is —(OCH$_2$CH$_2$O)$_n$— or o is 0 and Z is —SO$_2$— and Y is —(OCH$_2$CH$_2$O)$_n$—; Z is —CO—, —NR$_2$SO$_2$—, —OCO—, —NR$_2$CO—, or —NR$_2$CS—; R$_2$ is H, Me, or Et; and p is an integer corresponding to the total number of carbohydrate antigens conjugated to the carrier protein or peptide at said one or more amine groups.

In a further aspect, described herein is a novel synthetic neoglycoconjugate comprising one or more carbohydrate antigens (CA) conjugated to one or more amine groups of a carrier protein or peptide (CP-NH) via a linker, the synthetic neoglycoconjugate having the structure:

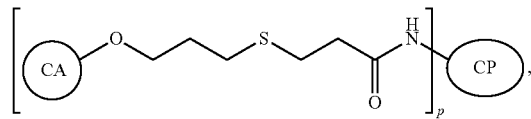

wherein p is an integer corresponding to the total number of carbohydrate antigens conjugated to the carrier protein or peptide at said one or more amine groups.

In some embodiments, p is an integer of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, up to the total number of amine groups available for conjugation on a given carrier protein or peptide (e.g., total number of lysine residues, such as solvent-accessible lysine residues).

In some embodiments, the carrier protein or peptide in the synthetic neoglycoconjugate has a native or non-denatured conformation, and conjugation of the carbohydrate antigen to the carrier protein or peptide increases the immunogenicity of the carbohydrate antigen upon administration to the subject as compared to a corresponding administration of the unconjugated carbohydrate antigen.

In some embodiments, the thiol-ene reactions described herein to directly conjugate the alkenyl carbohydrate antigen to the thio-linker, may be performed under reaction conditions that minimize or avoid destruction or perturbation of the structure and/or antigenicity of the carbohydrate antigen (e.g., potentially leading to undesired immune reactions and/or antibodies being raised against an undesired carbohydrate antigen having the perturbed structure).

In some embodiments, the thiol-ene reactions described herein may be photocatalytic thiol-ene reactions comprising irradiation under ultraviolet light. In some embodiments, the photocatalytic thiol-ene reactions described herein may comprise irradiation under short-wave ultraviolet light (e.g., about 254 nm), or under long-wave ultraviolet light (e.g., at about 355 nm or 365 nm). In some embodiments, the thiol-ene conjugation reactions described herein may posses the versatility to enable conjugations under both short- and long-wave ultraviolet light.

In some embodiments, the thiol-ene reactions described herein may be performed in the presence of a catalyst. For example, in some embodiments, photocatalytic thiol-ene reactions described herein may be performed under long-wave ultraviolet light in the presence of a catalyst, or under short-wave ultraviolet light in the absence of a catalyst, further simplifying the process. As used herein the context of the thiol-ene reactions, the terms "catalyst," "photoinitiator," and "activator" may be used interchangeably to refer to substances that accelerate conjugation of a carbohydrate antigen to a thio-linker at a free thiol group via a photocatalytic thiol-ene reaction. In some embodiments, the catalyst may be a water-soluble catalyst, such as a water-soluble free radical-generating azo compound; 2,2'-azobis[2-(2-imidazolin-2-yl)propane]dihydrochloride (Vazo 44 or VA-044); 2,2'-azobis(2-amidinopropane) dihydrochloride (AAPH); lithium phenyl-2,4,6-trimethylbenzoylphosphinate (LAP); metals or metal ions having photoinitiator activity; a peroxide; tert-butyl hydroperoxide; benzoylperoxide; ammonium persulfate; or any derivative thereof having photoinitiator activity. In some embodiments, the catalyst may be a water-insoluble catalyst, such as a water-insoluble free radical-generating azo compound, 2,2-dimethoxy-2-phenylacetophenone (DMPA), azobisisobutyronitrile (AIBN), 2,2'-azobis(2-methylpropionitrile), 4,4'-Azobis(4- cyanopentanoic acid) (ACVA), 1,1'-azobis (cyanocyclohexane) (ACHN), diazenedicarboxylic acid bis (N,N-dimethylamide) (TMAD); azodicarboxylic acid dipiperidide (ADD), or any derivative thereof having photoinitiator activity.

In some embodiments, the photocatalytic thiol-ene reactions described herein may comprise reacting between 1 to 200 or 1 to 100 molar equivalents of the alkenyl carbohydrate antigen per free thiol group of the thio-linker. In some embodiments, the photocatalytic thiol-ene reactions described herein may be performed for 10 to 300, 10 to 270, 10 to 240, 10 to 210, 10 to 180, 10 to 150, 10 to 120, 10 to 90, 10 to 60, or 10 to 30 minutes.

In some embodiments, the photocatalytic thiol-ene reactions described herein may be performed at a pH between about 3.0, 3.1, 3.2, 3.3, 3.4, 3.5, 3.6, 3.7, 3.8, 3.9, or 4.0, and about 4.5, 4.6, 4.7, 4.8, 4.9, 5.0, 5.5, 6.0, 6.5, 7.0, 7.5, 8.0, 8.5, 9.0, 9.5, or 10. In some embodiments, the photocatalytic thiol-ene reactions described herein may be performed at a pH that minimizes or avoids carbohydrate antigen perturbation or destruction.

In some embodiments, the carbohydrate antigens described herein may be chemically modified to be linked (directly or indirectly via a linker or spacer) to a terminal alkene (e.g., via a glycosidic bond or a bond obtained by reductive amination, such as between an allyl or alkenyl amine and a reducing sugar, preferably using $NaBH_4$ and/or $NaBH_3CN$), wherein the terminal alkene group of the alkenyl carbohydrate antigen is conjugatable to a free thio-linker via a thiol-ene reaction (e.g., a photocatalytic thiol-ene reaction). The terminal alkene group of the alkenyl carbohydrate antigen may be a monosubstituted alkene, a vinyl group, or an allyl group.

In some embodiments, the carbohydrate antigens described herein may be covalently linked to the terminal alkene via a glycosidic bond, such as is an O-glycosidic bond, an S-glycosidic bond, an N-glycosidic bond, or a C-glycosidic bond, or a bond obtained by reductive amination, such as between an allyl amine and a reducing sugar (including bacterial CPS). As used herein, the "glycosidic bond" may comprise one or more of an S-glycosidic bond, an N-glycosidic bond, an O-glycosidic bond, or a C-glycosidic bond, or a bond obtained by reductive amination of a reducing sugar (e.g., using $NaBH_4$ or preferably $NaBH_3CN$). In some embodiments, the glycosidic bond may be one that is not cleavable by an endogenous enzyme (e.g., a glycohydrolase) of the subject to be administered. Such an uncleavable glycosidic bond may result in a neoglycoconjugate immunogen having a longer half-life following administration to the subject, which may in turn generate a more favorable immune response for therapeutic and/or antibody-generation purposes. In some embodiments, the glycosidic bond may be an S-glycosidic bond, an N-glycosidic bond, or a C-glycosidic bond, or a bond obtained by reductive amination, such as between an allyl amine and a reducing sugar.

In some embodiments, the thio-linkers described herein may comprise the structure:

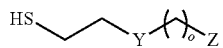

wherein: Y is —$(CH_2)_n$— or —$(OCH_2CH_2O)_n$—; Z is —$CO_2H$, —$SO_2H$, —O—C(O)—H, —N=C=O, or —N=C=S; O is 0, 1, 2, 3, 4, or 5; O is 0 and Z is —CO— and Y is —$(OCH_2CH_2O)_n$—; or O is 0 and Z is —$SO_2$— and Y is —$(OCH_2CH_2O)_n$—.

In some embodiments, the methods and neoglycoconjugates described herein preferably employ unprotected carbohydrate antigens, which improve the aqueous solubility of the carbohydrate antigens themselves as well as avoid the step of later removing the carbohydrate antigen protecting groups. Thus, in some embodiments, the carbohydrate portions of the carbohydrate antigens, the alkenyl carbohydrate antigens, the neocarbohydrate antigens, the neocarbohydrate antigen intermediates, and/or the neoglycoconjugates remain unprotected throughout the methods described herein.

In some embodiments, when the second functional group of neocarbohydrate antigens described herein is group such as a carboxyl group, sulfinic acid group, or carbonic acid group, the methods described herein may further comprise converting the neocarbohydrate antigen to a neocarbohydrate antigen intermediate by replacing the carboxyl group's, sulfinic acid group's, or carbonic acid group's terminal hydroxyl group with a better leaving group for conjugation to a free amine group of a polypeptide. The expression "better leaving group" as used herein refers to a leaving group that provides improved reaction efficiency and/or specificity (i.e., improved conjugation to a free amine group of a polypeptide) as compared to the corresponding functional group prior to replacement with the leaving group. In some embodiments, the leaving groups employed herein may be an active ester group (e.g., a fluorophenyl group (e.g., OPhF5, OPhF4 (para $SO_3Na$)), or a succinimidyl group). The neocarbohydrate antigen intermediate may then be purified and subsequently employed in a coupling reaction with a carrier protein or peptide having one or more free amine groups. The coupling reaction conjugates one or more of the purified neocarbohydrate antigen intermediates to the carrier protein or peptide at the one or more free amine groups (e.g., via an amide, a carbamate, a sulfonamide, a urea, or a thiourea bond), thereby producing neoglycoconjugates described herein.

In some embodiments, the neocarbohydrate antigen-carrier protein coupling reactions described herein may advantageously minimize or avoid carrier protein or peptide self-crosslinks between the side chains of aspartate/glutamate residues and ε-lysine amines present in the carrier protein or peptide itself.

In some embodiments, the neocarbohydrate antigen-carrier protein coupling reactions described herein enable the number of neocarbohydrate antigens conjugated to the carrier protein or peptide to be controlled by the efficacy and/or stoichiometry of the reactants (e.g., the molar ratio of the carrier protein or peptide to the neocarbohydrate antigen or the neocarbohydrate antigen intermediate). In some embodiments, the neocarbohydrate antigen-carrier protein coupling reactions described herein may comprise reacting between 1 to 500, 1 to 400, 1 to 300, 1 to 200, 5 to 500, 5 to 400, 5 to 300, or 5 to 200 molar equivalents of the neocarbohydrate antigen or neocarbohydrate antigen intermediate per carrier protein or peptide. In some embodiments, the present description relates to a composition comprising neoglycoconjugate immunogens having about or at least 70%, 75%, 80%, 85%, 90%, or 95% homogeneity in terms of carbohydrate conjugation species (e.g., at least 90% of neoglycoconjugates species/molecules in the composition have the same number of carbohydrate antigens conjugated to the carrier protein).

In some embodiments, the (neo)carbohydrate antigens described herein may comprise a B cell epitope, and/or induces a humoral immune response in the subject. In some embodiments, the (neo)carbohydrate antigens described herein may comprise a T cell epitope, and/or induces a cell-mediated immune response in the subject. In some embodiments, the (neo)carbohydrate antigens described herein may comprises both a B cell epitope and a T cell epitope, and/or induces both a humoral and a cell-mediated immune response in the subject. In some embodiments, the carbohydrate antigens described herein may be or comprise a tumor associated carbohydrate antigen (TACA), such as Tn, S-Tn, Thomsen-Friedenreich (TF), (2,3)-S-TF, (2,6)-S-TF (FIG. 1), Globo H, PSA, GD2, GD3, GM2, GM3, N-glycolyl-GM3, Fucosyl GM1, Le$^a$, sLe$^a$, Le$^x$, sLe$^x$, Le$^y$, or any combination thereof. In some embodiments, the carbohydrate antigens described herein may comprise a viral polysaccharide antigen, or a bacterial capsular polysaccharide (CPS) (e.g., a Pneumococcal and/or Streptococcal polysaccharide serotype, meningococcal CPS; influenza (such as influenza type a or b) CPS).

In some embodiments, the neocarbohydrate antigen-carrier protein coupling reactions described herein may conjugate at least two of the same carbohydrate antigens, or more than one type of carbohydrate antigen, to the carrier protein or peptide via one or more types of thio-linkers, thereby producing a multi-valent neoglycoconjugates. In some embodiments, the multi-valent neoglycoconjugate may comprise 2, 3, 4, 5, 6, 7, 8, 9, 10, 11, 12, 13, 14, 15, or more of the same or different types of carbohydrate antigens conjugated to the carrier protein or peptide. In some embodiments, neoglycoconjugate immunogens described herein may comprise any combination of TACAs selected from Tn, S-Tn, Thomsen-Friedenreich (TF), (2,3)-S-TF, (2,6)-S-TF, Globo H, PSA, GD2, GD3, GM2, GM3, N-glycolyl-GM3, Fucosyl GM1, Le$^a$, sLe$^a$, Le$^x$, sLe$^x$, and Le$^y$. In some embodiments, sialylated or unsialylated Tn and TF antigens (and analogs thereof) may be synthesized as described herein or as described in for example Ress et al., 2005; Wu et al., 2019; Thompson et al., 2015; and Yang et al., 2010. In some embodiments, ratio in the combination of each TACAs may vary with the targeted tumor and may comprise between 1 to 20 molar ratios. In this way, the neoglycoconjugate immunogens described herein may be tailored, for example, to specific forms of cancer that are associated with increased expression of particular combinations of multiple TACAs, such as described in the table below free amine group on the carrier protein (e.g., via branched linker). In some embodiments, the multi-valent neoglycoconjugate immunogens described herein may comprise a plurality (e.g., at least 3, 4, 5, 6, 7 8, 9, 10, 11, 12, 13, 14, 15, or more) of (neo)carbohydrate antigens that are conjugated to a thio-1 inker prior to attachment onto the carrier protein or peptide as a dendrimer (e.g., via linkers having extensive branching).

In some embodiments, the carrier proteins or peptides described herein comprise one or more free amine groups. As used herein, "free amine" or "free amine group" refers to carrier proteins or peptides having one or more amino groups that are available for chemical modification and/or conjugation (e.g., to a carbohydrate antigen as described herein, such as solvent accessible lysine residues that tend to be exposed on the periphery of the carrier protein). In some embodiments, it may be advantageous to avoid having too many multiple (neo)carbohydrate antigens conjugated to adjacent positions on the carrier proteins. In some embodiments, the carrier protein or peptide may preferably lack a lysine-rich domain (e.g., a segment of at least 4, 5, 6, 7, 8, 9, or 10 consecutive amino acids comprising at least 50% of lysine residues).

In some embodiments, the carrier protein may comprise at least 1, 2, 3, 4, 5, 6, 7, 8, 9, 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 total lysine residues. In some embodiments, the carrier protein may comprise 1, 2, 3, 4, 5, 6, 7, 8, 9, 10, 11, 12, 13, 14, 15, 16, 17 18, 19, 20, 21, 22, 23, 24, 25, 26, 27, 28, 29, or 30 total free amine residues.

In some embodiments, the carrier protein or peptide comprises one or more lysine residues having the one or more free amine groups, or optionally is engineered to add one or more further lysine residues, for example at the amino terminus, the carboxy terminus, or a solvent-accessible position of the carrier protein or peptide. In some embodiments, the carrier protein comprises a T cell epitope, and/or induces a cell-mediated immune response in the subject. In some embodiments, the carrier protein or peptide comprises a B cell epitope, and/or induces a humoral immune response in the subject. In some embodiments, the carrier protein

| | B-cell lymphoma | Breast | Colon | Lung | Melanoma | Neuro-blastoma | Ovary | Prostate | Sarcoma | Small cell lung | Stomach |
|---|---|---|---|---|---|---|---|---|---|---|---|
| sLe$^x$ | | | | + | | | | | | | |
| Le$^x$ | | | | | | | | | | | + |
| sLe$^a$ | | + | + | | | | | | | + | + |
| Le$^a$ | | | | | | | | | | | + |
| sTn | | + | + | + | | | + | + | | | + |
| Tn | | + | | | | | + | | | | + |
| TF | | + | + | | | | + | + | | | + |
| Le$^y$ | | + | + | + | | | + | + | | | + |
| Globo H | | + | | + | | | + | | | + | + |
| PSA | | | | | + | | | | | + | + |
| GD2 | + | | | | + | + | | | + | | |
| GD3 | | | | | + | + | | | + | | |
| GM2 | + | + | + | + | + | + | + | + | + | + | + |
| Fucosyl GM1 | | | | | | | | | | + | |

Distribution of Tumor Associated Carbohydrate Antigens (TACAs) on different cancers In some embodiments, the multi-valent neoglycoconjugate immunogens described herein may comprise more than one (neo)carbohydrate antigen that is conjugated to a single comprises both a B cell epitope and a T cell epitope, and/or induces both a humoral and a cell-mediated immune response in the subject.

Preferably, the carrier protein described herein may be a protein that has already received regulatory (e.g., FDA) approval for administration to human subjects (e.g., in approved vaccines). In some embodiments, the carrier protein is, is from, or comprises: Tetanus Toxoid (TT), Diphtheria Toxoid (DT), cross-reacting material 197 (CRM197), Meningococcal Outer Membrane Protein Complex (OMPC), *H. Influenzae* Protein D (HiD), a virus-like particle (VLP), a cytokine, an immunogenic peptide such as Tetanus Toxin 831-844 (SEQ ID NO: 1 or 2), albumin (such as bovine serum albumin or human serum albumin), keyhole limpet hemocyanin (KLH), or an immunogenic fragment thereof.

In some embodiments, the carrier protein or peptide is exogenous to the subject to be administered, which preferably has no (close) ortholog in the subject. In the context of human vaccine production, a carrier protein described herein refers to a "carrier protein suitable for human use" or simply "suitable carrier protein", which means a carrier protein that is antigenically distinct from human proteins such that the carrier protein would not be considered as a "self-antigen" in humans. The use of carrier proteins that are too antigenically similar to corresponding human proteins may result in the carrier protein being considered as a "self-antigen", which may not be ideal in human vaccines. For example, neoglycoconjugate immunogens consisting of TF antigen randomly conjugated to the s-amino groups of lysine residues of bovine serum albumin (BSA) have been previously described and characterized (e.g., Demian et al., 2014; Rittenhouse-Diakun et al., 1998; Fieimburg et al., 2006; Tati et al., 2017). However, not only was the level of carbohydrate on the 59 lysine residues of BSA random and inefficient (no more than 4 to 6 TF antigens were conjugated per BSA molecule), BSA would not be suitable as a carrier protein in human vaccines because it is too antigenically similar to human albumin. In some embodiments, the carrier protein is not albumin (e.g., bovine serum albumin).

In some embodiments, the neoglycoconjugates described herein may be neoglycoconjugate immunogens, wherein the carrier protein or peptide is immunogenic when administered to a subject, and conjugation of the carbohydrate antigen to the carrier protein or peptide via the thio-1 inker increases the immunogenicity of the carbohydrate antigen upon administration to the subject as compared to a corresponding administration of the unconjugated carbohydrate antigen.

In some embodiments, the thio-linkers described herein are non-immunogenic to the subject to be administered the neoglycoconjugates, such that administration of the neoglycoconjugate immunogen to the subject does not trigger antibodies against the thio-1 inker comprised in the neoglycoconjugate immunogen. In some embodiments, the thiolinkers described herein lack synthetic chemical/functional groups (i.e., chemical/functional groups that are not found naturally in the subject). In some embodiments, the thiolinkers described herein comprise only natural chemical/functional groups, i.e., functional groups that are found natively in the subject. In this regard, some carbohydrate antigen-protein linkers employed in the art such as squaric acids and the like, that may trigger immune responses against the linkers themselves rather than to only the carbohydrate antigens to which they are coupled, likely related to the "foreign" and/or antigenic nature of their chemical/functional groups.

In some embodiments, the carbohydrate antigen or neocarbohydrate antigen, following coupling to the carrier protein or peptide, is not cleavable from the carrier protein or peptide by an endogenous enzyme of the subject.

In some embodiments, the carrier proteins or peptides described herein may comprise a T cell epitope, and/or induce a cell-mediated immune response in the subject upon administration.

In some embodiments, the synthetic neoglycoconjugate immunogens described herein may induce a cell-mediated immune response to the (neo)carbohydrate antigen upon administration to the subject.

In a further aspect, described herein is a method for producing a neoglycoconjugate vaccine or an immune response-triggering composition. The method may comprise formulating a neoglycoconjugate as described herein or prepared by a method as described herein with a pharmaceutically acceptable excipient, and/or an adjuvant. In some embodiments, the adjuvant is or comprises: an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide (e.g., CPG), an immunostimulatory lipid, Freund's adjuvant, RIBI's adjuvant, QS-21, muramyl dipeptide, TiterMax™, Steviune™, Stimune™, or any combination thereof.

Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, ocular) or via a parenteral route (e.g., intradermal, intramuscular, subcutaneous). Vaccine compositions can be administered alone, or can be co-administered or sequentially administered with other treatments or therapies. Forms of administration may include suspensions and preparations for parenteral, subcutaneous, intradermal or intramuscular administration (e.g., injectable administration) such as sterile suspensions or emulsions. Vaccines may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

In a further aspect, described herein is a neoglycoconjugate vaccine or an adaptive immune response-triggering composition produced by a method described herein and/or comprising a neoglycoconjugate as described herein and a pharmaceutically acceptable excipient and/or adjuvant as described herein. In embodiments, the neoglycoconjugate vaccine may be a prophylactic vaccine or a therapeutic vaccine. In embodiments, the vaccine compositions described herein may comprise one or more TACAs and the vaccine composition may be an anti-cancer vaccine against a cancer expressing the TACA. In embodiments, the cancer may be B-cell lymphoma, breast cancer, colon cancer, non-small cell lung cancer, melanoma, neuroblastoma, ovary, prostate, sarcoma, small cell lung cancer, or stomach cancer.

In some aspects, described herein is a method of immunizing, vaccinating, or treating a subject comprising administering to the subject a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein.

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for use in immunizing, vaccinating, or treating a subject having a disease, or for detecting the presence of an antibody that specifically binds to the neoglycoconjugate or for detecting said immunization, vaccination, or treatment (e.g., in a biological sample from the subject).

In some embodiments, described herein is a neoglycoconjugate produced by a method as described herein, a synthetic neoglycoconjugate as described herein, or an adaptive immune response-triggering composition produced by a method as described herein, for the manufacture of a vaccine for immunizing or treating a subject having a disease, or for detecting the presence of an antibody that specifically binds to the neoglycoconjugate or for detecting said immunization or treatment (e.g., in a biological sample from the subject).

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for use in the treatment of a subject having a disease associated with increased expression of said carbohydrate antigen.

In some embodiments, described herein is a neoglycoconjugate produced by a method as described herein, a synthetic neoglycoconjugate as described herein, a neoglycoconjugate vaccine or an adaptive immune response-triggering composition produced by a method as described herein, or a neoglycoconjugate vaccine as described herein, for detecting or screening for the presence of an antibody that specifically binds to the carbohydrate antigen or a tumor-circulating cell comprising the carbohydrate antigen, or for detecting the presence of antibodies resulting from an immunization or vaccination with the carbohydrate antigen. In some embodiments, the detection or screening may be performed via any suitable detection method such as an immunosorbent assay, ELISA, microarray, or immunoblot analysis.

In further aspects, described herein is a method of treating a subject comprising administering a neoglycoconjugate or neoglycoconjugate immunogen as defined herein or produced by a method as described herein, to generate an immune response in said subject to a carbohydrate antigen, and optionally screening a biological sample from said subject for the presence of antibodies that specifically binds to the carbohydrate antigen.

In a further aspects, described herein is a glycoconjugate for use as therapeutic and/or diagnostic tools relating to the SARS-CoV-2. More particularly, described herein is a glycoconjugate for use in immunizing a subject against SARS-CoV-2, for use in triggering the production of anti-SARS-CoV-2 antibodies in a subject, for use in inducing a cell-mediated immune response in a subject against SARS-CoV-2, or any combination thereof. Also described herein is a glycoconjugate for use in detection/diagnostic tools relating to SARS-CoV-2. For example, described herein is a glycoconjugate for use in detecting the presence of anti-SARS-CoV-2 antibodies in a sample from a subject.

As used herein, the expression "anti-SARS-CoV-2 antibodies" refers to antibodies that are able to bind to antigens (e.g., carbohydrate antigens) in their native conformations, such as expressed on native recombinant proteins and/or present on assembled virion particles. In contrast, antibodies that bind only to denatured antigens (e.g., under denaturing conditions such as following SDS-PAGE) but not to the same antigens in their native conformations are excluded from the expression "anti-SARS-CoV-2 antibodies".

In some embodiments, the glycoconjugates or vaccine described herein may induce the production of antibodies having neutralizing activity. As used herein, the expression "neutralizing activity" refers to ligands (e.g., antibodies) that bind to SARS-CoV-2 virion particles and inhibit their ability to infect susceptible host cells.

In some embodiments, the glycoconjugates described herein may comprise carbohydrate antigens conjugated to a suitable carrier material (e.g., a carrier protein or peptide, or a non-proteinaceous polymeric material), wherein the carbohydrate antigens comprise or consists of sialylated Thomsen-Friedenreich (TF) antigen, unsialylated TF antigen, sialylated Tn antigen, unsialylated Tn antigen, or any combination thereof. In some embodiments, the carbohydrate antigens comprise a monosialylated TF antigen such as (2,3)-S-TF, and/or disialylated TF antigen such as disialyl core 1. These carbohydrate antigens were detected on recombinantly-expressed SARS-CoV-2 spike (S) protein and/or the S1 fragment thereof at positions corresponding to positions 4 and/or 6 of the peptide fragment VQPTESIVR (SEQ ID NO: 3) by quantitative high resolution mass spectrometry (Example 16; FIGS. 20 and 21). Furthermore, the results shown in Example 17 and FIGS. 22 and 23 demonstrate that at least some of these carbohydrate antigens are available to ligand binding (e.g., with lectins and/or antibodies), and the results shown in Example 18 and FIG. 24 demonstrate that ligands that bind to such carbohydrate antigens inhibit the ability of a pseudotyped virus particle expressing the S protein of SARS-CoV-2 to infect host cells expressing human angiotensin-converting enzyme 2 (ACE2, the receptor to which S binds to gain entry into host cells). These results were unforeseeable, given the multiple reports that the SARS-CoV-2 S protein being excessively shielded largely by N-linked glycans and that O-linked glycans (if detected, as reports are conflicting) represent a minor component to the overall glycosylation profile of the S protein of SARS-CoV-2 that may not be accessible for ligand binding in the context of a pathogenic virion particle (Watanabe et al., 2020; Shajahan et al., 2020; Grant et al., 2020).

In some embodiments, the carbohydrate antigens described herein may be conjugated to a carrier material that comprises a B cell epitope or T cell epitope, for example depending on whether triggering a humoral and cell-mediated immune response is desired. In some embodiments, the carbohydrate antigens may be covalently conjugated to the SARS-CoV-2 S protein fragment of SEQ ID NO: 3 or 4, such as at positions 4 and/or 6 of SEQ ID NO: 3 or at positions 323, 325, and/or 678 of SEQ ID NO: 4. In particular, position 678 of SEQ ID NO: 4 (which is close to the furin cleavage site of the spike protein at R682) has been reported to be O-glycosylated by core-1 and core-2 structures.

In some embodiments, the carrier protein or peptide may comprise an immunogenic fragment of the SARS-CoV-2 S protein sequence of SEQ ID NO: 4, the fragment comprising one or more carbohydrate antigens conjugated to position 323, 325, and/or 678 of SEQ ID NO: 4. In some embodiments, the carbohydrate antigens may be covalently conjugated to a variant of the SARS-CoV-2 S protein fragment of SEQ ID NO: 3, for example a variant wherein the residues at positions 4 and/or 6 may be replaced with lysine and/or cysteine residues, which may facilitate chemical conjugation to the carbohydrate antigens. In some embodiments, the carrier protein or peptide may comprise an immunogenic fragment of a variant of the SARS-CoV-2 S protein sequence of SEQ ID NO: 4 having a lysine or cysteine at positions 323, 325, and/or 678, the fragment comprising one or more carbohydrate antigens conjugated to the lysine or cysteine residues at position 323, 325, and/or 678 of SEQ ID NO: 4. In the case of lysine residues, the carbohydrate antigens may be conjugated to the carrier protein via conjugation methods described herein, or via other conjugation methods known in the field. In the case of cysteine residues, the carbohydrate antigens may be conjugated to the carrier protein via conjugation methods described in for example WO/2019/178699 or U.S. Pat. No. 10,610,576, or via other conjugation methods known in the field. Thus, in some embodiments, the carrier material described herein may comprise or consist of the peptide of SEQ ID NO: 3, or to a variant of the peptide of SEQ ID NO: 3 comprising a cysteine or lysine at positions 4 and/or 6. In some embodiments, the peptide or peptide variant of SEQ ID NO: 3 may be comprised in (e.g., recombinantly engineered into the amino acid sequence) or may be fused to (e.g., as a fusion protein) the carrier material.

In some embodiments, the carrier material is, is from, or comprises: Tetanus Toxoid (TT), Diphtheria Toxoid (DT), cross-reacting material 197 (CRM197), Meningococcal Outer Membrane Protein Complex (OMPC), *H. Influenzae* Protein D (HiD), a virus-like particle (VLP), a cytokine, an immunogenic peptide such as Tetanus Toxin 831-844 (SEQ ID NO: 1 or 2), albumin (such as bovine serum albumin or human serum albumin), keyhole limpet hemocyanin (KLH), or an immunogenic fragment thereof.

In some embodiments, the glycoconjugate may be: (i) the neoglycoconjugate produced by or as defined in a method described herein; (ii) the neocarbohydrate antigen described herein; (iii) the synthetic neoglycoconjugate described herein; or (iv) the neoglycoconjugate vaccine or an adaptive immune response-triggering composition described herein.

In some embodiments, the glycoconjugate may be produced by a method as described in WO/2019/178699 or U.S. Pat. No. 10,610,576. Briefly, in some embodiments, the method may comprise: (a) providing a water-soluble carbohydrate antigen covalently linked to a terminal alkene (alkenyl carbohydrate antigen), the terminal alkene being directly conjugatable to a thiol group via a thiol-ene reaction and wherein the alkenyl carbohydrate antigen is an unprotected, water-soluble alkenyl carbohydrate antigen; (b) providing a carrier material having one or more free thiol groups; and (c) performing a photocatalytic thiol-ene reaction to directly conjugate the carbohydrate antigen to the material at the one or more free thiol groups, thereby producing the glycoconjugate. In further embodiments, the method may comprise one or more features as described in items 51 to 53 listed below.

In some aspects, described herein is a SARS-CoV-2 or COVID-19 vaccine or adaptive immune response-inducing composition comprising one or more glycoconjugates as defined herein, and a pharmaceutically acceptable excipient and/or an adjuvant. The glycoconjugates generally comprise one or more carbohydrate antigens expressed on SARS-CoV-2 virions, such as for example carbohydrate antigens expressed on the S (or S1) protein of SARS-CoV-2. The carbohydrate antigens suitable for a SARS-CoV-2 vaccine as described herein are carbohydrate antigens that are aberrant glycosylation patterns—i.e., those not expressed on normal or healthy cells and tissues of a subject—in order to reduce the risk of triggering an auto-immune response in the subject being administered the vaccine. Following analyses of N-linked and O-linked glycosylation profiles of the SARS-CoV-2 S protein it was found that the majority of the N-linked glycans expressed on the SARS-CoV-2 S protein may not be ideal candidates for glycoconjugate vaccine development, due to their potential resemblance to carbohydrate antigens present on normal or healthy cells and tissues in human subjects. In contrast, analysis of the O-linked glycosylation profile on the SARS-CoV-2 S protein revealed several aberrant O-linked glycans potentially suitable for glycoconjugate vaccine development. In some embodiments, the carbohydrate antigens described herein may comprise one or more of the O-linked glycans identified in Example 16 and FIGS. 20 and 21.

In some embodiments, the glycoconjugates described herein or the SARS-CoV-2 vaccines described herein, induce the production of antibodies that bind to SARS-CoV-2 virion particles, and preferably have neutralizing activity (e.g., inhibit the ability of SARS-CoV-2 virion particles from infecting susceptible host cells).

In some aspects, described herein is a method for vaccinating a subject for SARS-CoV-2 or for triggering the production of anti-SARS-CoV-2 antibodies in a subject, the method comprising administering one or more of the glycoconjugates or the SARS-CoV-2 vaccine described herein.

In some aspects, described herein is a composition for protecting (or for reducing severity) in a subject from infection by a SARS-CoV-2 virus, or for treating COVID-19 (or for reducing complications arising from COVID-19), the composition comprising one or more ligands (e.g., an antibody, antibody fragment, or lectin) that binds to an O-linked glycan expressed on the SARS-CoV-2 S protein. In some embodiments, the O-linked glycan may comprise sialylated TF antigen (mono- or di-sialylated TF antigen), unsialylated TF antigen, sialylated Tn antigen, unsialylated Tn antigen, or any combination thereof. In some embodiments, the one or more ligands may comprise a recombinant monoclonal antibody (e.g., JAA-F11 or humanized JAA-F11). In some embodiments, the ligand may have binding affinity for sialylated TF and/or to unsialylated Tn. In some embodiments, the ligand may have binding affinity for both sialylated and unsialylated TF. In some embodiments, the ligand may be a lectin such as Jacalin or is a Jacalin-related lectin. In this regard, Example 18 and FIG. 24 show that the ligand having the strongest inhibitory effects on the ability of a pseudotyped virus particle expressing the S protein of SARS-CoV-2 to infect host cells was the lectin Jacalin, an *Artocarpus integrifolia* lectin (AIA) is isolated from jackfruit seeds (Sankaranarayanan et al., 1996). Interestingly, Jacalin is known to have binding specificities for both the TF and Tn antigens in either their sialylated or unsialylated forms (Jeyaprakash et al., 2002). Inhibition of pseudovirus infectivity is also shown herein for ligands that bind to only non-sialyl TF antigens such as the lectin PNA and the anti-TF monoclonal antibody JAA-F11 (FIG. 24). In some embodiments, the aforementioned compositions may be formulated as an intranasal composition.

In some aspects, described herein is a complex comprising: (a) a SARS-CoV-2 S protein, or fragment thereof, expressing an O-linked glycan comprising sialylated TF antigen (mono- or di-sialylated TF antigen), unsialylated TF antigen, sialylated Tn antigen, unsialylated Tn antigen, or any combination thereof; and (b) a ligand as defined herein that is bound to the SARS-CoV-2 S protein, or fragment thereof, at the O-linked glycan. In some embodiments, the complex may comprise a SARS-CoV-2 S protein in an intact SARS-CoV-2 virion particle. In some embodiments, such complexes may be formed in vitro or in vivo.

Items

Described herein are one or more of the following items.

1. A method for producing a neoglycoconjugate, the method comprising: (a) providing a neocarbohydrate antigen or neocarbohydrate antigen intermediate comprising a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group; (b) providing a carrier protein or peptide having one or more free amine groups; and (c) performing a coupling reaction to conjugate one or more of the purified neocarbohydrate antigens or neocarbohydrate antigen intermediates to the carrier protein or peptide at the one or more free amine groups via an amide, a carbamate, a sulfonamide, a urea, or a thiourea bond, thereby producing the neoglycoconjugate.

2. The method of item 1, wherein prior to step (a), the neocarbohydrate antigen or neocarbohydrate antigen intermediate in (a) is prepared by a method comprising: (i) providing a carbohydrate antigen covalently linked to a terminal alkene (alkenyl carbohydrate antigen), the terminal alkene being directly conjugatable to a thiol group via a thiol-ene reaction; (ii) providing a thio-linker comprising a first functional group at a first end and a second functional group at a second end, the first functional group being a free thiol group and the second functional group being a carboxyl group, sulfinic acid group, carbonic acid group, isocyanate group, or thiocyanate group; (iii) performing a photocatalytic thiol-ene reaction to directly conjugate the alkenyl carbohydrate antigen to the thio-linker at the first end, thereby producing a neocarbohydrate antigen comprising the carbohydrate antigen at the first end and the second functional group at a second end; (iv) when the second functional group is a carboxyl group, sulfinic acid group, or carbonic acid group, converting the neocarbohydrate antigen to a neocarbohydrate antigen intermediate by replacing the carboxyl group's, sulfinic acid group's, or carbonic acid group's terminal hydroxyl group with a better leaving group for conjugation to a free amine group of a polypeptide; and (v) purifying the neocarbohydrate antigen or the neocarbohydrate antigen intermediate.

3. The method of item 2, wherein the photocatalytic thiol-ene reaction in (iii) is performed under reaction conditions that retain the carbohydrate antigen's antigenicity, and/or structure.

4. The method of item 2 or 3, wherein said photocatalytic thiol-ene reaction is performed in the presence of a catalyst, wherein the catalyst is: a water-soluble catalyst, such as a water-soluble free radical-generating azo compound; 2,2'-azobis[2-(2-imidazolin-2-yl)propane]dihydrochloride (Vazo 44 or VA-044); 2,2'-azobis(2-amidinopropane) dihydrochloride (AAPH); lithium phenyl-2,4,6-trimethylbenzoylphosphinate (LAP); metals or metal ions having photoinitiator activity; a peroxide; tert-butyl hydroperoxide; benzoylperoxide; ammonium persulfate; or any derivative thereof having photoinitiator activity; or a water-insoluble catalyst, such as a water-insoluble free radical-generating azo compound, 2,2-dimethoxy-2-phenylacetophenone (DMPA), azobisisobutyronitrile (AIBN), 2,2'-azobis(2-methylpropionitrile), 4,4'-Azobis (4-cyanopentanoic acid) (ACVA), 1,1'-azobis(cyanocyclohexane) (ACHN), diazenedicarboxylic acid bis(N,N-dimethylamide) (TMAD); azodicarboxylic acid dipiperidide (ADD), or any derivative thereof having photoinitiator activity.

5. The method of any one of items 2 to 4, wherein said photocatalytic thiol-ene reaction comprises irradiation under ultraviolet light (e.g., short-wave ultraviolet light such as at about 254 nm, or long-wave ultraviolet light such as at about 355 nm or 365 nm).

6. The method of any one of items 2 to 5, wherein: said photocatalytic thiol-ene reaction comprises reacting between 1 to 200 or 1 to 100 molar equivalents of the alkenyl carbohydrate antigen per free thiol group of the thio-linker; said photocatalytic thiol-ene reaction is performed for 10 to 300, 10 to 270, 10 to 240, 10 to 210, 10 to 180, 10 to 150, 10 to 120, 10 to 90, 10 to 60, or 10 to 30 minutes; is performed at a pH between about 3.0, 3.1, 3.2, 3.3, 3.4, 3.5, 3.6, 3.7, 3.8, 3.9, or 4.0, and about 4.5, 4.6, 4.7, 4.8, 4.9, 5.0, 5.5, 6.0, 6.5, 7.0, 7.5, 8.0, 8.5, 9.0, 9.5, or 10; or any combination thereof.

7. The method of any one of items 2 to 6, wherein said carbohydrate antigen is linked to the terminal alkene preferably using a linker, by a via glycosidic bond, such as is an O-glycosidic bond, an S-glycosidic bond, an N-glycosidic bond, or a C-glycosidic bond, or a bond obtained by reductive amination, such as between an allyl amine and a reducing sugar.

8. The method of any one of items 2 to 7, wherein the thio-linker in (ii) comprises the structure:

$$HS\diagdown\diagup_Y(\diagdown)_o Z$$

wherein: Y is —(CH$_2$)$_n$— or —(OCH$_2$CH$_2$O)$_n$—; Z is —CO$_2$H, —SO$_2$H, —O—C(O)—H, —N=C=O, or —N=C=S; O is 1, 2, 3, 4, or 5; O is 0 and Z is —CO— and Y is —(OCH$_2$CH$_2$O)$_n$—; or O is 0 and Z is —SO$_2$— and Y is —(OCH$_2$CH$_2$O)$_n$—.

9. The method of any one of items 1 to 8, wherein the carbohydrate portion of the carbohydrate antigen, the alkenyl carbohydrate antigen, the neocarbohydrate antigen, the neocarbohydrate antigen intermediate, and/or the neoglycoconjugate remain unprotected throughout the method.

10. The method of any one of items 1 to 9, wherein the leaving group is an active ester group (e.g., a fluorophenyl group (e.g., OPhF5, OPhF4 (para SO$_3$Na)), or a succinimidyl group).

11. The method of any one of items 1 to 10, wherein the method avoids carrier protein or peptide self-crosslinks between aspartic/glutamic acid residues and ε-lysine amines present in the same carrier protein or peptide.

12. The method of any one of items 1 to 11, wherein the number of neocarbohydrate antigens conjugated to the carrier protein or peptide is controlled by the efficacy and/or stoichiometry of the reactants (e.g., the molar ratio of the carrier protein or peptide to the neocarbohydrate antigen or the neocarbohydrate antigen intermediate).

13. The method of any one of items 1 to 12, wherein the carbohydrate antigen is or comprises: a tumor associated carbohydrate antigen (TACA) (e.g., Tn, S-Tn, Thomsen-Friedenreich (TF), (2,3)-S-TF, (2,6)-S-TF, Globo H, PSA, GD2, GD3, GM2, GM3, N-glycolyl-GM3, Fucosyl GM1, Le$^a$, sLe$^a$, Le$^x$, sLe$^x$, Le$^y$, or any combination thereof); a viral polysaccharide antigen; or a bacterial capsular polysaccharide (CPS) (e.g., a CPS which is, is from, or comprises a Pneumococcal and/or Streptococcal polysaccharide serotype, meningococcal CPS, or influenza CPS (such as influenza type a or b CPS)).

14. The method of any one of items 1 to 19, wherein the coupling reaction in (c) conjugates at least two of the same neocarbohydrate antigen or more than one type of neocarbohydrate antigen to the carrier protein or peptide, thereby producing a multi-valent neoglycoconjugate (e.g., a multi-valent neoglycoconjugate comprising 2, 3, 4, 5, 6, 7, 8, 9, 10, 11, 12, 13, 14, 15, or more of the same or different types of neocarbohydrate antigens conjugated to the carrier protein or peptide).

15. The method of any one of items 1 to 14, wherein the carrier protein or peptide is a protein or peptide that was engineered to add one or more further lysine residues, for example at the amino terminus, the carboxy terminus, or at a solvent-accessible position of the carrier protein or peptide.

16. The method of any one of items 1 to 15, wherein the carrier protein or peptide is, is from, or comprises: Tetanus Toxoid (TT), Diphtheria Toxoid (DT), cross-reacting material 197 (CRM197), Meningococcal Outer Membrane Protein Complex (OMPC), *H. Influenzae* Protein D (HiD), a cytokine, an immunogenic peptide such as Tetanus Toxin 831-844 (SEQ ID NO: 1 or 2), albumin (such as bovine serum albumin or human serum albumin), keyhole limpet hemocyanin (KLH), or an immunogenic fragment thereof.

17. The method of any one of items 1 to 16, wherein the neoglycoconjugate has the structure:

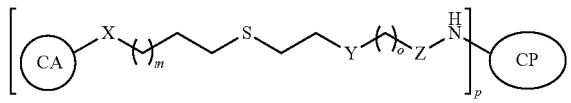

wherein: CA is or comprises the carbohydrate antigen; CP-NH is the carrier protein or peptide having one or more amine groups; X is O, S, NR$_1$, or CH$_2$; R$_1$ is H, COH (formamide), COMe, or COEt; m is 1, 2, 3, 4, or 5; Y is —(CH$_2$)$_n$— or —(OCH$_2$CH$_2$O)$_n$—; n is 0, 1, 2, 3, 4, or 5; o is 0, 1, 2, 3, 4, or 5; or o is 0 and Z is —CO— and Y is —(OCH$_2$CH$_2$O)$_n$—; or o is 0 and Z is —SO$_2$— and Y is —(OCH$_2$CH$_2$O)$_n$—; Z is —CO—, —NR$_2$SO$_2$—, —OCO—, —NR$_2$CO—, or —NR$_2$CS—, R$_2$ is H, Me, or Et; and p is 1 to 50.

18. The method of any one of items 1 to 18, wherein the neoglycoconjugate is a neoglycoconjugate immunogen, the carrier protein or peptide is immunogenic when administered to a subject, and conjugation of the carbohydrate antigen to the carrier protein or peptide via the thio-1 inker increases the immunogenicity of the carbohydrate antigen upon administration to the subject as compared to a corresponding administration of the unconjugated carbohydrate antigen.

19. The method of item 18, wherein the thio-linker is non-immunogenic to the subject such that administration of the neoglycoconjugate immunogen to the subject does not trigger antibodies against the thio-linker comprised in the neoglycoconjugate immunogen.

20. The method of item 18 or 19, wherein said neocarbohydrate antigen, following conjugation to the carrier protein or peptide, is not cleavable from the carrier protein or peptide by an endogenous enzyme of the subject.

21. The method of any one of items 18 to 20, wherein the neocarbohydrate antigen comprises a B cell epitope, and/or induces a humoral immune response in the subject; and/or comprises a T cell epitope, and/or induces a cell-mediated immune response in the subject.

22. The method of any one of items 18 to 21, wherein the carrier protein or peptide comprises a human T cell epitope, and/or induces a cell-mediated immune response in the subject.

23. The method of any one of items 18 to 22, wherein the neoglycoconjugate immunogen induces a cell-mediated immune response to the carbohydrate antigen upon administration to the subject.

24. A neocarbohydrate antigen or neocarbohydrate antigen intermediate comprising a linker having a first end and a second end, wherein the first end is conjugated to a carbohydrate antigen via a thio ether bond and the second end comprises a functional group reactable with a free amine group, the functional group being —COX, —SO$_2$X, —O—C(O)—X, —N=C=O, or —N=C=S, wherein X is a leaving group.

25. The neocarbohydrate antigen or neocarbohydrate antigen intermediate of item 24, wherein: the carbohydrate antigen is unprotected; the leaving group is as defined in item 10; the carbohydrate antigen is as defined in item 13; or any combination thereof.

26. A synthetic neoglycoconjugate comprising a linker having a first end and a second end, wherein the first end is conjugated to a carbohydrate antigen via a thio ether bond and the second end is conjugated to a carrier protein or peptide at one or more free amine groups therein via an amide, a carbamate, a sulfonamide, a urea, or a thiourea bond.

27. A synthetic neoglycoconjugate comprising one or more carbohydrate antigens (CA) conjugated to one or more amine groups of a carrier protein or peptide (CP-NH) via a linker, the synthetic neoglycoconjugate having the structure:

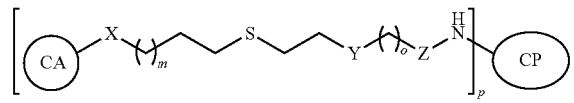

wherein: X is O, S, NR$_1$, or CH$_2$; R$_1$ is H, COH (formamide), COMe, or COEt; m is 1, 2, 3, 4, or 5; Y is —(CH$_2$)$_n$— or —(OCH$_2$CH$_2$O)$_n$—; n is 0, 1, 2, 3, 4, or 5; o is 0, 1, 2, 3, 4, or 5; or o is 0 and Z is —CO— and Y is —(OCH$_2$CH$_2$O)$_n$—; or o is 0 and Z is —SO$_2$— and Y is —(OCH$_2$CH$_2$O)$_n$—; Z is —CO—, —NR$_2$SO$_2$—, —OCO—, —NR$_2$CO—, or —NR$_2$CS—; R$_2$ is H, Me, or Et; and p is 1 to 50.

28. The synthetic neoglycoconjugate of item 26 or 27, wherein: the carbohydrate antigen is unprotected;—the carbohydrate antigen is as defined in item 13; the neoglycoconjugate is a multivalent neoglycoconjugate as defined in item 14; the carrier protein or peptide is as defined in item 15, 16, 18, or 22; the neoglycoconjugate has the structure as defined in item 17; the linker is as defined in item 19; the neocarbohydrate antigen is as defined in item 20 or 21; the synthetic neocarbohydrate is produced by the method of any one of items 1 to 25; or any combination thereof.
29. A method for producing a neoglycoconjugate vaccine or an adaptive immune response-triggering composition, the method comprising formulating the neoglycoconjugate prepared by the method of any one of items 1 to 23 or as defined in any one of items 24 to 28, with a pharmaceutically acceptable excipient, and/or an adjuvant.
30. The method of item 29, wherein the adjuvant is or comprises: an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide (such as CPG), an immunostimulatory lipid, Freund's adjuvant, RIBI's adjuvant, QS-21, muramyl dipeptide, TiterMax, Steviune, Stimune, or any combination thereof.
31. A neoglycoconjugate vaccine or an adaptive immune response-triggering composition produced by the method of item 29 or 30, and/or comprising the neoglycoconjugate as defined in any one of items 1 to 28 and a pharmaceutically acceptable excipient and/or an adjuvant.
32. The neoglycoconjugate vaccine of item 31, which is a prophylactic vaccine or a therapeutic vaccine (e.g., against cancers that expresses tumor associated carbohydrate antigens, such as breast cancer, prostate cancer, stomach cancer, B-cell lymphoma, colon cancer, lung cancer, melanoma, neuroblastoma, ovarian cancer, sarcoma, small cell lung cancer; or against viruses or bacteria that express carbohydrate antigens).
33. A method of immunizing, vaccinating, or treating a subject comprising administering to the subject the neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32.
34. The neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32, for use in immunizing, vaccinating, or treating a subject having a disease (e.g., cancers that expresses tumor associated carbohydrate antigens, such as breast cancer, prostate cancer, stomach cancer, B-cell lymphoma, colon cancer, lung cancer, melanoma, neuroblastoma, ovarian cancer, sarcoma, small cell lung cancer; or viruses or bacteria that express carbohydrate antigens), or for detecting the presence of an antibody that specifically binds to the neoglycoconjugate or for detecting said immunization, vaccination, or treatment (e.g., in a biological sample from the subject).
35. Use of the neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32, for immunizing, vaccinating, or treating a subject having a disease (e.g., cancers that expresses tumor associated carbohydrate antigens, such as breast cancer, prostate cancer, stomach cancer, B-cell lymphoma, colon cancer, lung cancer, melanoma, neuroblastoma, ovarian cancer, sarcoma, small cell lung cancer; or viruses or bacteria that express carbohydrate antigens), or for detecting the presence of an antibody that specifically binds to the neoglycoconjugate or for detecting said immunization, vaccination, or treatment (e.g., in a biological sample from the subject).
36. Use of the neoglycoconjugate produced by the method of any one of items 1 to 23, the synthetic neoglycoconjugate of any one of items 26 to 28, the adaptive immune response-triggering composition produced by the method of item 29 or 30, for the manufacture of a vaccine for immunizing or treating a subject having a disease (e.g., cancers that expresses tumor associated carbohydrate antigens, such as breast cancer, prostate cancer, stomach cancer, B-cell lymphoma, colon cancer, lung cancer, melanoma, neuroblastoma, ovarian cancer, sarcoma, small cell lung cancer; or viruses or bacteria that express carbohydrate antigens), or for detecting the presence of an antibody that specifically binds to the neoglycoconjugate or for detecting said immunization or treatment (e.g., in a biological sample from the subject).
37. Use of the neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32, for the treatment of a subject having a disease associated with increased expression of said carbohydrate antigen (e.g., cancers such as breast cancer, prostate cancer, stomach cancer, B-cell lymphoma, colon cancer, lung cancer, melanoma, neuroblastoma, ovarian cancer, sarcoma, small cell lung cancer; or viruses or bacteria that express carbohydrate antigens).
38. Use of the neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32, for producing an antibody that specifically binds to the neoglycoconjugate, or for detecting an antibody that specifically binds to the neoglycoconjugate immunogen.
39. Use of the neoglycoconjugate produced by the method of any one of items 1 to 23, the synthetic neoglycoconjugate of any one of items 26 to 28, the neoglycoconjugate vaccine or an adaptive immune response-triggering composition produced by the method of item 29 or 30, or the neoglycoconjugate vaccine of item 31 or 32, for detecting or screening for the presence of an antibody that specifically binds to the carbohydrate antigen or a tumor-circulating cell comprising the carbohydrate antigen, or for detecting the presence of antibodies resulting from an immunization or vaccination with the carbohydrate antigen.
40. The use of item 39, wherein the detection or screening is performed via any suitable detection method such as an immunosorbent assay, ELISA, microarray, or immunoblot analysis.
41. A method of treating a subject comprising administering a neoglycoconjugate or neoglycoconjugate immunogen as defined in any preceding items or produced by a method as defined by any preceding items, to generate an immune response in said subject to a carbohydrate antigen, and optionally screening a biological sample from said subject for the presence of antibodies that specifically binds to the carbohydrate antigen.

42. A glycoconjugate for use in immunizing a subject against SARS-CoV-2, for use in triggering the production of anti-SARS-CoV-2 antibodies in a subject, or for use in detecting the presence of anti-SARS-CoV-2 antibodies in a sample from a subject, the glycoconjugate comprising carbohydrate antigens conjugated to a suitable carrier material (e.g., a carrier protein or peptide), wherein the carbohydrate antigens comprise or consist of sialylated Thomsen-Friedenreich (TF) antigen, unsialylated TF antigen, sialylated Tn antigen, unsialylated Tn antigen, or any combination thereof.

43. The glycoconjugate for use of item 42, wherein the carbohydrate antigens comprise or consist of sialylated TF antigen (e.g., (2,3)-S-TF and/or disialyl core 1).

44. The glycoconjugate for use of item 42 or 43, wherein the carbohydrate antigens comprise or consist of Tn (e.g., sialylated and/or unsialylated Tn).

45. The glycoconjugate for use of any one of items 42 to 44, wherein the carrier material comprises a peptide which is a B cell epitope or T cell epitope.

46. The glycoconjugate for use of any one of items 42 to 45, wherein the carbohydrate antigens are covalently conjugated to positions 4 and/or 6 of the peptide of SEQ ID NO: 3, or to a variant of the peptide of SEQ ID NO: 3 comprising a cysteine or lysine at positions 4 and/or 6.

47. The glycoconjugate for use of item 46, wherein the peptide or peptide variant of SEQ ID NO: 3 is comprised in or fused to the carrier material.

48. The glycoconjugate for use of any one of items 42 to 47, wherein the carrier material is, is from, or comprises: Tetanus Toxoid (TT), Diphtheria Toxoid (DT), cross-reacting material 197 (CRM197), Meningococcal Outer Membrane Protein Complex (OMPC), *H. Influenzae* Protein D (HiD), a virus-like particle (VLP), a cytokine, an immunogenic peptide such as Tetanus Toxin 831-844 (SEQ ID NO: 1 or 2), albumin (such as bovine serum albumin or human serum albumin), keyhole limpet hemocyanin (KLH), or an immunogenic fragment thereof.

49. The glycoconjugate as defined in any one of items 42 to 48, wherein the glycoconjugate is: (i) the neoglycoconjugate produced by or as defined in the method of any one of items 1 to 23; (ii) the neocarbohydrate antigen of item 24 or 25; (iii) the synthetic neoglycoconjugate of item 27 or 28; or (iv) the neoglycoconjugate vaccine or an adaptive immune response-triggering composition as defined in or produced by the method of item 29 or 30 or as defined in item 31 or 32.

50. The glycoconjugate as defined in any one of items 42 to 48, which is produced by a method comprising: (a) providing a water-soluble carbohydrate antigen covalently linked to a terminal alkene (alkenyl carbohydrate antigen), the terminal alkene being directly conjugatable to a thiol group via a thiol-ene reaction and wherein the alkenyl carbohydrate antigen is an unprotected, water-soluble alkenyl carbohydrate antigen; (b) providing a carrier material having one or more free thiol groups; and (c) performing a photocatalytic thiol-ene reaction to directly conjugate the carbohydrate antigen to the material at the one or more free thiol groups, thereby producing the glycoconjugate.

51. The glycoconjugate of item 50, wherein: the photocatalytic thiol-ene reaction is performed under reaction conditions that avoid carrier material denaturation, and/or that retain the carrier material's activity, antigenicity, and/or structure; the photocatalytic thiol-ene reaction is performed is performed in the absence of any organic solvent, or wherein said photocatalytic thiol-ene reaction is performed in the presence of an organic solvent at a concentration sufficiently low to avoid carrier material denaturation; the photocatalytic thiol-ene reaction is performed in the presence of a catalyst, wherein the catalyst is: a water-soluble catalyst, such as a water-soluble free radical-generating azo compound; 2,2'-azobis[2-(2-imidazolin-2-yl)propane]dihydrochloride (Vazo 44 or VA-044); 2,2'-azobis(2-amidinopropane) dihydrochloride (AAPH); lithium phenyl-2,4,6-trimethylbenzoylphosphinate (LAP); metals or metal ions having photoinitiator activity; a peroxide; tert-butyl hydroperoxide; benzoylperoxide; ammonium persulfate; or any derivative thereof having photoinitiator activity; or a water-insoluble catalyst, such as a water-insoluble free radical-generating azo compound, 2,2-dimethoxy-2-phenylacetophenone (DMPA), azobisisobutyronitrile (AIBN), 2,2'-azobis(2-methylpropionitrile), 4,4'-Azobis(4-cyanopentanoic acid) (ACVA), 1,1'-azobis(cyanocyclohexane) (ACHN), diazenedicarboxylic acid bis(N,N-dimethylamide) (TMAD); azodicarboxylic acid dipiperidide (ADD), or any derivative thereof having photoinitiator activity; the photocatalytic thiol-ene reaction comprises irradiation under ultraviolet light; the photocatalytic thiol-ene reaction comprises reacting between 1 to 200 molar equivalents of the alkenyl carbohydrate antigen per free thiol group of the carrier material; and/or wherein said photocatalytic thiol-ene reaction is performed for 10 to 300, 10 to 270, 10 to 240, 10 to 210, 10 to 180, 10 to 150, 10 to 120, 10 to 90, 10 to 60, or 10 to 30 minutes, and/or for a sufficient time to achieve at least a 5, 10, 15, 20, 25, 30, 35, 40, 45, or 50-fold reduction in total free thiol concentration in the carrier material; the photocatalytic thiol-ene reaction is performed at a pH that avoids carrier material denaturation; the photocatalytic thiol-ene reaction, following conjugation to the carrier material, produces a carbohydrate antigen that is not cleavable from the carrier material by an endogenous enzyme of the subject; the alkenyl carbohydrate antigen is covalently linked to the terminal alkene, and/or the carbohydrate antigen is conjugated to the carrier material, via an O-glycosidic bond, an S-glycosidic bond, an N-glycosidic bond, or a C-glycosidic bond, or a bond obtained by reductive amination between an allyl amine and a reducing sugar; the photocatalytic thiol-ene reaction conjugates more than one type of carbohydrate antigen to the carrier material; the carbohydrate antigen in (a) is linked to the terminal alkene via a linker; and/or the carrier material provided in step (b) is: (i) a carrier material comprising one or more cysteine residues having the one or more free thiol groups, (ii) a carrier material engineered to add one or more further cysteine residues at a solvent-accessible position of the carrier material; (iii) a carrier material treated with a thiolating agent; (iv) a carrier material treated with a reducing agent; or (v) any combination of (i) to (iv).

52. The glycoconjugate as defined in any one of items 42 to 48, which is:
(a) a synthetic glycoconjugate having the structure:

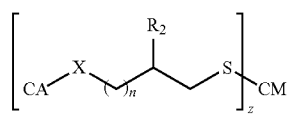

wherein: CA is the carbohydrate antigen; S-CM is the carrier material having z sulfur atoms available for conjugation, wherein z is at least 1; X is O, S, NR$_1$, or CH$_2$; R1 is —H, —COH, —COCH$_3$, or —COEt; n is 0, 1, 2, 3, 4, or 5; and R$_2$ is H or Me; or a stereoisomer thereof; or (b) a synthetic glycoconjugate having the structure:

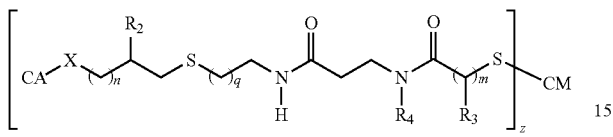

wherein: CA is the carbohydrate antigen; S-CM is the carrier material having z sulfur atoms available for conjugation, wherein z is at least 1; X is S, NR$_1$, CH$_2$ or O; R$_1$ is —H, —COH, —COMe, or —COEt; n is 0, 1, 2, 3, 4, or 5; R$_2$ is H or Me; q is 1, 2, 3, 4, or 5; R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; or a stereoisomer thereof; or (c) a synthetic glycoconjugate having the structure:

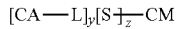

wherein: CA is the carbohydrate antigen; y is at least 1; and when y is more than 1, CA are identical or different; [S]$_z$-CM is the carrier material having z sulfur atoms available for conjugation, wherein z is at least equal to y; and L is a linker selected from the group consisting of linkers having the structure:

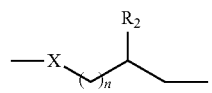

wherein: X is O, S, NR$_1$, or CH$_2$; R$_1$ is —H, —COH, —COCH$_3$, or —COEt; n is 0, 1, 2, 3, 4, or 5; and R$_2$ is H or Me; and when y is more than 1, L are identical or different; or a stereoisomer thereof; or (d) a synthetic glycoconjugate having the structure:

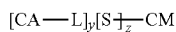

wherein: CA is the carbohydrate antigen; y is at least 1; and when y is more than 1, CA are identical or different; S-CM is the carrier material having z sulfur atoms available for conjugation, wherein z is at least 1 and is at least equal to y; and L is a linker selected from the group consisting of linkers having the structure:

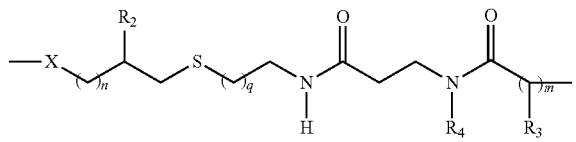

wherein: X is S, NR$_1$, CH$_2$ or O; R$_1$ is —H, —COH, —COMe, or —COEt; n is 0, 1, 2, 3, 4, or 5; R$_2$ is H or Me; q is 1, 2, 3, 4, or 5; R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and when y is more than 1, L are identical or different; or a stereoisomer thereof; or (e) a synthetic glycoconjugate having the structure:

wherein: CA is the carbohydrate antigen; y is at least 1; and when y is more than 1, CA are identical or different; [S]$_z$-CM is the carrier material having z sulfur atoms available for conjugation, wherein z is at least equal to y; and L is a linker selected from the group consisting of linkers having the structure:

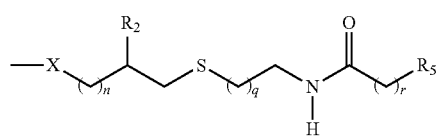

wherein: X is S, NR$_1$, CH$_2$ or O; R$_1$ is —H, —COH, —COMe, or —COEt; n is 0, 1, 2, 3, 4, or 5; R$_2$ is H or Me; q is 1, 2, 3, 4, or 5; r is 1, 2, 3, 4 or 5; R$_5$ is S-CM, a covalent bond, or a radical of structure:

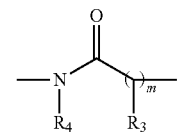

wherein R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and when y is more than 1, L are identical or different; or a stereoisomer thereof.

53. The glycoconjugate of item 52:
having the structure as defined in (e), wherein the linker has the structure:

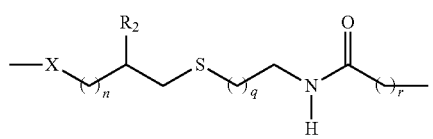

wherein: X is S, NR$_1$, CH$_2$ or O; R$_1$ is —H, —COH, —COMe, or —COEt; n is 0, 1, 2, 3, 4, or 5; R$_2$ is H or Me; q is 1, 2, 3, 4, or 5; and r is 1, 2, 3, 4 or 5;

having the structure as defined in (e), wherein the linker has the structure:

[Chemical structure]

or

[Chemical structure]

wherein: X is S, NR$_1$, CH$_2$ or O; R$_1$ is —H, —COH, —COMe, or —COEt; n is 0, 1, 2, 3, 4, or 5; R$_2$ is H or Me; q is 1, 2, 3, 4, or 5; and r is 1 or 2;

wherein the carrier material is or comprises a polymer, a polypeptide, a carrier protein, a solid support, a particle, or any other material having at least one or more a free thiol group suitable for conjugation to the carbohydrate antigen via a photocatalytic thiol-ene reaction;

wherein the conjugate material is coupled to at least two of the same carbohydrate antigen or to more than one type of carbohydrate antigen, thereby producing a multi-valent synthetic glycoconjugate;

wherein the carbohydrate antigen is not cleavable from the carrier protein by an endogenous enzyme of the subject; or any combination thereof.

54. A SARS-CoV-2 vaccine comprising one or more glycoconjugates as defined in any one of items 42 to 53, and a pharmaceutically acceptable excipient and/or an adjuvant.

55. The SARS-CoV-2 vaccine of item 54 comprising at least two different glycoconjugates, each glycoconjugate comprising a carrier material conjugated to a at least two different carbohydrate antigens selected from sialylated TF antigen (mono- or di-sialylated TF antigen), unsialylated TF antigen, sialylated Tn antigen, and unsialylated Tn antigen.

56. The glycoconjugate as defined in any one of items 42 to 53, or the SARS-CoV-2 vaccine of item 54 or 55, wherein the glycoconjugate or vaccine induces the production of antibodies that bind to SARS-CoV-2 virion particles, and preferably have neutralizing activity.

57. A method for vaccinating a subject for SARS-CoV-2 or for triggering the production of anti-SARS-CoV-2 antibodies in a subject, the method comprising administering the glycoconjugates of any one of items 42 to 53 or 56, or the SARS-CoV-2 vaccine of any one of items 54 to 56.

58. A composition for protecting a subject from infection by a SARS-CoV-2 virus, or for treating COVID-19, the composition comprising one or more ligands (e.g., an antibody, antibody fragment, or lectin) that bind to an O-linked glycan expressed on the SARS-CoV-2 S protein, the O-linked glycan comprising sialylated TF antigen (mono- or di-sialylated TF antigen), unsialylated TF antigen, sialylated Tn antigen, unsialylated Tn antigen, or any combination thereof.

59. The composition for use of item 58, wherein the one or more ligands comprise a recombinant monoclonal antibody (e.g., JAA-F11 or humanized JAA-F11).

60. The composition for use of item 58, wherein the one or more ligands comprise a lectin (e.g., that binds to both sialylated and unsialylated TF antigen forms).

61. The composition for use of any one of items 58 to 60, wherein the lectin is Jacalin or is a Jacalin-related lectin.

62. The composition for us of any one of items 58 to 61, which is formulated as an intranasal composition.

63. A complex comprising: (a) a SARS-CoV-2 S protein, or fragment thereof, expressing an O-linked glycan comprising sialylated TF antigen (mono- or di-sialylated TF antigen), unsialylated TF antigen, sialylated Tn antigen, unsialylated Tn antigen, or any combination thereof; and (b) a ligand as defined in any one of items 58 to 61 that is bound to the SARS-CoV-2 S protein, or fragment thereof, at the O-linked glycan.

64. The complex of item 63, wherein the SARS-CoV-2 S protein, or fragment thereof, is comprised in an intact SARS-CoV-2 virion particle.

EXAMPLES

Example 1: General Methods

Reactions were carried out under argon atmosphere using commercially available HPLC grade reagents. Commercially available reagents (Sigma Aldrich) were used without further purification. N-Acetyl-D-galactosamine and N-acetylneuraminic acid were provided from Rose Scientific Ltd. Alberta, Canada. The Fmoc-β-Ala-Wang resin and Fmoc amino acid were available commercially from Peptide Technologies Ltd, Pierrefonds, Qc, Canada. Progress of reactions was monitored by thin-layer chromatography using silica gel 60 F$_{254}$ coated plates (E. Merck). The conjugation by the click thiol-ene photoreaction was done in a quartz cuvette (10×10 mm path length, Fisher Scientific Canada, Cat. No. 14-958-130) place between two hand held UV 365 nm lamps (UV-AC Hand Lamp, Dual 254/365 nm UV; 115V-60 Hz, 0.16 amps, VWR Canada, Cat. No. 89131-492). Flash chromatography was performed using ZEOprep™ silica gel 60 (40-63 μm) from Canadian Life Science. Detection was carried out under UV light or by spraying with 20% ethanolic sulfuric acid or molybdate or KMnO$_4$ solution followed by heating. NMR spectra were recorded on Bruker ULTRASHIELD™ 300 MHz and Bruker Avance™ III HD 600 MHz spectrometers. Proton and carbon chemical shifts (δ) are reported in ppm relative to the chemical shift of residual CHCl$_3$, which was set at 7.26 ppm ($^1$H) and 77.16 ppm ($^{13}$C). Coupling constants (J) are reported in Hertz (Hz), and the following abbreviations are used for peak multiplicities: singlet (s), doublet (d), doublet of doublets (dd), doublet of doublet with equal coupling constants (t$_{ap}$), triplet (t), multiplet (m). Analysis and assignments were made using COSY (Correlated SpectroscopY) and HSQC (Heteronuclear Single Quantum Coherence) experiments. High-resolution mass spectra (HRMS) were measured with a LC-MS-TOF (Liquid Chromatography Mass Spectrometry Time Of Flight) instrument from Agilent technologies in positive and/or negative electrospray mode by the analytical platform of UQAM. Either protonated ions (M+H)$^+$ or sodium adducts (M+Na)$^+$ were used for empirical formula confirmation. The native TT and TT-conjugate were dialyzed using 2000 KDa benzoylated dialysis tubing (Sigma-Aldrich (Ontario, Canada). The thiol contents of both native and conjugated TT were determined by the Ellman test at 412 nm (Ellman, G. L. *Arch. Biochem. Biophys.* 1959, 82, 70-77). The total sugar content of the TT-conjugate was determined by the colorimetric DuBois test measured at 492 nm (Dubois, M.; Gilles, K. A.; Hamilton, J. K.; Rebers, P. A.; Smith, F. Colorimetric Method for Determination of Sugars and Related Substances. *Anal. Chem.*, 1956, 28, 350-356) by UV/VIS spectrometry. Dynamic Light Scattering (DLS), particle size distributions were measured in PBS using a Zetasizer Nano S90 from Malvern. The mouse monoclonal IgG3 antibody JAA-F11 was produced as previously described in Rittenhouse-Diakun et al., 1998.

General Solid Phase Peptide Synthesis (SPPS) Procedure

The procedure of Solid-Phase Peptide Synthese (SPPS) was followed under literature procedure (Papadopoulos et al., 2012) and stared with Fmoc-β-Ala-Wang resin (650 mg, 0.34 mmol, 1.0 equiv.; 100-200 mesh, loading=0.52 mmol/g). The reactions were conducted by rotation agitation in Econo-Pac disposable columns 1.5×14 cm (20 mL) (Bio-Rad Laboratories, ON, Canada). The resin was swollen in CH$_2$Cl$_2$ during 1 h, then filtered and reconditioned in DMF during i 1. The Fmoc-protecting group of the commercial resin or of amino acids were removed with a solution of 20% piperidine in DMF (5 mL, 2×5 min then 1×10 min). The solvents and reagents were removed by filtration, and the resin was washed with DMF, CH$_2$Cl$_2$ and MeOH (3× with each solvent). The presence of free amino groups was verified by a Kaiser test or TNBS test. The free amines on the resin were treated with a solution de preactivated Fmoc amino acid: 3 equiv of amino acid, 3 equiv of HBTU (N,N,N',N'-Tetramethyl-O-(1H-benzotriazol-1-yl)uronium hexafluorophosphate) and a catalytic amount of HOB t (1-hydroxybenzotriazole) in DMF at 4° C. (10 min). DIPEA (Diisopropylamine, 9 equiv) was then added into the mixture and stirred at room temperature for 1 h 30 min. Completion of the coupling was determined using Kaiser or a TNBS colorimetric test. After filtration, the resin was washed and the Fmoc removal procedure was again repeated. At the end of the synthetic sequences, the last free amine was capping by acetylation (Ac$_2$O/DIPEA/DMF 1:1:8, 1 h). After filtration, the solutions were drained off, the resin was dried under vacuum and the cleavage was carried out using trifluoroacetic acid/water/ethanedithiol/triisopropysilane (94.0/2.5/2.5/1.0) for 3 h. The resulting peptide was precipitated with methyl tert-butyl ether and isolated from the resin bead by centrifugation (20 min, 2000 rpm, 3×). The precipitates were dried carefully with a stream of air jet. The crude peptide was solubilised in H$_2$O to separate it from the resin. The solution was then lyophilized to afford desired peptide.

Purification of Tetanus Toxoid Monomer

Tetanus toxoid (TT) monomer was obtained by gel filtration chromatography before conjugation. One milliliter of a liquid preparation containing 4.5 mg/ml protein (as determined by the modified Lowry protein assay) was loaded onto a XK16-100 column filled with Superdex®200 Prep Grade (GE Healthcare Life Sciences, Uppsala, Sweden) equilibrated in PBS (20 mM NaHPO$_4$ [pH 7.2], 150 mM NaCl) and eluted with the same buffer. The protein eluted from the column in two peaks: the earlier-eluting peak contained oligomerized toxoid, and the later-eluting peak, corresponding to a Mr of 150,000, contained TT monomer. Fractions corresponding to the later (monomer) peak were pooled, desalted against deionized water, concentrated using a Centricon® Plus-70 centrifugal filter device (30K Ultracel PL membrane; Millipore, Billerica, Mass.), and then lyophilized.

HPLC Analysis of the Conjugates

HPLC analysis of the allyl neoglycoconjugate preparations was done by size exclusion chromatography. The chromatographic separation was performed with three 8-by 300-mm Shodex OHpak gel filtration columns connected in series (two SB-804 and one SB-803) preceded by a SB-807G guard column (Showa Denko). The neoglycoconjugate immunogens were eluted with 0.1 M NaNO$_3$ at a flow rate of 0.4 mL/min using a Knauer Smartline system equipped with a differential refractometer (RI) detector model 2300 and a UV detector model 2600 at wavelength of 280 nm. The conjugate preparation (8-mg/mL solution in the mobile phase) was injected using a 50-µA injection loop. In selected experiments, the fractions eluting at the void volume, which correspond to the conjugate fractions, were pooled, dialyzed against water Spectra/Por; Molecular weight cut-off (MWCO), 12,000 to 14,000 [Spectrum Laboratories]), and lyophilized. This corresponds to the 2:1 fractionated conjugate.

Example 2: Allyl 2-acetamido-3,6-di-O-pivaloyl-2-deoxy-α-D-glucopyranoside (Compound 2)

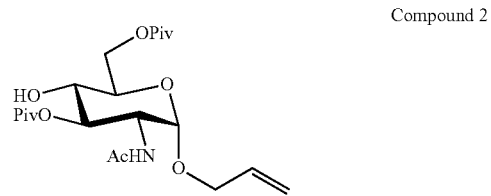

Compound 2

Figure 2:
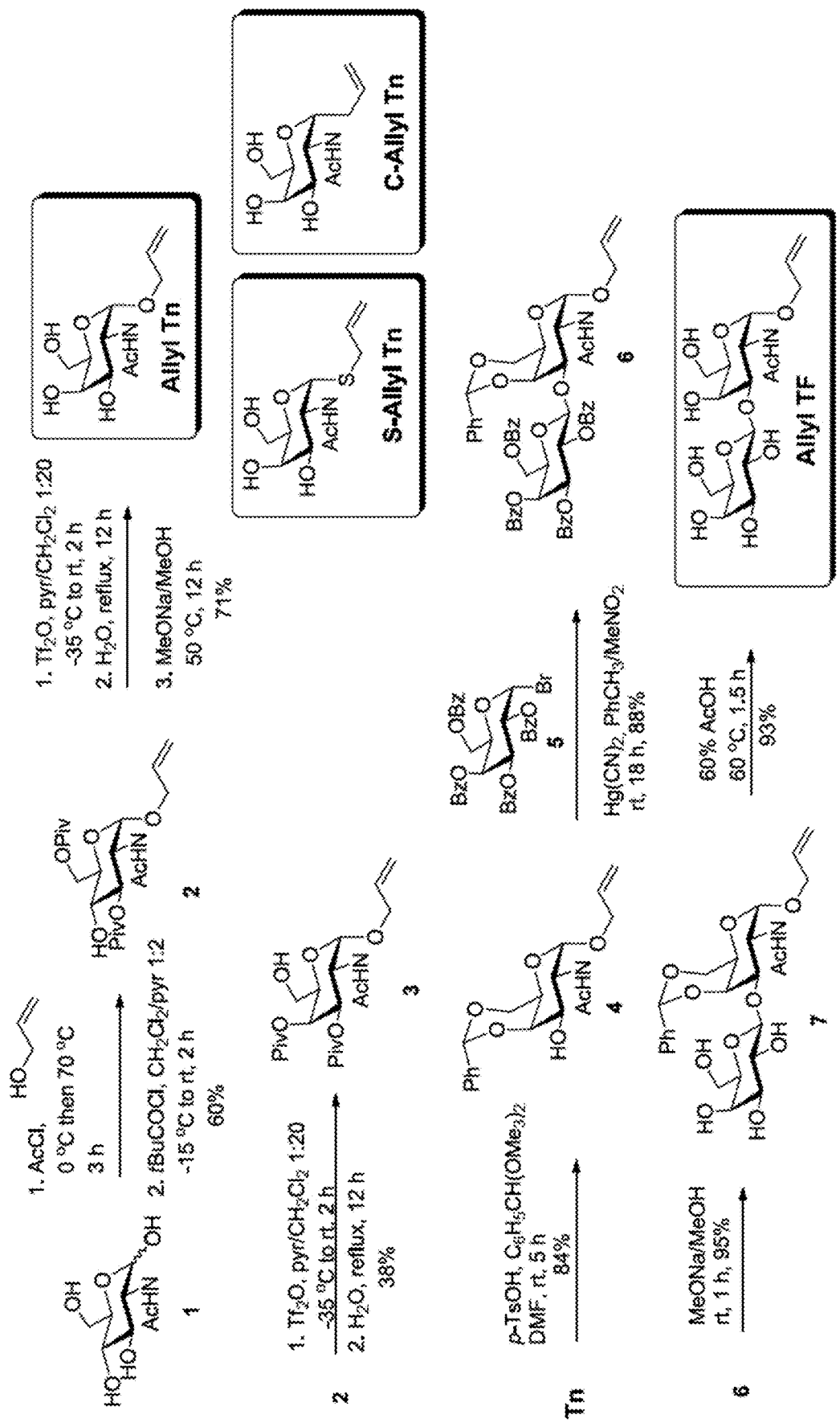
FIG. 2 shows reaction schemes for the syntheses of allyl Tn antigen and allyl TF antigen intermediates, as described in Examples 2-6.
Figure 3C:
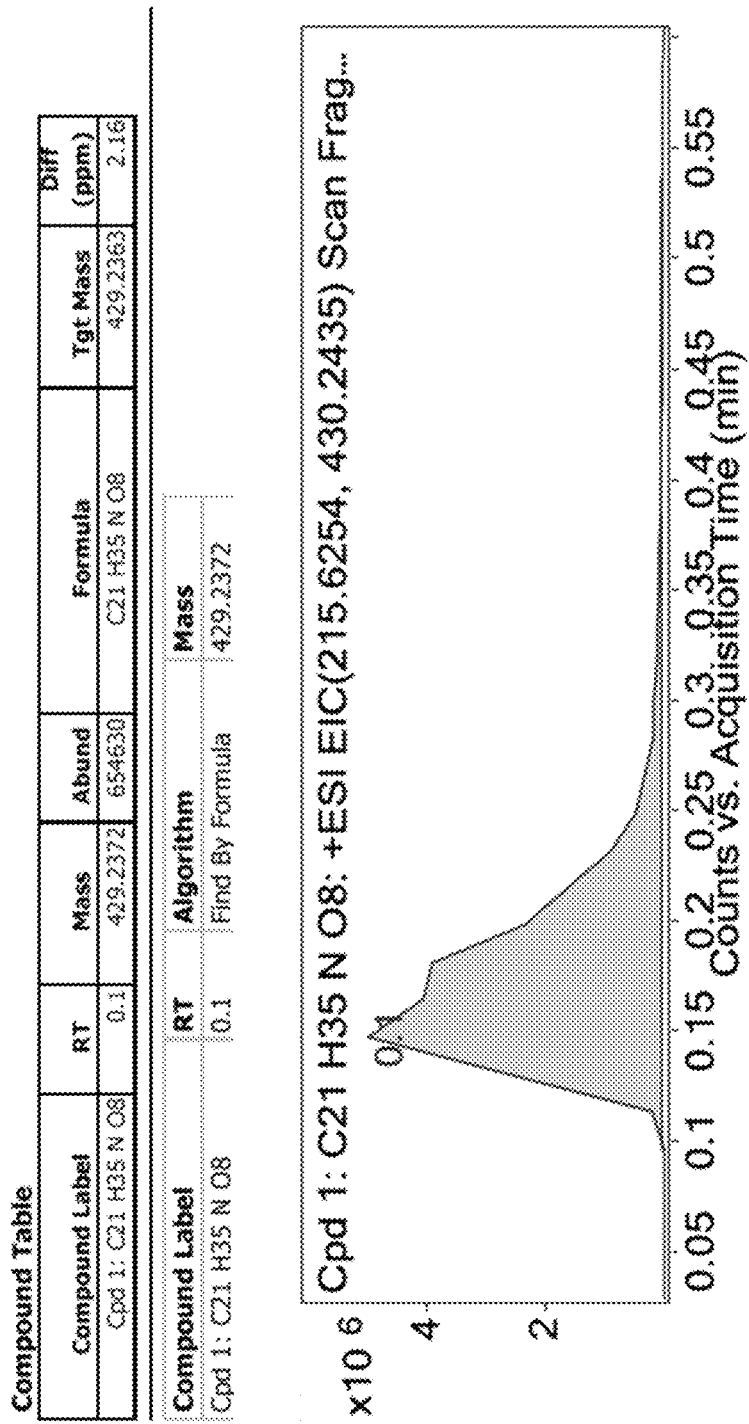
Figure 3D:
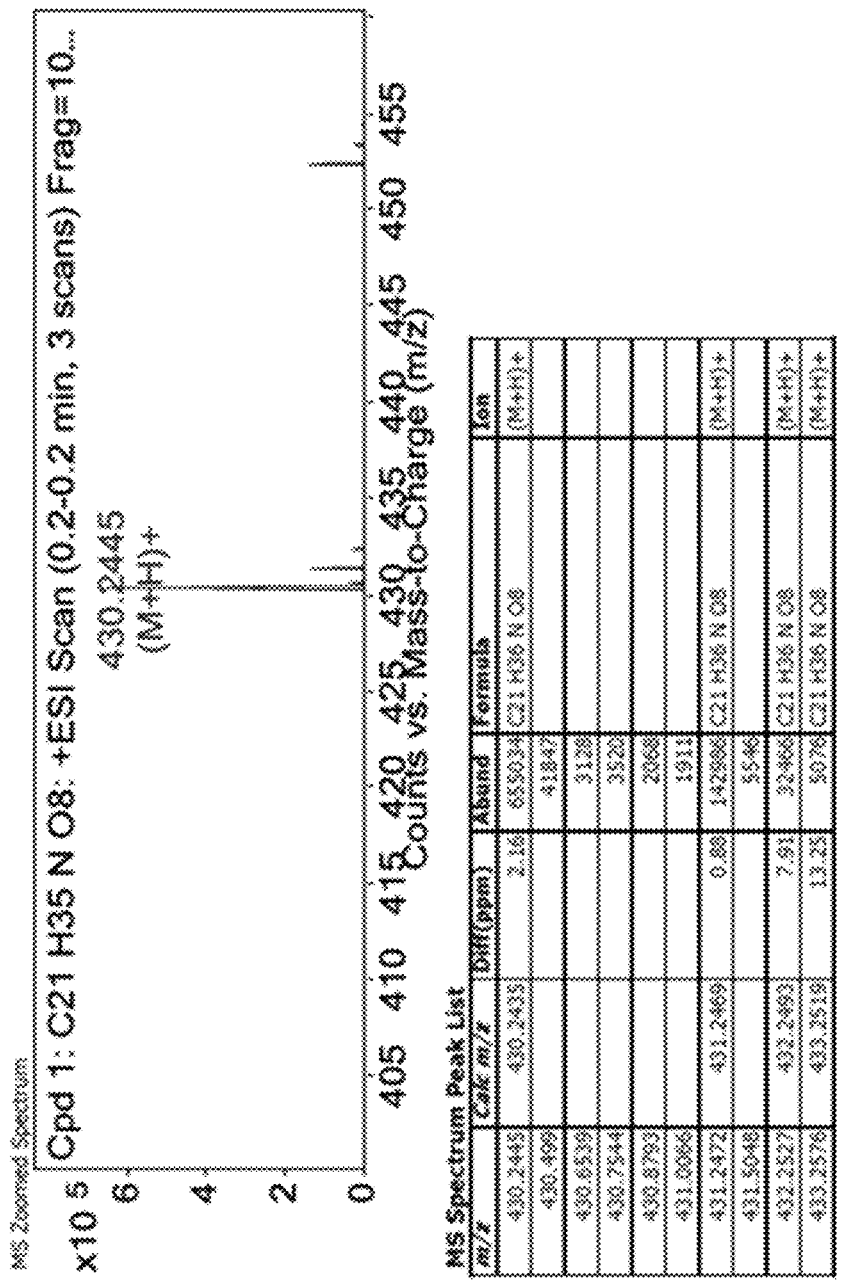

Referring to FIG. 2, acetyl chloride (2.76 mL, 38.80 mmol, 3.43 equiv.) was added dropwise to allylic alcohol (20.8 mL) at 0° C. under argon atmosphere. At room temperature, N-acetyl-D-glucosamine (Compound 1) (2.50 g, 11.3 mmol, 1.00 eq.) was added. The reaction mixture was stirred at 70° C. for 3 hours, then quenched by adding solid NaHCO$_3$ until pH 7. The suspension was filtered through out a pad of Celite, washing several times with MeOH. The solvent was removed under reduced pressure, and the crude allyl 2-acetamido-2-deoxy-D-glucosamine was precipitated by trituration with Et$_2$O/Ethanol. The solvent was then removed under reduced pressure several times after trituration. To a suspension of crude allyl 2-acetamido-2-deoxy-α-D-glucopyranoside intermediate, in the mixture of dry dichloromethane-pyridine (45 mL, v/v, 1:2) under nitrogen atmosphere at −15° C., pivaloyl chloride (3.90 mL, 31.64 mmol, 2.80 equiv.) was then added dropwise. The reaction mixture was stirred for 2 hours warned to room temperature to give the desired α-anomer (Compound 2) (Rf=0.32) together with some β-anomer (Rf=0.18); hexanes/EtOAc 1:1). The mixture was diluted then with CH$_2$Cl$_2$ and the organic phase was successively washed with HCl (1M) several times, saturated aqueous solution of KHSO$_4$, saturated solution of NaHCO$_3$, and brine. The organic phase was dried over Na$_2$SO$_4$, filtered and evaporated under reduced pressure. The yellowish oil was purified by flash chromatography on silica gel (Hexane-EtOAc 6:4 to 1:1) to afford the desired compound allyl 2-acetamido-3,6-di-O-pivaloyl-2-deoxy-α-D-glucopyranoside (Compound 2) as white solid (4.85 g, 6.78 mmol, 60%). Rf=0.32; hexanes/EtOAc 1:1;

FIGS. 3A & 3B: $^1$H NMR (CDCl$_3$, 600 MHz): δ 5.87 (dddd, 1H, J$_{H,H}$=16.8, 10.5, 6.2, 5.3 Hz, OCH$_2$CH=CH$_2$), 5.77 (d, 1H, J$_{NH,H2}$=9.7 Hz, NH), 5.31-5.25 (m, 1H, OCH$_2$CH=CH$_2$), 5.22 (dd, 1H, J$_{H,H}$=10.4, 1.3 Hz, OCH$_2$CH=CH$_2$), 5.09 (dd, 1H, J$_{3,4}$=10.7, J$_{2,3}$=9.3 Hz, H-3), 4.83 (d, 1H, J$_{1,2}$=3.7 Hz, H-1), 4.39 (m, 1H, H-6a), 4.35-4.25 (m, 2H, H-6b and H-2), 4.19 (m, 1H, OCH$_2$), 4.02-3.93 (m, 1H, OCH$_2$), 3.85 (m, 1H, H-5), 3.59-3.48 (m, 1H, H-2), 3.03 (d, 1H, J$_{4,OH}$=5.1 Hz, OH-4), 1.93 (s, 3H, NHCOCH$_3$), 1.23 (s, 9H, tert-Butyl) and 1.19 ppm (s, 9H, tert-Butyl); $^{13}$C NMR (CDCl$_3$, 150 MHz): δ 179.8, 179.1 (tert-BuCO), 169.7 (NHCO), 133.2 (OCH$_2$CH=CH$_2$), 118.1 (OCH$_2$CH=CH$_2$), 96.4 (C-1), 73.4 (C-3), 70.5 (C-5), 69.1 (C-4), 68.2 (OCH$_2$), 63.1 (C-6), 51.4 (C-2), 39.0, 38.9 (2× C(CH$_3$)$_3$), 27.2, 27.0 (2×C(CH$_3$)$_3$) and 23.2 ppm (CH$_3$). FIGS. 3C & 3D: ESI$^+$-HRMS: [M+H]$^+$ calcd for C$_{21}$H$_{36}$O$_8$N, 430.2435; found, 430.2445. The β-anomer was isolated as white solid (971 mg, 2.26 mmol, 20%). Rf=0.18; hexanes/EtOAc 1:1; $^1$H NMR (CDCl$_3$, 300 MHz): δ 6.00 (d, 1H, J$_{NH,H2}$=9.3 Hz, NH), 5.95-5.75 (m, 1H, OCH$_2$CH=CH$_2$), 5.35-5.03 (m, 3H, OCH$_2$CH=CH$_2$ and H-3), 4.55 (d, 1H, J$_{1,2}$=8.4 Hz, H-1), 4.47-425 (m, 3H, H-6a, 6b and OCH$_2$), 4.14-3.90 (m, 2H, OCH$_2$ and H-2), 3.65-3.43 (m, 2H, H-5 and H-4), 3.23 (sb, 1H, OH-4), 1.92 (s, 3H, NHCOCH$_3$), 1.23 (s, 9H, tert-Butyl) and 1.20 ppm (s, 9H, tert-Butyl).

Example 3: Allyl 2-acetamido-2-deoxy-α-D-galactopyranoside (Allyl Tn)

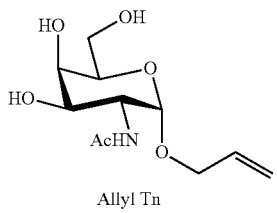

Allyl Tn

Figure 4C:
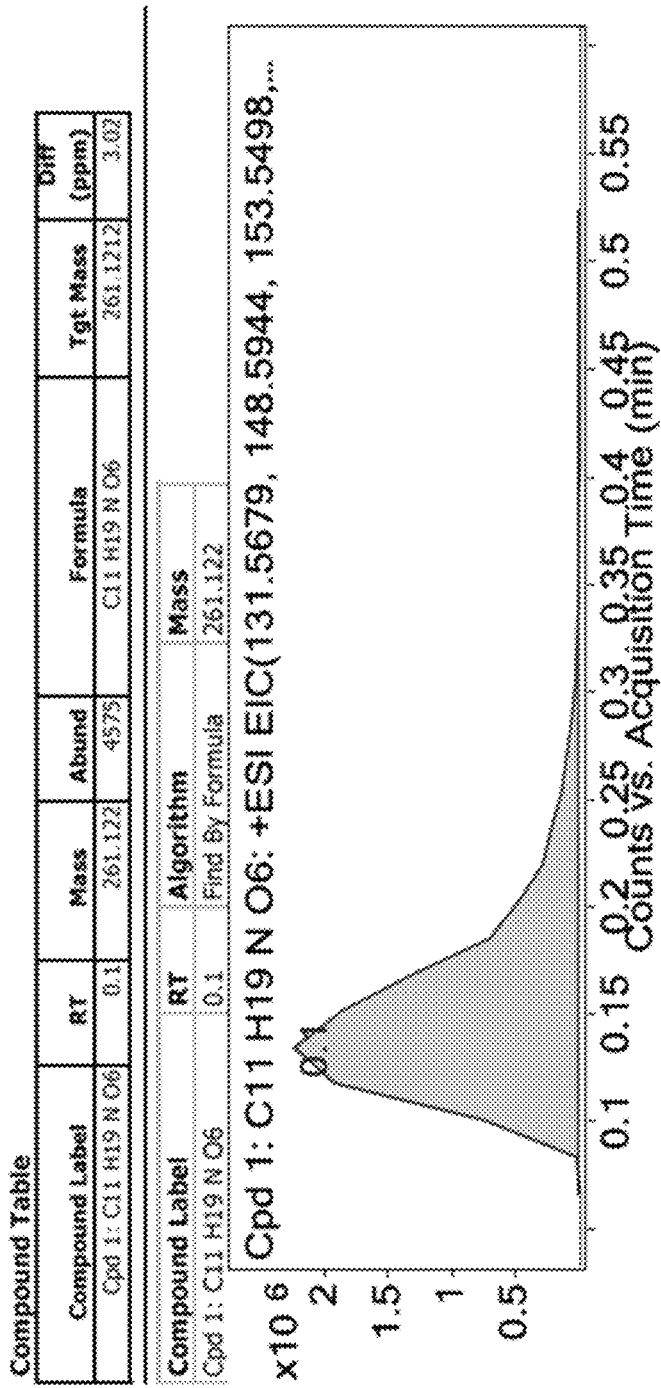
Figure 4D:
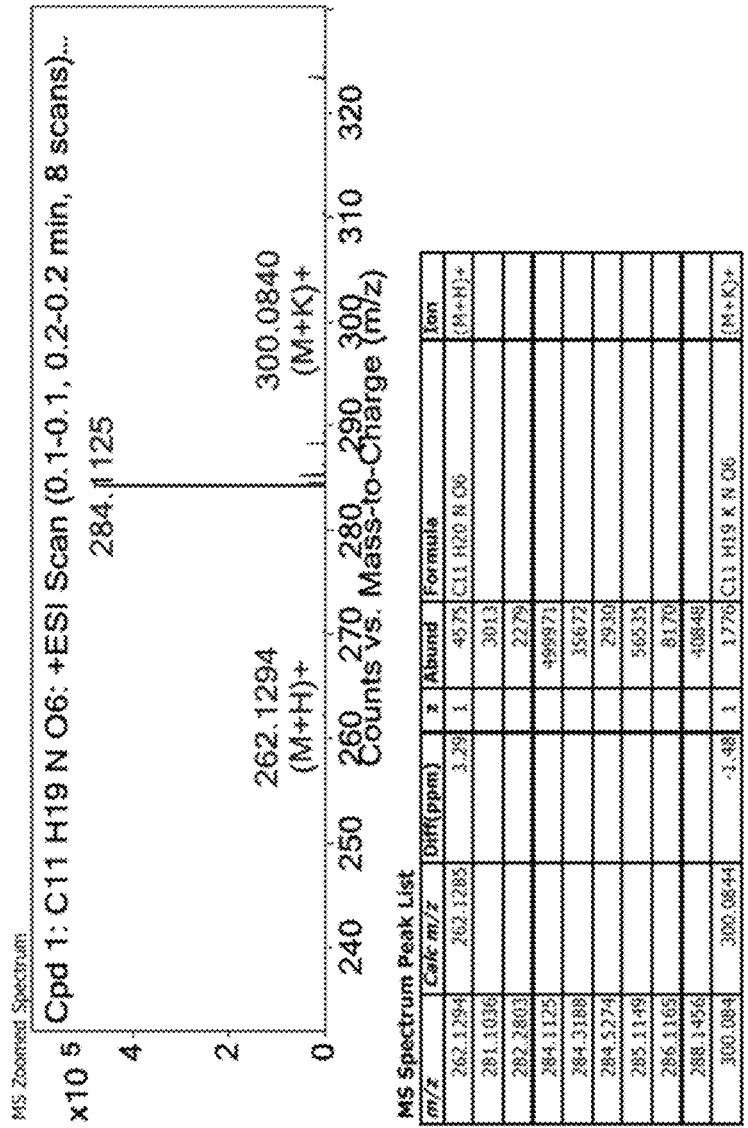

Referring to FIG. 2, di-O-pivaloyl compound (Compound 2) (5.50 g, 12.80 mmol, 1.0 equiv.) in a mixture of dry dichloromethane-pyridine (126 mL, v/v 20:1) was cooled to −35° C. under argon atmosphere. Trifluoromethanesulfonic anhydride (2.58 mL, 15.36 mmol, 1.2 equiv.) was then added and the mixture was stirred at this temperature. The temperature was warned to room temperature for 2 hours. Water (12 mL) was then added into the solution. The mixture was heated, and stirred at reflux (≈50° C.) overnight (12 hours). After reaching room temperature, the reaction mixture was diluted with dichloromethane and washed with 1M aqueous HCl several times. The organic layer was washed with H$_2$O, saturated NaHCO$_3$, and brine. The organic layer was dried over Na$_2$SO$_4$, filtered and evaporated under reduced pressure. The crude product was treated under Zemplén condition (1M sodium methoxide solution in methanol, 40 mL, pH 9). The solution was stirred at 50° C. overnight. After cooling to room temperature, the solution was neutralized by addition on ion-exchange resin (Amberlite® IR 120, H$^+$), filtered, washed with MeOH, and the solvent was removed under reduced pressure. Allyl T$_N$ was isolated by precipitation in MeOH/EtOAc/Hexanes as white solid after lyophilisation (2.36 g, 9.10 mmol, 71%). Rf=0.32; EtOAc/MeOH 4:1; FIGS. 4A & 4B: $^1$H NMR (CD$_3$OD, 600 MHz): δ 5.99-5.88 (m, 1H, OCH$_2$CH=CH$_2$), 5.31 (dd, 1H, J$_{trans}$=17.3, J$_{gem}$=1.3 Hz, OCH$_2$CH=CH$_2$), 5.17 (dd, 1H, J$_{cis}$=10.5 Hz, OCH$_2$CH=CH$_2$), 4.86 (d, 1H, J$_{1,2}$=3.8 Hz, H-1), 4.27 (dd, 1H, J$_{2,3}$=11.0 Hz, H-2), 4.20 (m, 1H, OCH$_2$), 4.00 (m, 1H, OCH$_2$), 3.89 (dd, J$_{3,4}$=J$_{4,5}$=2.6 Hz, H-4), 3.85-3.77 (m, 2H, H-3 and H-5), 3.72 (m, 2H, H-6a and H-6b) and 1.99 ppm (s, 3H, CH$_3$); $^{13}$C NMR (CD$_3$OD, 150 MHz): δ 172.5 (NHCO), 134.2 (OCH$_2$CH=CH$_2$), 116.1 (OCH$_2$CH=CH$_2$), 96.6 (C-1), 71.2 (C-3), 69.0 (C-4), 68.3 (C-5). 67.8 (OCH$_2$), 61.4 (C-6), 50.2 (C-2) and 21.2 ppm (CH$_3$). FIGS. 4C & 4D: ESI$^+$-HRMS: [M+H]$^+$ calcd for C$_{11}$H$_{20}$O$_6$N, 262.1285; found, 262.1294.

Procedure B: Allyl 2-acetamido-2-deoxy-α-D-galactopyranoside can also be directly prepared from N-acetylgalactosamine (GalNAc) according to literature procedure (Feng et al., 2004: To a solution of N-acetylgalactosamine (442 mg, 2 mmol, 1.0 equiv.) in allyl alcohol (8 mL) at room temperature was added BF$_3$.Et$_2$O (250 μL, 2 mmol, 1.0 equiv.), and the mixture was stirred at 70° C. for 2 hours. The solution was cooled to room temperature and the solvent was removed under reduced pressure. The dry crude product was dissolved in minimum EtOH (5 mL). The desire allyl TN product was precipitated in diisopropyl ether and isolated as white solid (417 mg, 1.60 mmol, 80%).

The C-Allyl GalNAc analog (FIG. 2) [1-(2'-Acetamido-2'-deoxy-α-D-galactopyranosyl)-2-propene] has been prepared according to literature procedure (Cipolla, et al., 2000: 3-(2-Acetamido-3,4,6-tri-O-acetyl-2-deoxy-α-D-galactopyranosyl)-1-propene (Cui et al., 1998) (371 mg, 1.00 mmol, 1.0 equiv.) was treated under Zemplén condition (1M sodium methoxide solution in methanol, 5 mL, pH 8-9). The solution was stirred at room temperature for 1 h. The reaction mixture was neutralized by addition on ion-exchange resin (Amberlite® IR 120, H$^+$), filtered, washed with MeOH, and the solvent was removed under reduced pressure. C-Allyl TN was purified by chromatography on silica gel (EtOAc/MeOH 9:1 to 4:1) followed by crystallisation in EtOH as white solid (213 mg, 0.87 mmol, 87%). Rf=0.28; EtOH 4:1; mp 230° C. (Litt. 215-217° C., EtOAc/EtOH); According to literature NMR data: $^1$H NMR (CD3OD, 600 MHz): δ 5.81 (m, 1H, $^1$CH$_2$CH=CH$_2$), 5.08 (dd, 1H, J$_{trans}$=17.2, J$_{gem}$=1.7 Hz, $^1_2$CH=CH$_2$), 5.02 (dd, 1H, J$_{cis}$=10.2 Hz, $^1$CH$_2$CH=CH$_2$), 4.22 (dd, 1H, J=9.3, 5.0 Hz, H-2'), 4.14 (dt, 1H, J=10.0, 5.0 Hz, H-1'), 3.91 (dd, 1H, J=3.0 Hz, H-4'), 3.82-3.64 (m, 4H, H-3', H-5' and H-6'ab), 2.45 (m, 1H, H-1a), 3.17 (m, 1H, H-1b) and 1.97 ppm (s, CH$_3$); $^{13}$C NMR (CD$_3$OD, 150 MHz): δ 173.6 (NHCO), 136.2 ($^1$CH$_2$CH=CH$_2$), 117.1 ($^1$CH$_2$CH=CH$_2$), 72.9 (C-1'), 69.7 (C-4'), 69.5 (C-3' and C-5'), 61.8 (C-6'), 52.0 (C-2'), 32.4 ($^1$CH$_2$) and 22.5 ppm (CH$_3$). ESI$^+$-LCMS: [M+H]$^+$ calcd for C$_{11}$H$_{20}$O$_5$N, 246.1336; found, 246.1332; CAN/H$_2$O 5 to 95% 1.4 min.

The S-Allyl GalNAc analog (FIG. 2) was prepared according to literature: Knapp et al., 2002.

Example 4: Allyl 2-acetamido-4,6-O-benzylidene-2-deoxy-α-D-galactopyranoside (Compound 4)

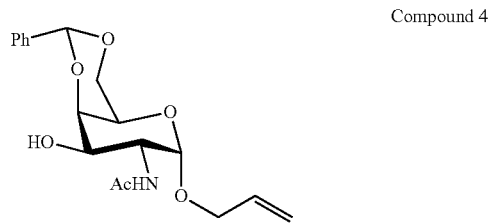

Compound 4

Figure 5A:
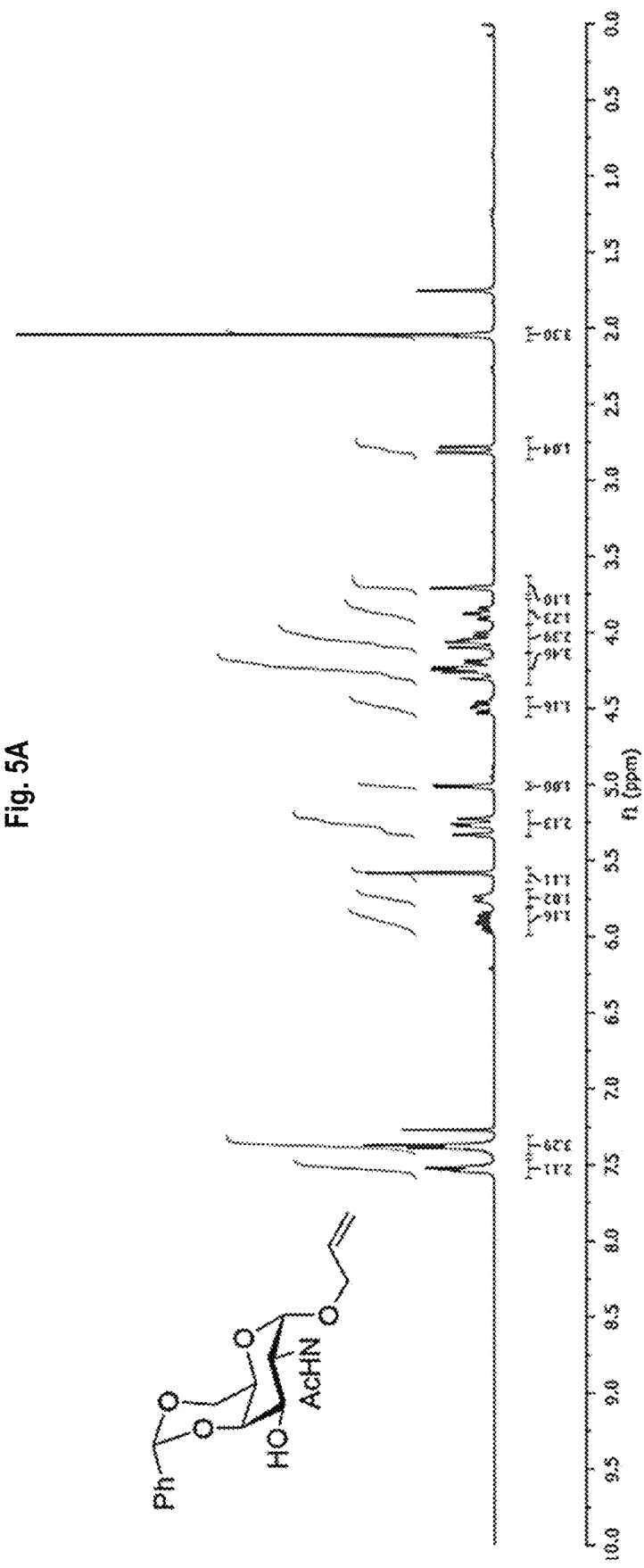
FIG. 5A-5C shows the $^1$H-NMR (FIG. 5A) spectra, as well as mass spectrometry results (FIGS. 5B & 6C) for allyl 2-acetamido-4,6-O-benzylidene-2-deoxy-α-D-galactopyranoside (Compound 4).
Figure 5B:
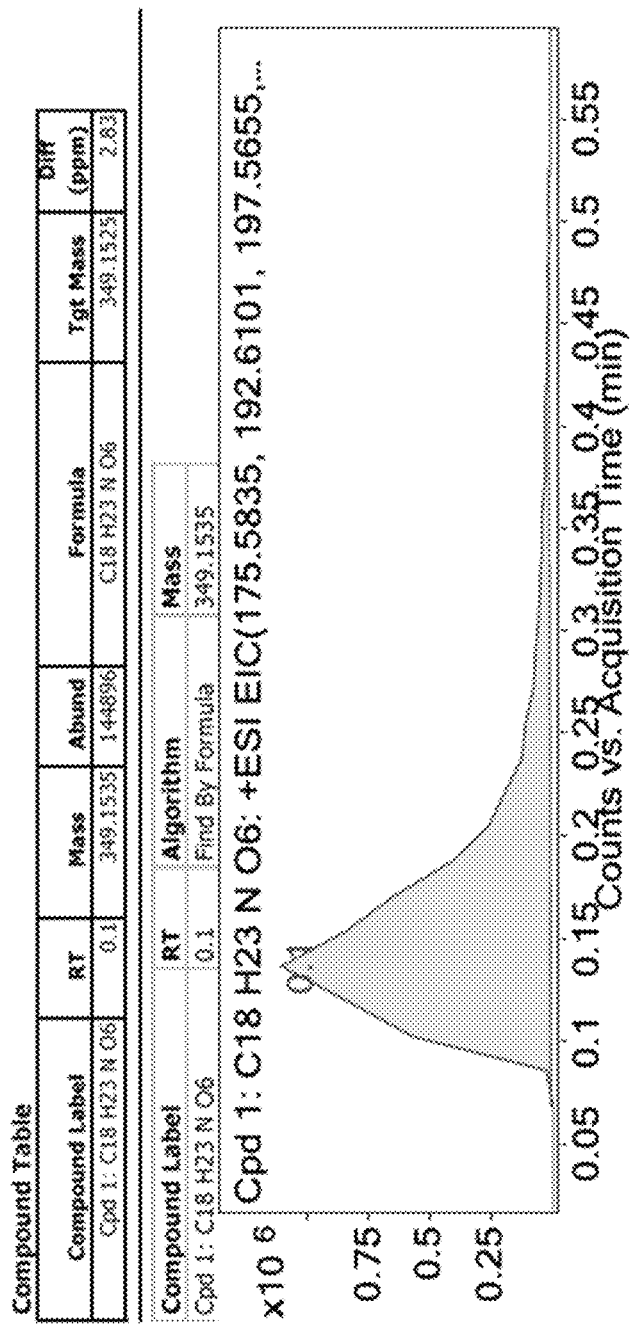
Figure 5C:
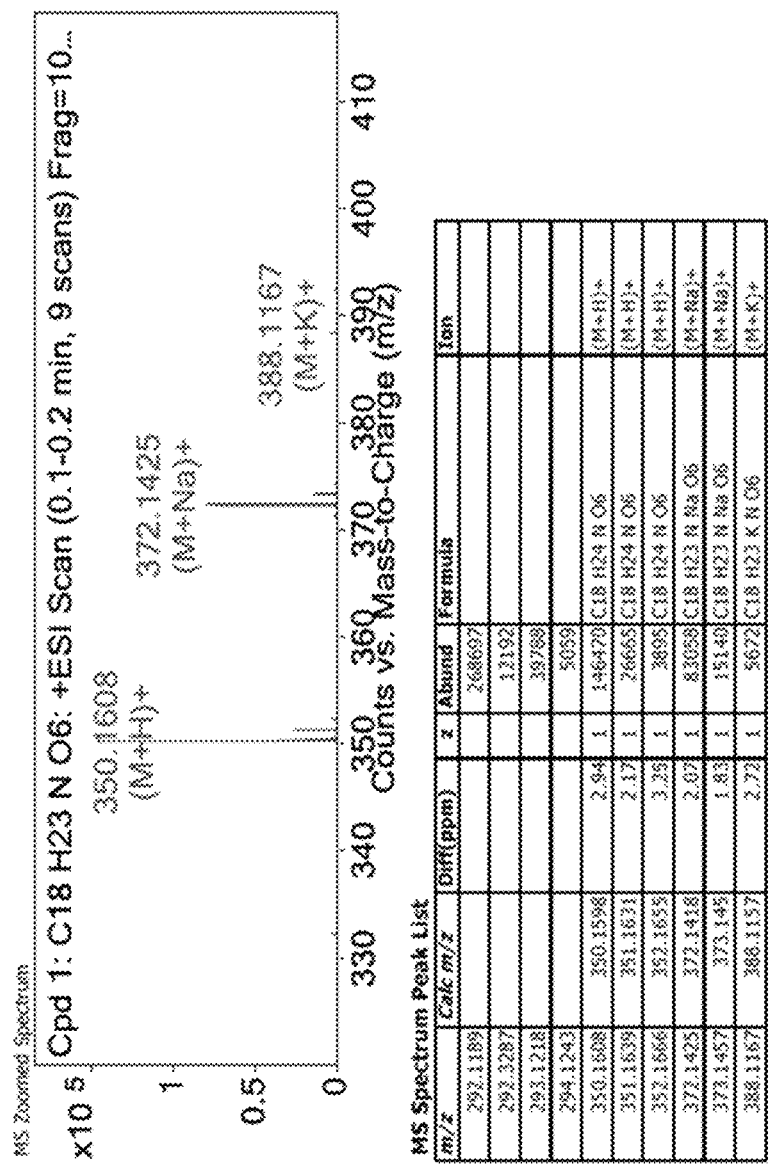

Referring to FIG. 2, to a solution of allyl GalNAc (Tn) (2.35 g, 9.0 mmol, 1.0 equiv.) and benzaldehyde dimethylacetal (6.75 mL, 45.0 mmol, 5.0 equiv.) in dry DMF (20 mL) was added a catalytic amount of p-toluenesulfonic acid monohydrate. The mixture was stirred at room temperature. After 5 hours, the mixture was diluted with $CHCl_3$ and washed with a saturated aqueous solution of $NaHCO_3$. The organic layer was separated and washed with water, dried over $Na_2SO_4$, and concentrated to afford white solid. The benzylidene acetal (compound 4) was isolated by precipitation in EtOAc/Hexanes as white solid (2.64 g, 7.56, 84%). Rf=0.21; DCM/MeOH 9.0:0.5; FIG. 5A: $^1H$ NMR ($CDCl_3$, 300 MHz): δ 7.59-7.46 (m, 2H, H-ar), 7.43-7.31 (m, 3H, H-ar), 5.91 (m, 1H, $OCH_2CH=CH_2$), 5.75 (d, 1H, $J_{NH,H2}$=9.0 Hz, NH), 5.58 (s, 1H, PhCH), 5.34-5.17 (m, 2H, $OCH_2CH=CH_2$), 5.01 (d, 1H, $J_{1,2}$=3.5 Hz, H-1), 4.56-4.42 (ddd, 1H, $J_{2,3}$=10.9 Hz, $J_{2,OH}$=9.1 Hz, H-2), 4.34 (dd, 1H, $J_{5,6a}$=1.5 Hz, $J_{6a,6b}$=12.5 Hz, H-6a), 4.19 (m, 2H, H-4 and $OCH_2$), 4.04 (m, 1H, dd, 1H, $J_{5,6b}$=1.6 Hz, $J_{6a,6b}$=12.5 Hz, H-6b), 4.01 (m, $OCH_2$), 3.86 (dd, 1H, $J_{3,4}$=10.9 Hz, H-3), 3.71 (sb, 1H, H-5), 2.80 (d, 1H, $J_{3,OH}$=10.7 Hz, OH-3) and 2.05 ppm (s, 3H, $CH_3$); FIGS. 5B & 5C: ESI$^+$-HRMS: [M+H]$^+$ calcd for $C_{18}H_{24}O_6N$, 350.1598; found, 350.1608.

Example 5: Allyl (2,3,4,6-tetra-O-benzol-β-D-galactopyranosyl)-(1→3)-2-acetamido-4,6-Q-benzylidene-2-deoxy-α-D-galactopyranoside (Compound 6)

Compound 6

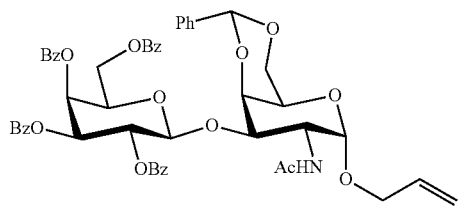

Figure 6A:
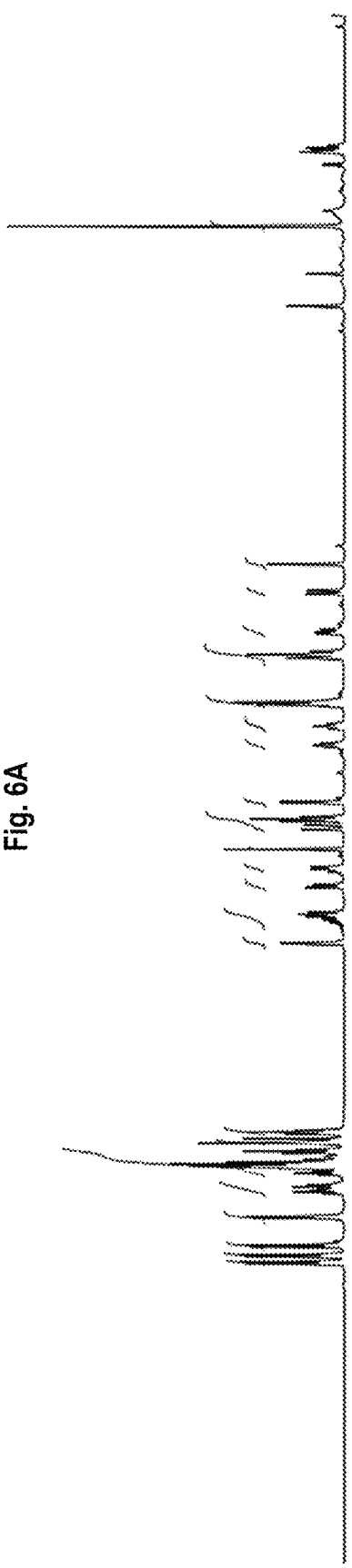
FIG. 6A-6D shows the $^1$H-NMR (FIG. 6A) and $^{13}$C-NMR (FIG. 6B) spectra, as well as mass spectrometry results (FIGS. 6C and 6D) for allyl (2,3,4,6-tetra-O-benzoyl-β-D-galactopyranosyl)-(1→3)-2-acetamido-4,6-O-benzylidene-2-deoxy-α-D-galactopyranoside (Compound 6).
Figure 6B:
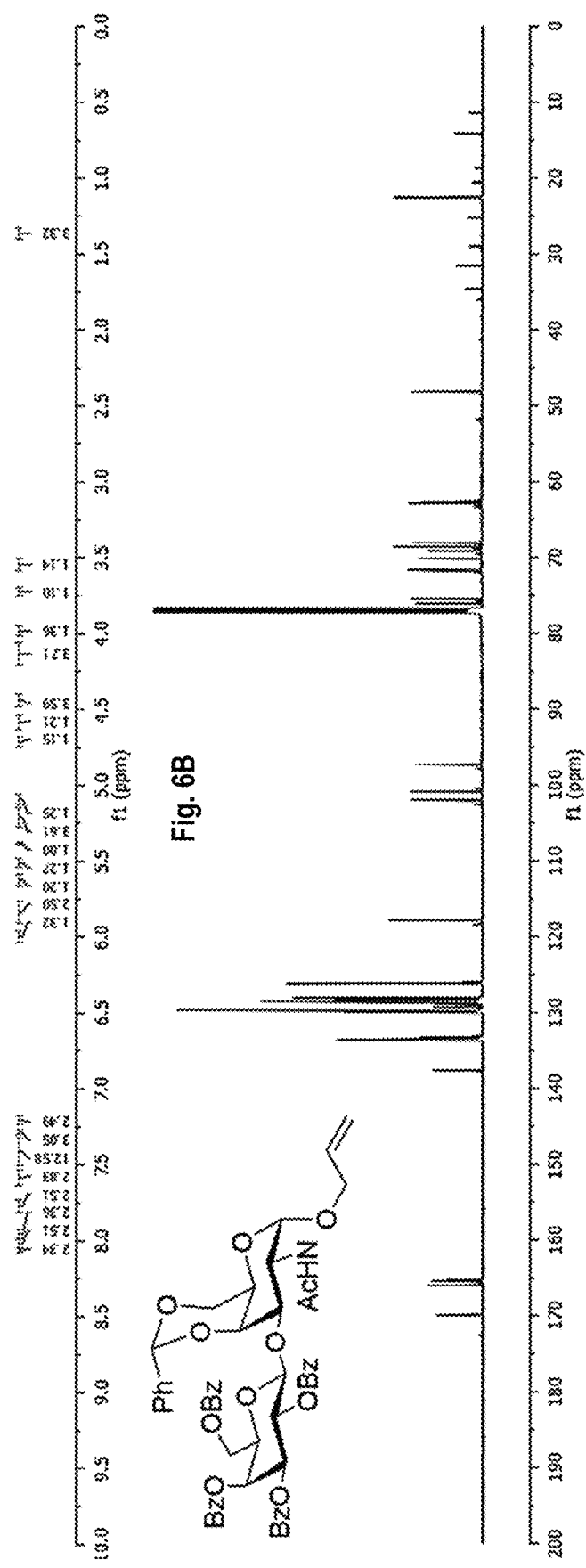
Figure 6C:
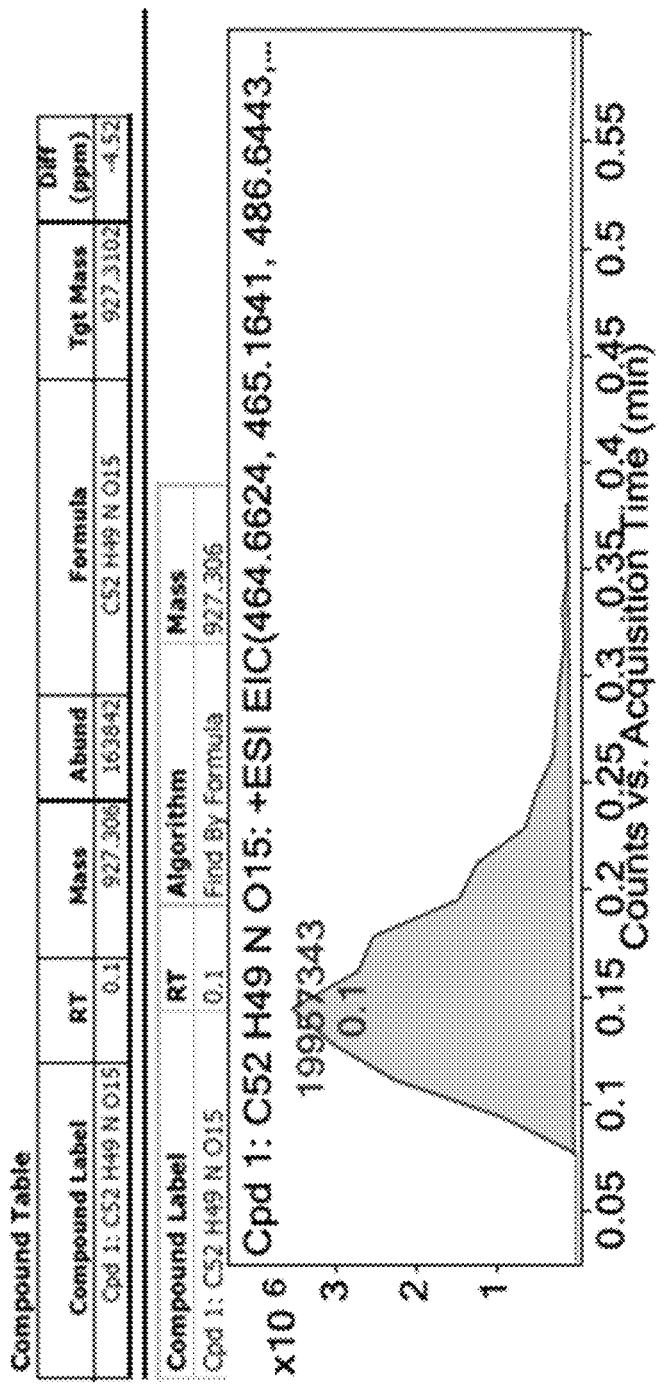
Figure 6D:
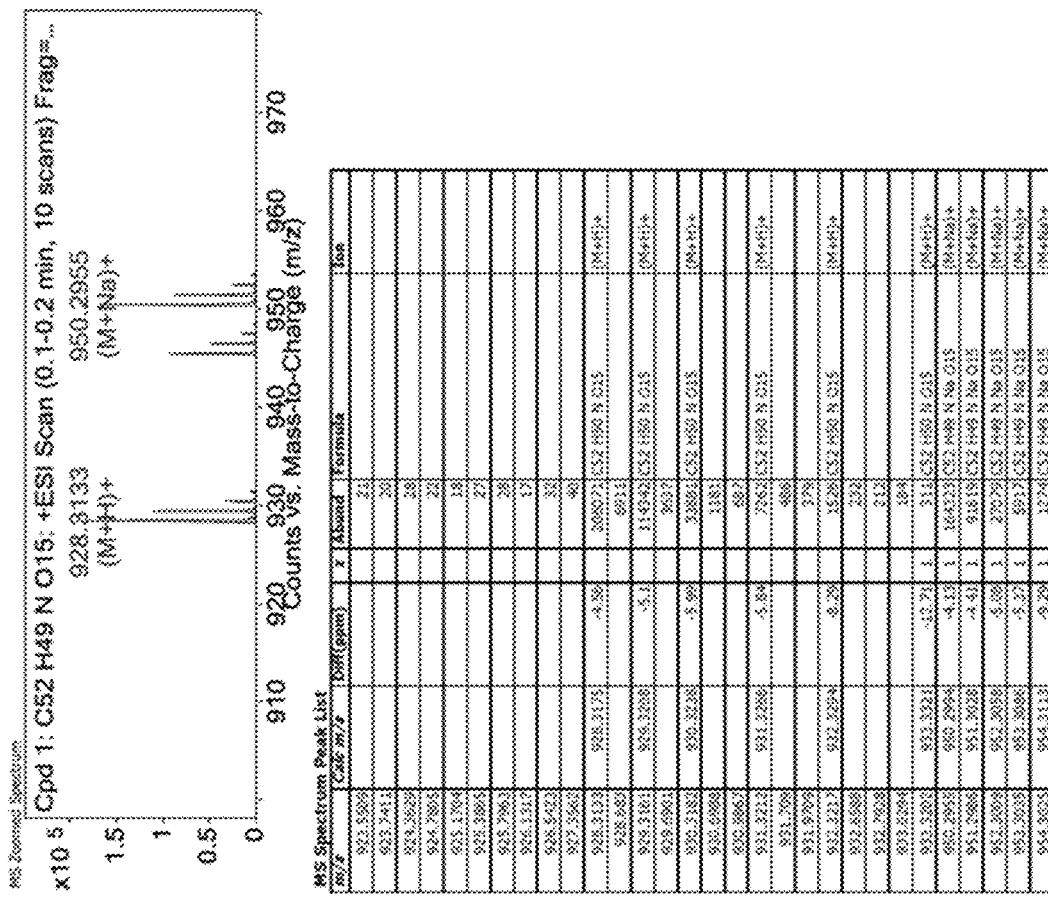

Referring to FIG. 2, Compound 4 (2.0 g, 5.72 mmol, 1.0 equiv.) and mercuric cyanide (2.17 g, 8.60 mmol, 1.5 equiv.) were dissolved in the mixture of anhydrous nitromethane-toluene (100 mL, 3:2, v/v) containing 4 Å molecular sieves under argon atmosphere. The mixture was stirred at room temperature for 30 min. 2,3,4,6-Tetra-O-benzoyl-α-D-galactopyranosyl bromide (Compound 5) (5.66 g, 8.58 mmol, 1.5 equiv.) was added into the mixture. The solution was stirred at 70° C. for five hours, then kept stirring at room temperature overnight (8 hours). After total consumption of the starting material (Compound 4) as indicated by TLC (DCM/MeOH 9.0:0.5), the solvent was removed under reduced pressure. The residue was dissolved in EtOAc followed by filtration through a celite pad. The filtrate was successively washed with 10% aqueous potassium iodide solution, saturated sodium hydrogen carbonate solution and water, then dried over $Na_2SO_4$. The solvent was evaporated under reduced pressure to afford a white foam. The crude product was purified by chromatography on silica gel using a gradient of 100% hexanes to hexanes/EtOAc 1:2 to afford the desired disaccharide (Compound 6) as white solid (4.98, 5.38 mmol, 94%). mp: 110-111° C., Rf=0.20; hexanes/EtOAc 1:2; FIGS. 6A & 6B: $^1H$ NMR ($CDCl_3$, 600 MHz): δ 8.06-7.19 (m, 5H, H-ar), 5.98 (dd, 1H, $J_{3,4}$=3.3 Hz, $J_{4,5}$=1.0 Hz, H-4$^{II}$), 5.85-5.78 (m, 2H, $OCH_2CH=CH_2$ and H-2$^{II}$), 5.60 (dd, 1H, $J_{2,3}$=10.2 Hz, $J_{3,4}$=3.4 Hz, H-3$^{II}$), 5.48 (sb, 1H, NH), 5.23 (m, 3H, $OCH_2CH=CH_2$ and H-1), 4.68 (dd, 1H, $J_{5',6a}$=6.9 Hz, $J_{6a',6b}$=11.4 Hz, H-6a$^I$), 4.63-4.58 (m, 1H, H-2), 4.46-4.36 (m, 3H, H-4, H-5 and H-6b$^{II}$), 4.14-4.07 (m, 3H, H-6a, $OCH_2$ and H-3), 3.96 (m, 1H, $OCH_2$), 3.75 (m, 1H, H-6b), 3.51 (m, 1H, H-5) and 1.40 ppm (s, 3H, $CH_3$); $^{13}C$ NMR ($CDCl_3$, 150 MHz): δ 170.0 (NHCO), 166.0, 165.5, 165.4, 165.2 (CO), 137.6-126.2 (multi, 30 C-arom), 133.2 ($OCH_2CH=CH_2$), 117.8 ($OCH_2CH=CH_2$), 102.0 (C-1$^{II}$), 100.9 (CPhCH), 97.3 (C-1$^I$), 76.1 (C-3), 75.4 (C-4), 71.7 (C-3$^{II}$ and C-5$^{II}$), 70.2 (C-2$^{II}$), 69.1 (C-6), 68.6 ($OCH_2$), 68.1 (C-4$^{II}$), 62.9 (C-5), 62.6 (C-6$^I$), 48.2 (C-2) and 22.5 ppm ($CH_3$). FIGS. 6C & 6D: ESI$^+$-HRMS: [M+H]$^+$ calcd for $C_{52}H_{50}O_{15}N$, 928.3175; found, 928.3133.

Example 6: Allyl (β-D-galactopyranosyl)-(1→3)-2-acetamido-2-deoxy-α-D-galactopyranoside (Allyl TF)

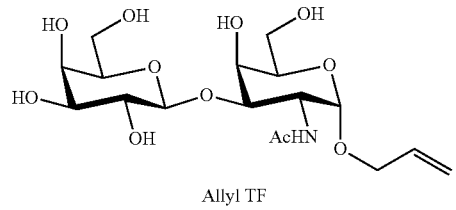

Allyl TF

Referring to FIG. 2, a solution of compound 6 (1.12 g, 1.20 mmol, 1.0 equiv.) in 1M sodium methoxide in methanol (12 mL, pH 8-9) was stirred at room temperature until consumption of starting material. After 1 h 30 min, the solution was neutralized by the addition of ion-exchange resin (Amberlite IR 120, H$^+$), filtered, washed with MeOH, and the solution was suspended with silica gel, filtered, and the solvent removed under reduced pressure. The silica gel was washed with 100% EtOAc several times followed by washing with second solution (EtOAc/MeOH/$H_2O$ 1:1:0.1). The combined filtrate was evaporated under reduced pressure to afford the intermediate (Compound 7) as white solid. Rf=0.20; $CHCl_3$/MeOH/$H_2O$ 11:6:1; FIGS. 7A & 7B: $^1H$ NMR ($D_2O$, 600 MHz): δ 7.47-7.39 (m, 2H, H-ar), 7.37-7.26 (m, 3H, H-ar), 5.82 (m, 1H, $OCH_2CH=CH_2$), 5.61 (s, 1H, PhCH), 5.20-5.09 (m, 2H, $OCH_2CH=CH_2$), 4.88 (d, 1H, $J_{1,2}$=3.4 Hz, H-1), 4.47 (dd, H-4), 4.37-4.25 (m, 2H, H-2 and H-1$^{II}$), 4.13-3.98 (m, 4H, H-3, H-6a, H-6b, $OCH_2$), 3.96-3.88 (m, 1H, H-5), 4.56-4.42 (ddd, 1H, $J_{2,3}$=10.9 Hz, $J_{2,OH}$=9.1 Hz, H-2), 4.34 (dd, 1H, $J_{5,6a}$=1.5 Hz, $J_{6a,6b}$=12.5 Hz, H-6a), 4.19 (m, 2H, H-4 and $OCH_2$), 4.04 (m, 1H, dd, 1H, $J_{5,6b}$=1.6 Hz, $J_{6a,6b}$=12.5 Hz, H-6b), 4.01 (m, $OCH_2$), 3.86 (dd, 1H, $J_{3,4}$=10.9 Hz, H-3), 3.71 (sb, 1H, H-5), 2.80 (d, 1H, $J_{3,OH}$=10.7 Hz, OH-3) and 2.05 ppm (s, 3H, $CH_3$); 3.83 (s, 1H, $OCH_2$), 3.72 (d, 1H, $J_{3',4'}$=$J_{4',5'}$=3.2 Hz, H-4$^{II}$), 3.65-3.55 (m, 2H, H-6a,b), 3.49, (m, 1H, H-5$^{II}$), 3.43 (dd, 1H, $J_{2',3'}$=10.0 Hz, $J_{3',4'}$=3.3 Hz, H-3$^{II}$), 3.33-3.24 (m, 1H, H-2$^{II}$) and 1.86 ppm (s, 3H, $CH_3$); $^{13}C$ NMR ($D_2O$, 150 MHz): δ 174.6 (NHCO), 136.8 (C-arom), 133.6 ($OCH_2CH=CH_2$), 129.9, 128.7, 126.5 (C-arom), 118.0 ($OCH_2CH=CH_2$), 104.9 (C-1$^{II}$), 101.3 (CHPh), 97.0 (C-1), 76.0 (C-4), 75.0 (C-3), 75.0 (C-5$^{II}$), 72.4 (C-3$^{II}$), 70.4 (C-2$^{II}$), 69.0 (C-6), 68.7 ($OCH_2CH=CH_2$), 68.6 (C-4$^{II}$), 63.0 (C-5), 61.0 (C-6$^{II}$), 48.6 (C-2) and 22.0 ppm ($CH_3$). Rf=0.38; EtOAc/MeOH/$H_2O$ 7:3:0.1; Rf=0.46; ACN/

Figure 7D:
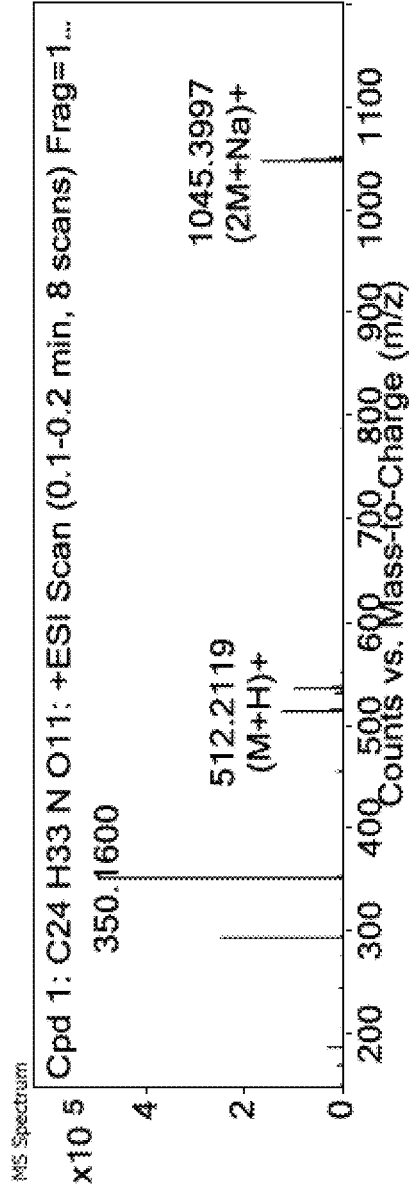

MeOH/H$_2$O 7:2:1. FIGS. 7C & 7D: ESI$^+$-HRMS: [M+H]$^+$ calcd for C$_{24}$H$_{34}$O$_{11}$N, 512.2126; found, 512.2119.

Figure 8A:
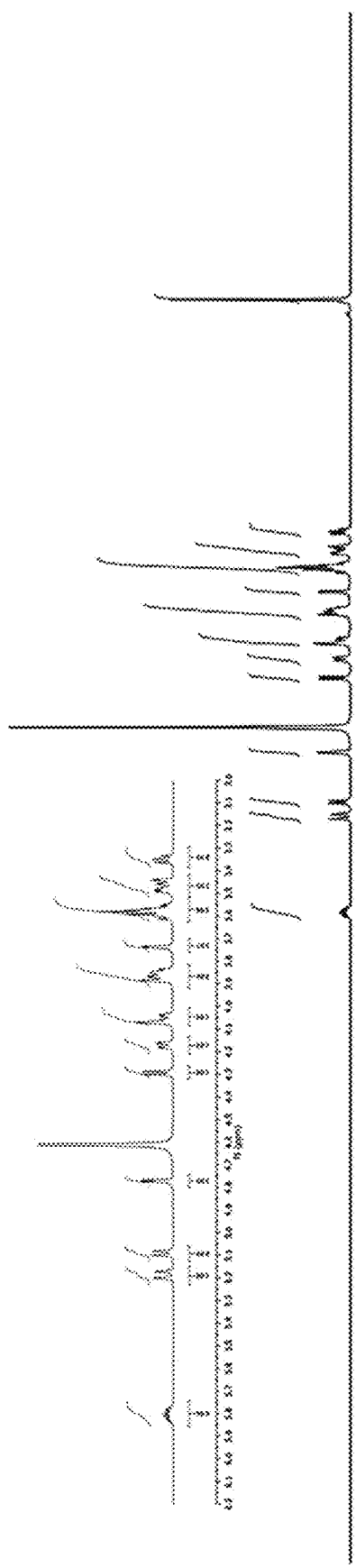
FIG. 8A-8D shows the $^1$H-NMR (FIG. 8A) and $^{13}$C-NMR (FIG. 8B) spectra, as well as mass spectrometry results (FIGS. 8C and 8D) for allyl (β-D-galactopyranosyl)-(1→3)-2-acetamido-2-deoxy-α-D-galactopyranoside (allyl TF).
Figure 8B:
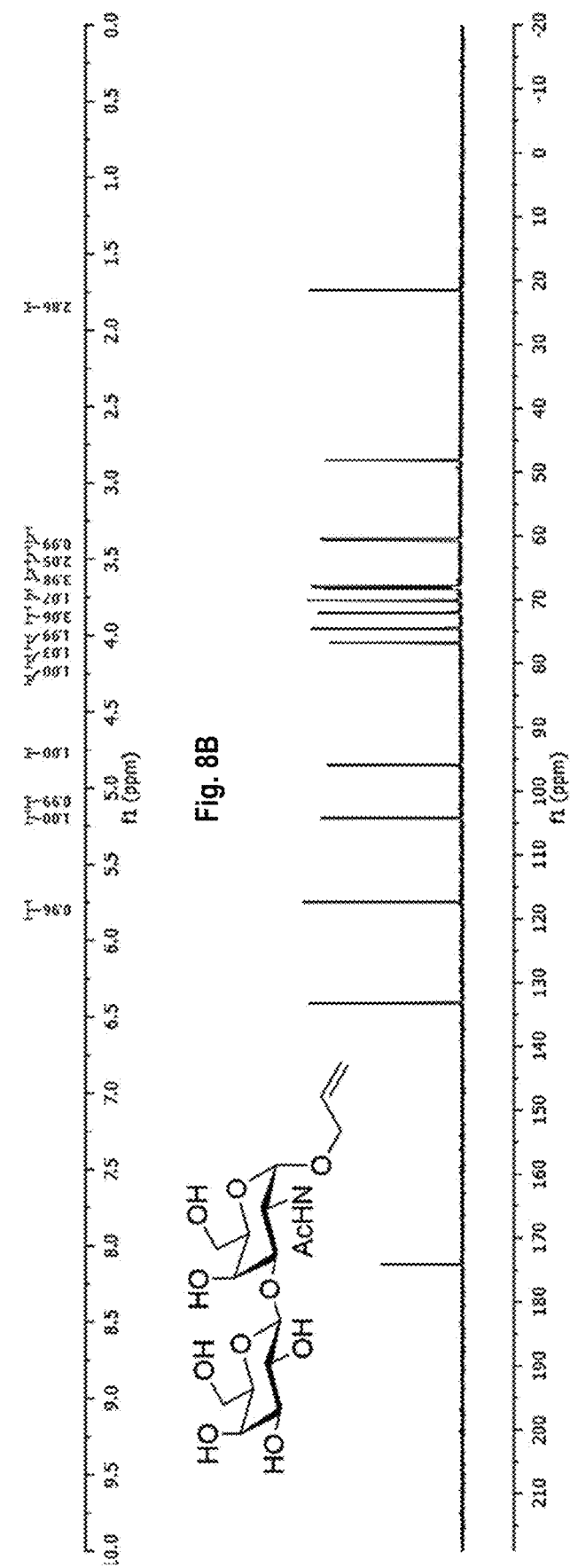
Figure 8C:
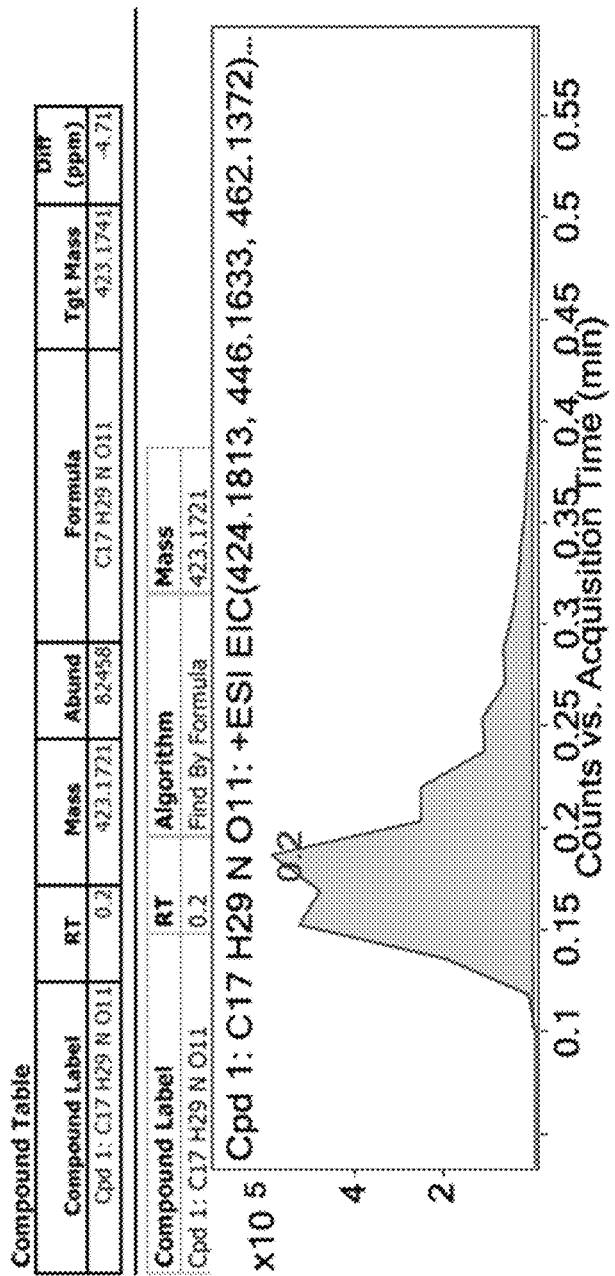
Figure 8D:
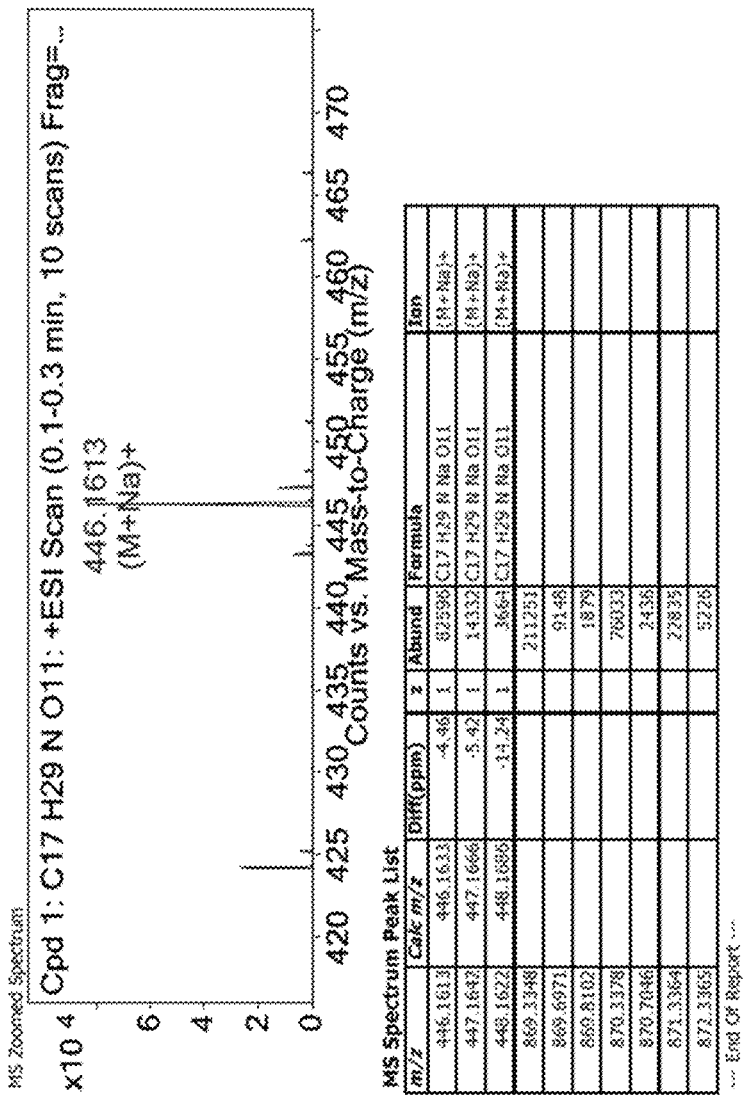

The white solid intermediate was then dissolved in 10 mL of 60% aqueous acetic acid and the resulting solution was stirred at 60° C. for 1.5 hours. The solvent was removed under reduced pressure, and the residue was lyophilized to afford the final allyl TF as white solid (427 mg, 1.0 mmol, 84%). mp=230-232° C.; Rf=0.53; CHCl$_3$/MeOH/H$_2$O 11:6:1; FIGS. 8A & 8B: $^1$H NMR (D$_2$O, 600 MHz): δ 5.80 (m, 1H, OCH$_2$CH=CH$_2$), 5.19 (dd, 1H, J$_{trans}$=17.3 Hz, OCH$_2$CH=CH$_2$), 5.09 (dd, 1H, J$_{cis}$=10.4 Hz, OCH$_2$CH=CH$_2$), 4.77 (d, 1H, J$_{1,2}$=3.7 Hz, H-1), 4.29 (d, 1H, J$_{1,2}$=3.7 Hz, H-1), 4.29 (d, 1H, J$_{1,2}$=7.8 Hz, H-1$^{II}$), 4.16 (dd, 1H, J$_{2,3}$=11.2 Hz, J$_{1,2}$=3.7 Hz, H-2), 4.08-4.01 (m, 2H, H-4 and OCH$_2$), 3.92-3.82 (m, 3H, H-3, H-5 and OCH$_2$), 3.73 (dd, 1H, H-4$^{II}$), 3.63-3.52 (m, 4H, H-6a,b and H-6'a,b), 3.47 (m, 2H, H-3$^{II}$ and H-5$^{II}$), 3.39 (dd, 1H, J$_{2',3'}$=10.0 Hz, J$_{1',2'}$=7.7 Hz, H-2$^{II}$) and 1.85 ppm (s, 3H, CH$_3$); $^{13}$C NMR (150 MHz, CDC$_{l3}$): δ 174.6 (NHCO), 133.7 (OCH$_2$CH=CH$_2$), 117.9 (OCH$_2$CH=CH$_2$), 104.7 (C-1$^{II}$), 96.4 (C-1), 77.2 (C-3), 75.0 (C-5$^{II}$), 72.5 (C-3$^{II}$), 70.7 (C-5), 70.6 (C-2$^{II}$), 68.8 (C-4), 68.6 (C-4$^{II}$), 68.4 (OCH$_2$), 61.2 (C-6$^{II}$), 61.0 (C-6), 48.6 (C-2) and 22.0 ppm (CH$_3$). FIGS. 8C & 8D: ESI$^+$-HRMS: [M+Na]$^+$ calcd for C$_{11}$H$_{29}$O$_{11}$NNa, 446.1633; found, 446.1613.

Example 7: 3-{[3-(2-acetamido-2-deoxy-α-D-galactopyranosyl)oxypropyl]thio}propanoic acid (Compound 8)

Compound 8

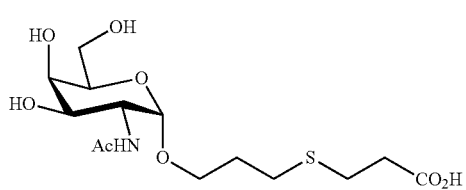

Figure 9:
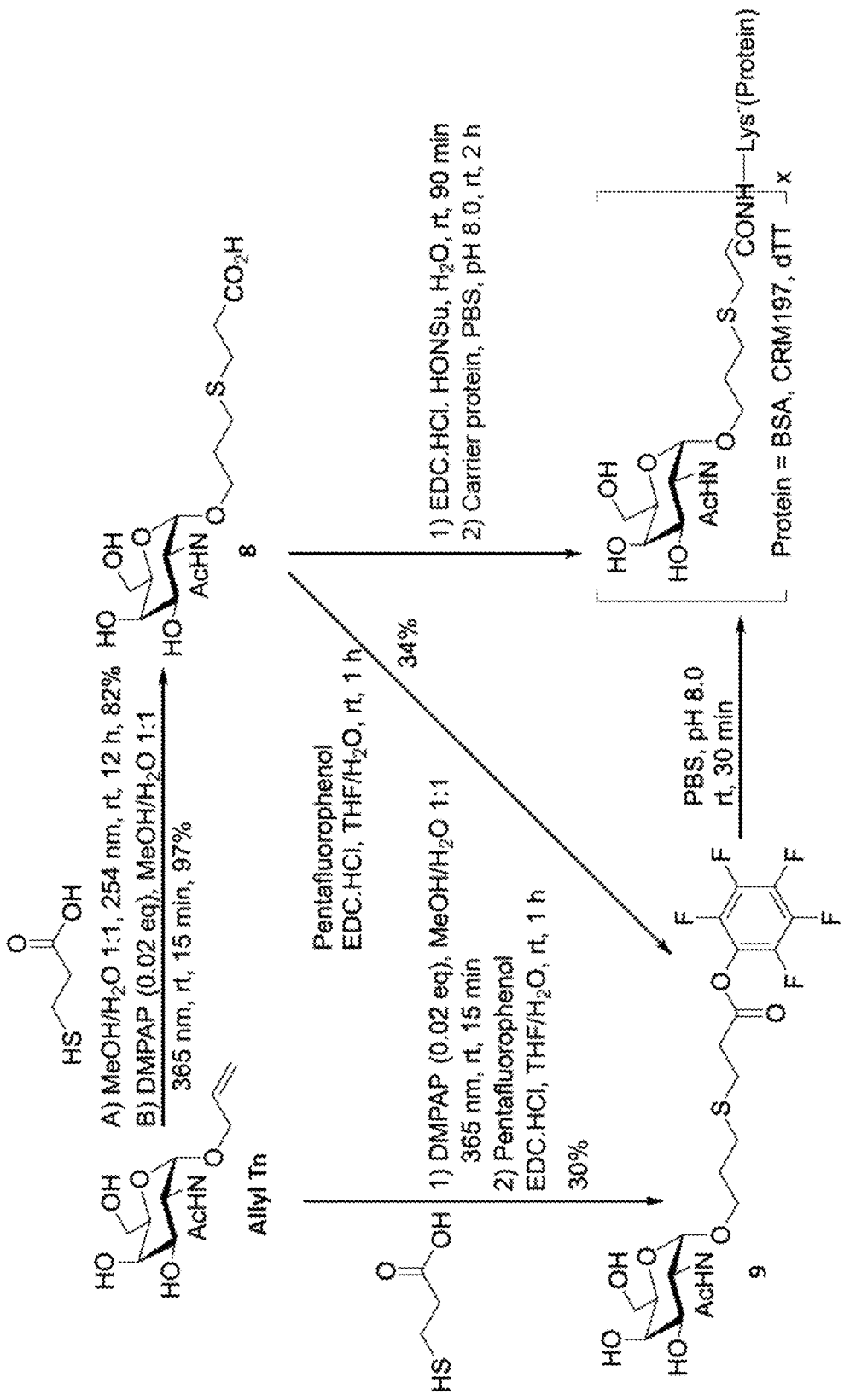
FIG. 9 shows reaction schemes for the production of neoglycoconjugate immunogens from Allyl Tn.
Figure 10:
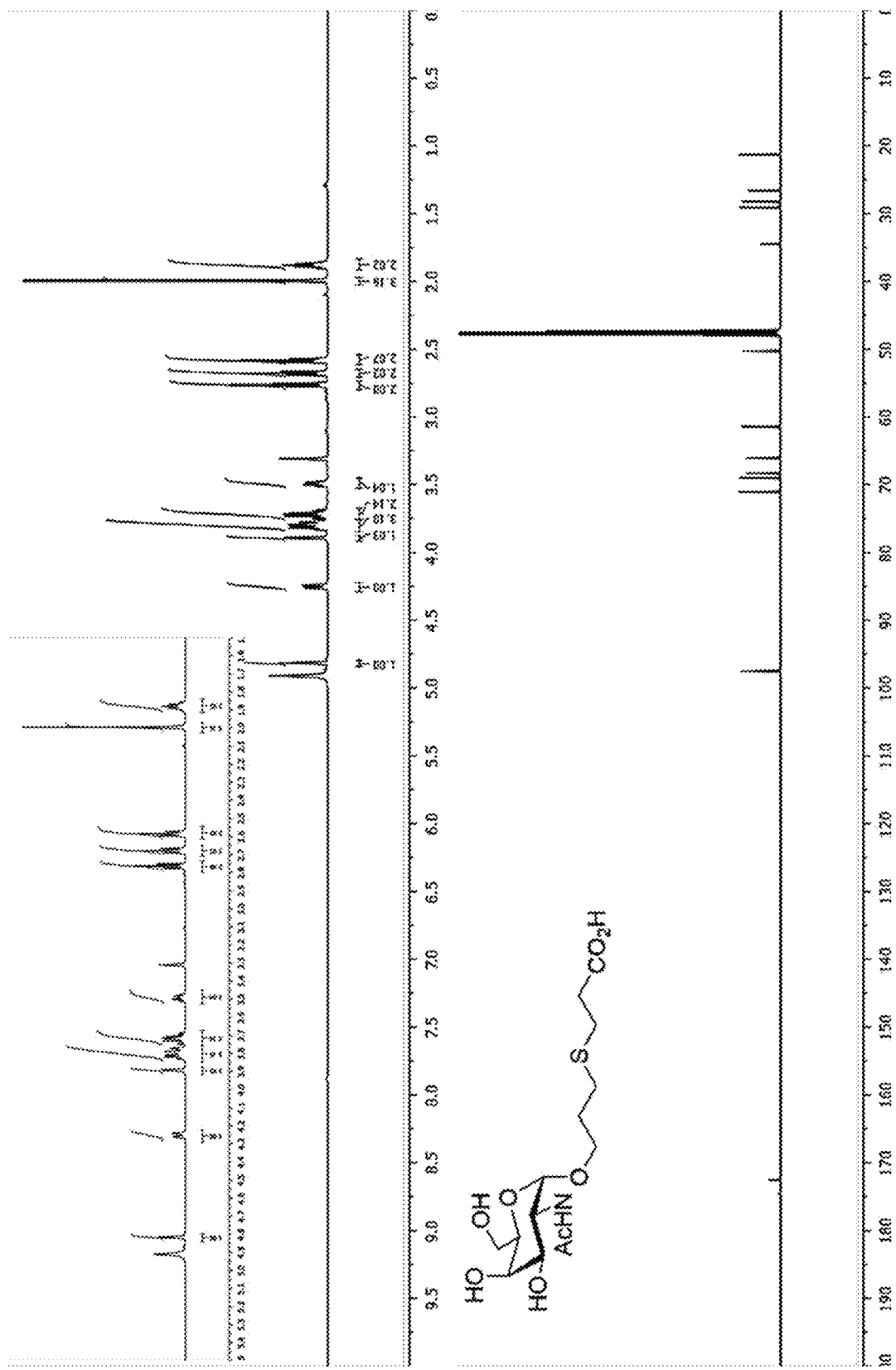
FIG. 10 shows the $^1$H-NMR and $^{13}$C-NMR spectra results for Compound 8.

Referring to FIG. 9, the solution of allyl Tn (392 mg, 1.50 mmol, 1.0 equiv.) and 3-mercaptopropionic acid (392 μL, 4.50 mmol, 3.0 equiv.) in H$_2$O/MeOH degassed (3 mL, 1:1, v/v), was stirred at room temperature under irradiation at 254 nm overnight (A) or with DMPAP (23 mg, 0.03 mmol, 0.06 equiv.) under 365 nm for 15 min (B). The mixture was then concentrated under reduced pressure with silica gel, then purified by flash chromatography on silica gel by gradient (EtOAc 100% to EtOAc/MeOH/AcOH 3:1:0.01) to afford the desired compound 8 as white foam (from A: 536 mg, 1.46 mmol, 97%); (from B: 82%). Rf=0.34; EtOAc/MeOH/AcOH 3:1:0.01; $^1$H NMR (CD$_3$OD, 600 MHz): δ 4.82 (d, 1H, J=3.7 Hz, H-1), 4.25 (dd, 1H, J=11.0, 3.7 Hz, H-2), 3.89 (d, 1H, J=3.2 Hz, H-4), 3.85-3.72 (m, 5H, H-3, H-5, H-6a, H-6b, OCH$_2$), 3.49 (dt, 1H, J=10.0, 6.0 Hz, OCH$_2$), 2.77 (t, 2H, J=7.1 Hz, CH$_2$), 2.68 (t, 2H, J=7.2 Hz, CH$_2$), 2.58 (t, 2H, J=7.1 Hz, CH$_2$), 2.00 (s, 3H, CH$_3$), 1.95-1.83 (m, 2H, CH$_2$); $^{13}$C NMR (CD$_3$OD, 150 MHz): δ 174.6 (NHCO), 172.5 (CO), 97.5 (C-1), 71.1 (C-3), 69.0 (C-4), 68.3 (C-5), 66.1 (OCH$_2$), 61.4 (C-6), 50.3 (C-2), 34.5, 29.1, 28.3, 26.6 (4×CH$_2$) and 21.3 ppm (CH$_3$). ESI$^+$-HRMS: [M+H]$^+$ calcd for C$_{14}$H$_{26}$O$_8$NS, 368.1374; found, 368.1377. (FIG. 10).

Example 8: Pentafluorophenyl 3-{[3-(2-acetamido-2-deoxy-α-D-galactopyranosyl)oxypropylthio}propanoate (Compound 9)

Compound 9

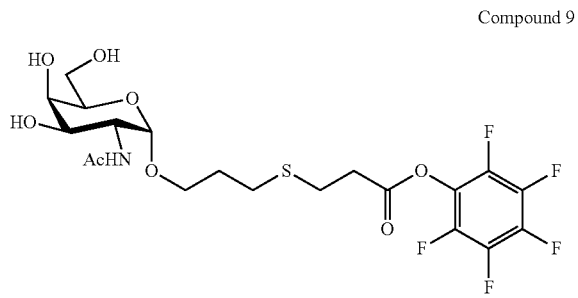

Referring to FIG. 9, from the crude reaction of compound 8 (522.54 mg, 2.0 mmol, 1.0 equiv.), 3-mercaptopropionic acid (522 μL, 6.0 mmol, 3.0 equiv.) and DMPAP (31 mg, 0.12 mmol, 0.06 equiv.) without any purification, the esterification was treated with pentafluorophenol (2.210 g 12.0 mmol, 6.0 equiv.) and EDC.HCl (1.725 g, 9.0 mmol, 4.5 equiv.) in THF/H$_2$O (10 mL, 4:1, v/v) at room temperature for one hour. The mixture was concentrated under reduced pressure. The crud was purified by flash chromatography on silica gel (EtOAc/MeOH 9:1) to afford the ester compound 9 as white solid (320 mg, 0.60 mmol, 30%).

Figure 11A:
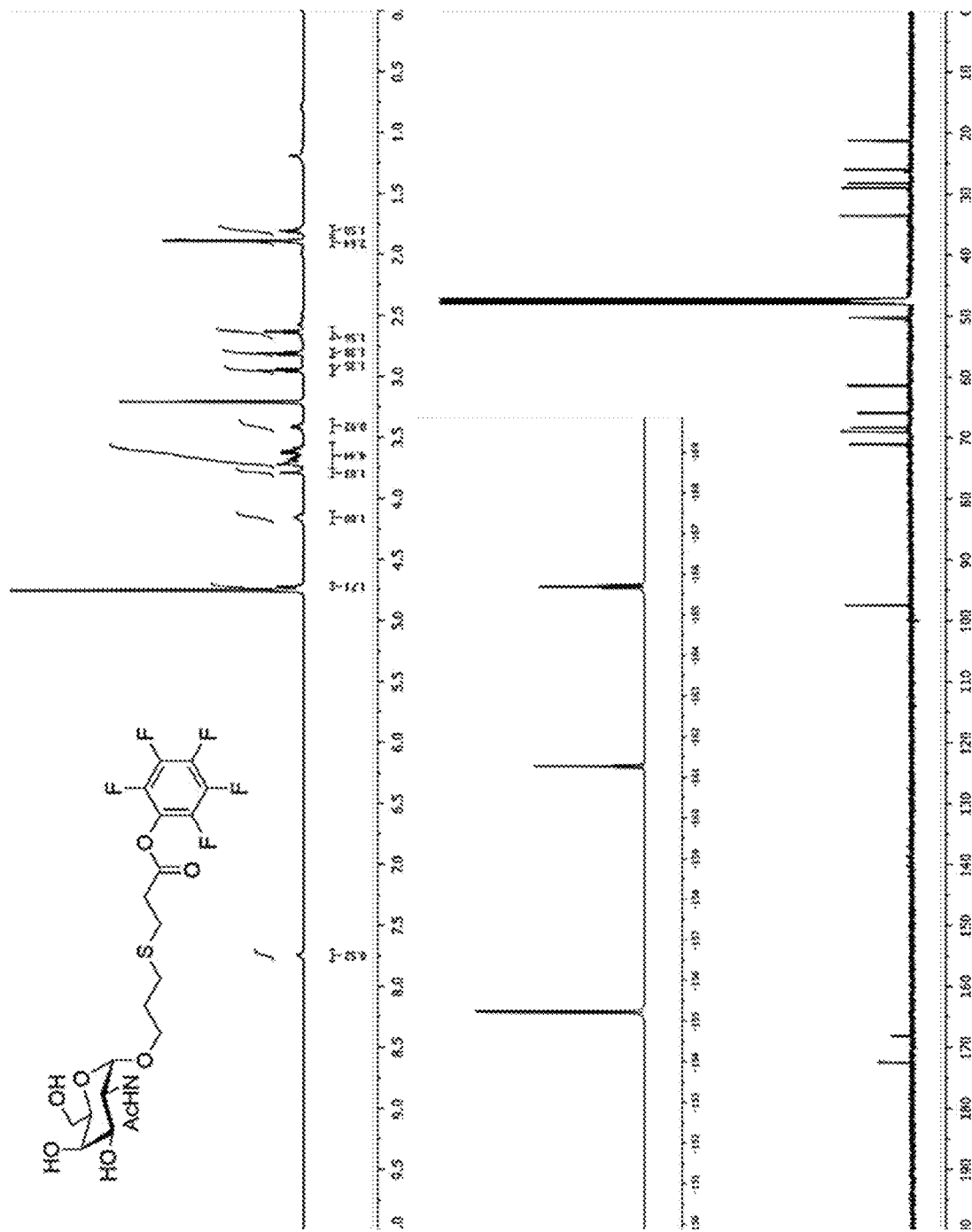
FIG. 11A-11B shows the $^1$H-NMR and $^{13}$C-NMR (FIG. 11A) spectra, as well as mass spectrometry (LC-MS) results (FIG. 11B) for Compound 9.
Figure 11B:
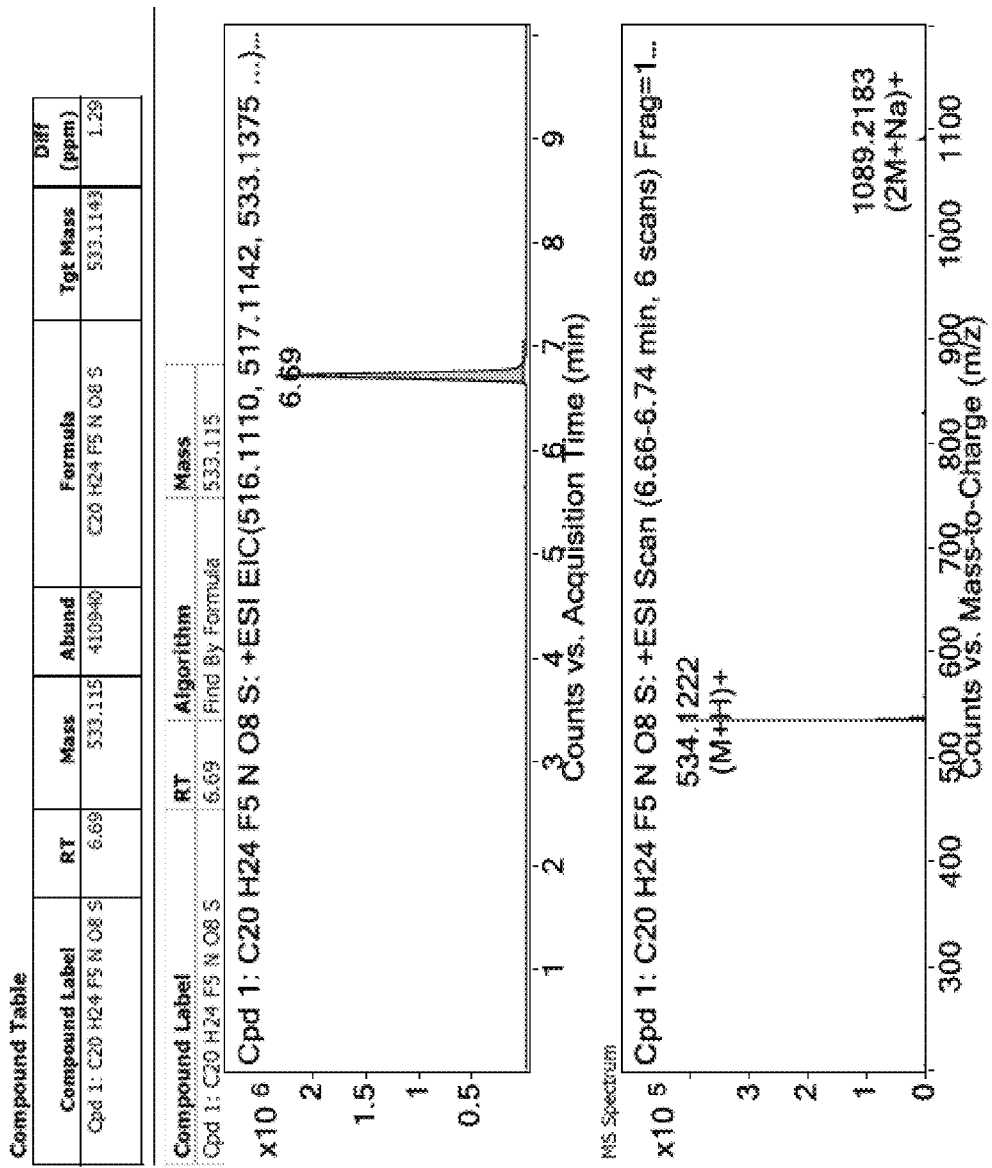

The purified acid of compound 8 (100 mg, 0.27 mmol, 1.0 equiv.) in water (1.0 mL) was treated with pentafluorophenol (200 mg, 1.09 mmol, 2.0 equiv.) in THF (4 mL) and EDC.HCl (104 mg, 0.55 mmol, 2.0 equiv.) at room temperature for one hour. The mixture was concentrated under reduced pressure. The crud was purified by flash chromatography on silica gel (EtOAc/MeOH 9:1) to afford the ester compound 9 as white solid (49 mg, 0.09 mmol, 34%). Rf=0.18; EtOAc/MeOH 9:1; $^1$H NMR (CD$_3$OD, 600 MHz): δ 4.73 (d, 1H, J=3.7 Hz, H-1), 4.25 (dd, 1H, J=11.0, 3.7 Hz, H-2), 3.79 (d, 1H, J=3.2 Hz, H-4), 3.74-3.54 (m, 5H, H-3, H-5, H-6a, H-6b, OCH$_2$), 3.41 (dt, 1H, J=10.0, 6.0 Hz, OCH$_2$), 2.95 (t, 2H, J=6.9 Hz, CH$_2$), 2.81 (t, 2H, J=6.9 Hz, CH$_2$), 2.64 (t, 2H, J=7.2 Hz, CH$_2$), 1.89 (s, 3H, CH$_3$), 1.80 (q, 2H, J=6.7 Hz, CH$_2$); $^{13}$C NMR (CD$_3$OD, 150 MHz): δ 172.5 (NHCO), 168.1 (CO), 97.5 (C-1), 71.1 (C-3), 69.0 (C-4), 68.3 (C-5), 66.0 (OCH$_2$), 61.4 (C-6), 50.3 (C-2), 33.6, 29.0, 28.3, 26.0 (4×CH$_2$) and 21.2 ppm (CH$_3$); $^{19}$F NMR (CD$_3$OD, 564 MHz): δ −(154.86-156.03, m), −(160.90-161.58, m), −(165.33-166.16, m); ESI$^+$-LC-MS: [M+H]$^+$ calcd for C$_{20}$H$_{25}$O$_8$NSF$_5$, 534.1216; found, 534.1222, 6.69 min. (FIGS. 11A and 11B).

Example 9: 3-{[3-(2,3,4,6-tetra-Q-benzoyl-β-D-galactopyranosyl)-(1→3)-2-acetamido-4,6-Q-benzylidene-2-deoxy-α-D-galactopyranosyl)oxypropyl]thio}propanoic acid (Compound 10)

Compound 10

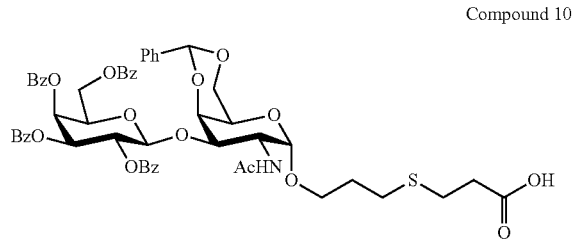

Figure 12:
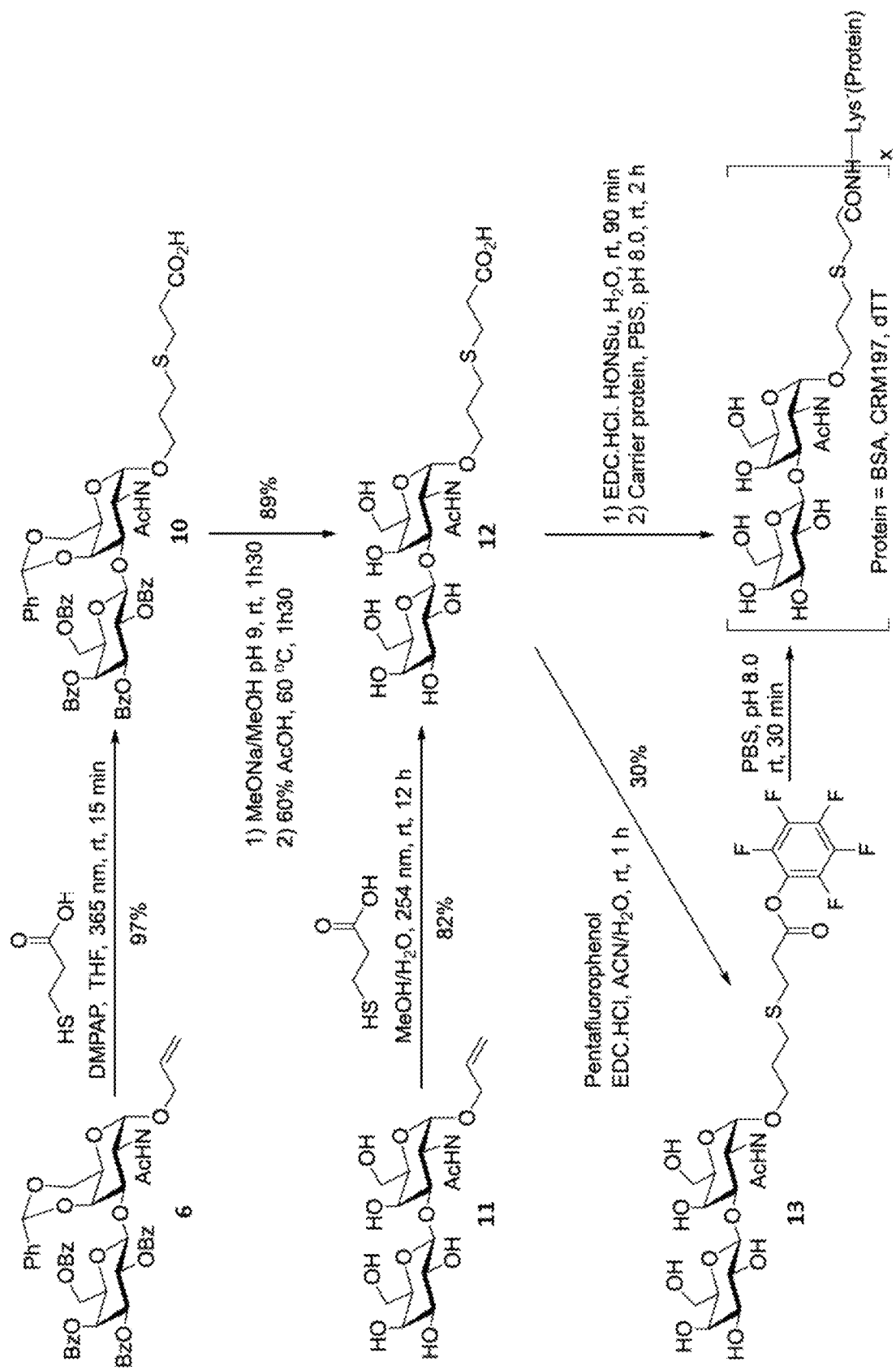
FIG. 12 shows reaction schemes for the production of neoglycoconjugate immunogens from Allyl Tn.

Referring to FIG. 12, the solution of Protected allyl TF (compound 6) (659 mg, 0.71 mmol, 1.0 equiv.) and 3-mercaptopropionic acid (186 μL, 2.13 mmol, 3.0 equiv.) in THF degassed (3 mL), was stirred at room temperature under irradiation at 365 nm with DMPAP (11 mg, 0.43 mmol, 0.06 equiv.) for 15 min. The mixture was then concentrated under reduced pressure, then purified by flash chromatography on silica gel (DCM/MeOH/AcOH 98:2:0.01) to afford the desired compound 10 as white foam (712 mg, 0.69 mmol, 97%); Rf=0.25; MeOH/MeOH/AcOH 98:2:0.01; $^1$H NMR (CDCl$_3$, 600 MHz): δ 8.05-7.14 (m, 25H), 5.92 (t, 1H, J=7.2 Hz, 1H), 5.85-5.76 (m, 1H), 5.75-5.65 (m, 1H), 5.53-5.47 (m, 1H), 5.45 (d, 1H, J=9.5 Hz), 5.16 (dd, 1H, J=19.2, 11.5 Hz), 5.10-5.02 (m, 1H), 4.71 (d, 1H, J=3.5 Hz), 4.69-4.65 (m, 1H), 4.65-4.60 (m, 1H), 4.50 (m, 1H), 4.43-4.29 (m, 1H), 4.12-3.97 (m, 1H), 3.88 (td, 1H, J=10.7, 3.3 Hz), 3.67 (ddd, 1H, J=19.3, 12.1, 5.3 Hz), 3.40-3.38 (m, 1H), 3.25 (td, 1H, J=9.5, 2.7 Hz), 2.91-2.82 (m, 1H), 2.73-2.45 (m, 1H) and 1.64 ppm (s, 1H); $^{13}$C NMR (CDC$_{13}$, 150 MHz): 5 177.07, 175.59, 170.46, 137.73, 133.51, 133.47, 133.41, 133.21, 133.17, 129.90, 129.64, 129.61, 128.57, 128.50, 128.19, 128.03, 125.99, 102.57, 100.45, 98.87, 76.44, 75.58, 72.02, 71.38, 69.41, 69.01, 68.17, 66.82, 63.15, 62.45, 52.49, 36.62, 31.48, 29.54, 28.68, 25.96, 22.55, 20.05 and 14.03 ppm; ESI$^+$-HRMS: [M+Na]$^+$ calcd for C$_{55}$H$_{55}$O$_{17}$NSNa, 1056.3083; found, 1056.3116.

Example 10: 3-{[3-(β-D-galactopyranosyl)-(1→3)-2-acetamido-2-deoxy-α-D-galactopyranosyl)oxypropyl]thio}propanoic acid (Compound 12)

Compound 12

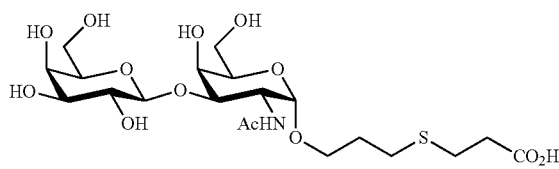

Referring to FIG. 12, the solution of allyl TF (compound 11) (85 mg, 0.2 mmol, 1.0 equiv.) and 3-mercaptopropionic acid (52 μL, 0.6 mmol, 3.0 equiv.) in H$_2$O/MeOH degassed (3 mL, 1:2, v/v), was stirred at room temperature under irradiation at 254 nm overnight. The mixture was then concentrated under reduced pressure with silica gel, then purified by flash chromatography on silica gel by gradient (EtOAc 100% to EtOAc/MeOH/H$_2$O 7:2:1) to afford the desired compound 12 as white foam (87 mg, 0.16 mmol, 82%).

Figure 13:
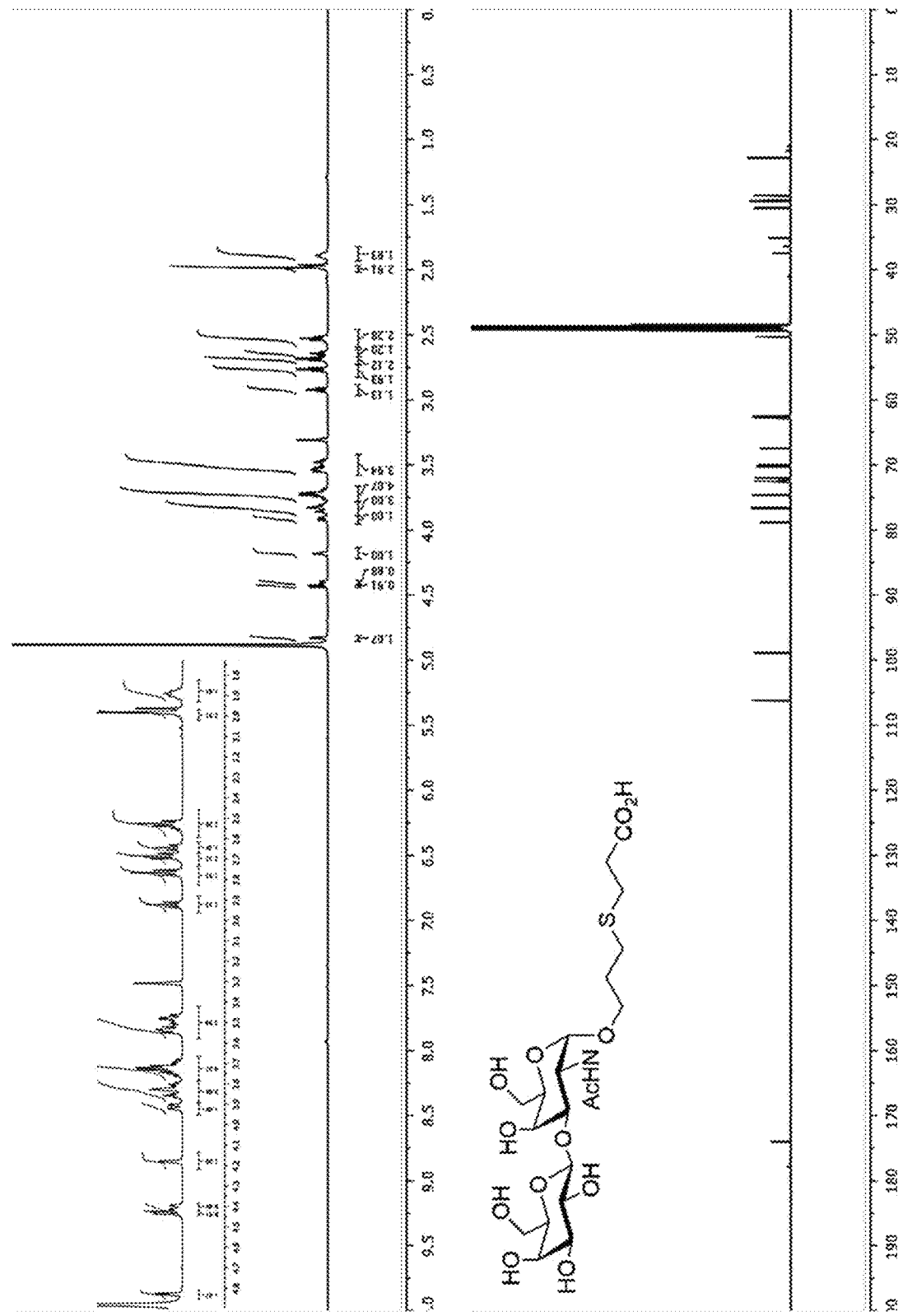
FIG. 13 shows the $^1$H-NMR and $^{13}$C-NMR spectra for Compound 12.

A solution of compound 10 (672 mg, 0.65 mmol, 1.0 equiv.) in 1M sodium methoxide in methanol (6 mL, 10 pH 8-9) was stirred at room temperature until consumption of starting material. After 1 h 30 min, the solution was neutralized by the addition of ion-exchange resin (Amberlite IR 120, H$^+$) until pH 4, washed with methanol, and the solution was concentrated under reduced pressure. The white foam intermediate crude was then treated in 6 mL of 60% aqueous acetic acid at 60° C. for 1.5 hours. The solvent was removed under reduced pressure, and the residue was purified by flash chromatography on silica gel by gradient (EtOAc 100% to EtOAc/MeOH/H$_2$O 7:2:1) to afford the desired compound 13 as white foam (306 mg, 0.58 mmol, 89%). Rf=0.34; EtOAc/MeOH/AcOH 3:1:0.01; $^1$H NMR (CD$_3$OD, 600 MHz): δ 4.83 (d, 1H, J=3.7 Hz, H-1), 4.43 (d, 1H, J=7.6 Hz, H-1'), 4.41 (dd, 1H, J=11.0, 3.7 Hz, H-2), 4.18 (d, 1H, J=2.0 Hz, H-4'), 3.91 (dd, 1H, J=11.1, 3.1 Hz, H-3), 3.87-3.67 and 3.58-3.43 (m, 11H, H-2', H-3', H-4, H-5, H-5', H-6a, H-6a', H-6b, H-6b', OCH$_2$), 2.92 (t, 2H, J=7.2 Hz, CH$_2$), 2.77 (t, 2H, J=7.4 Hz, CH$_2$), 2.68 (t, 2H, J=7.2 Hz, CH$_2$), 2.53 (t, 2H, J=7.4 Hz, CH$_2$), 1.98 (s, 3H, CH$_3$), 1.89 (m, 2H, CH$_2$); $^{13}$C NMR (CD$_3$OD, 150 MHz): 5 174.0 (CO), 106.2 (C-1'), 98.9 (C-1), 78.9, 76.7, 74.7, 72.49, 72.0 (C-3), 70.2 (C-4), 70.0, 67.4 (C-5), 62.7 (OCH$_2$), 62.5 (C-6), 50.3 (C-2), 37.4, 35.1, 30.5, 29.5, 28.6 (CH$_2$) and 22.8 ppm (CH$_3$). ESI$^+$-HRMS: [M+H]$^+$ calcd for C$_{20}$H$_{36}$O$_{13}$NS, 530.1902; found, 530.1909. (FIG. 13).

Example 11: Pentafluorophenyl 3-{[3-(β-D-galactopyranosyl)-(1→3)-2-acetamido-2-deoxy-α-D-galactopyranosyl)oxypropyl]thio}propanoate (Compound 13)

Compound 13

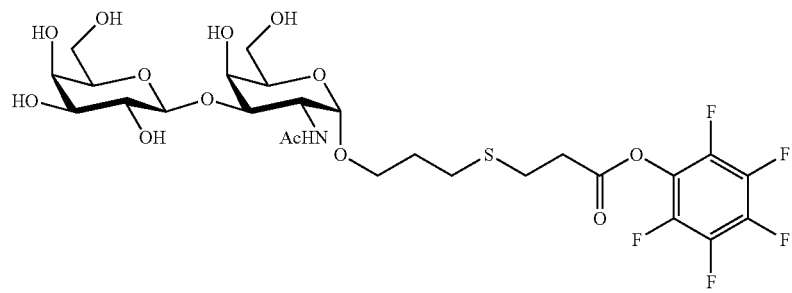

Figure 14:
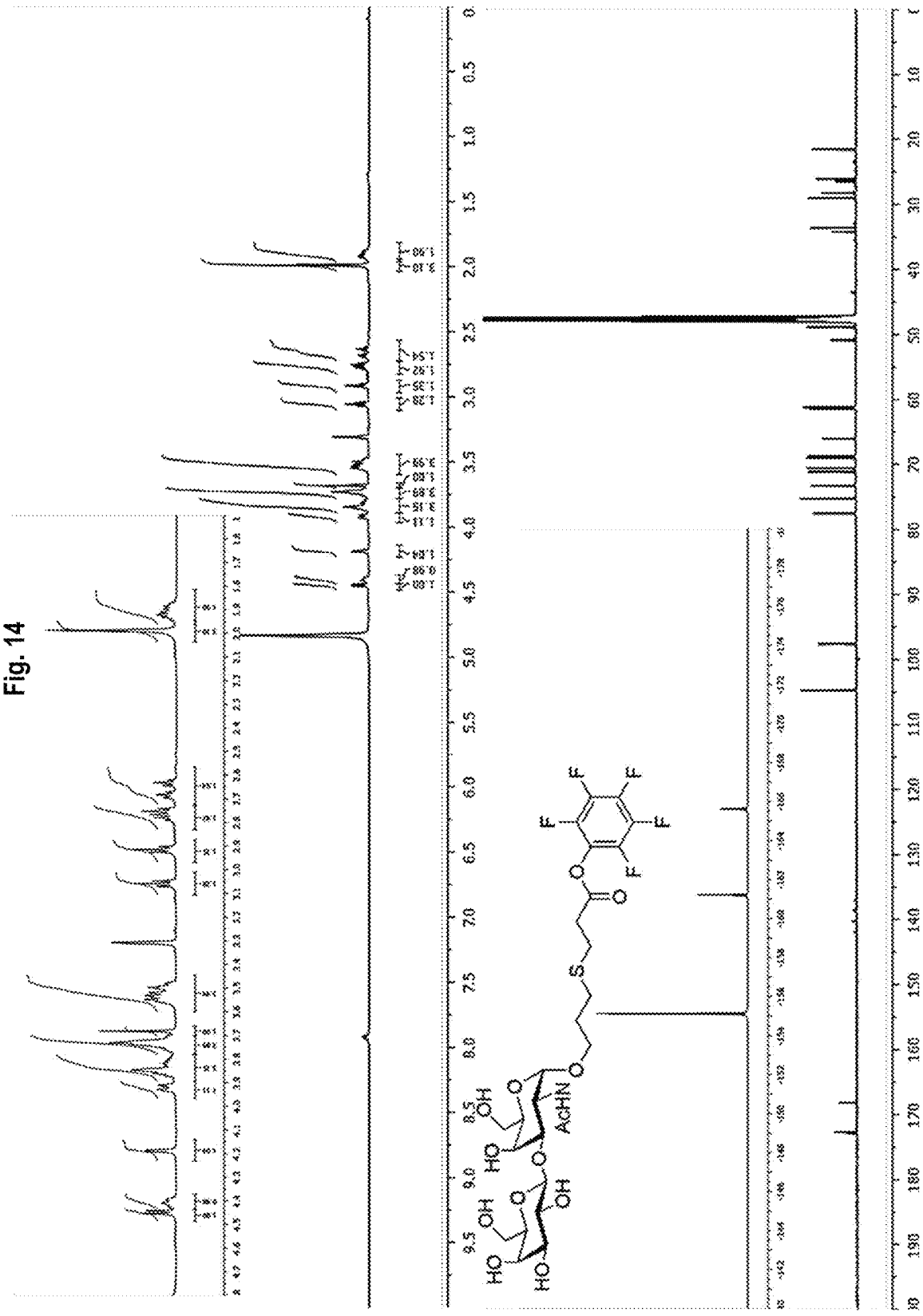
FIG. 14 shows the $^1$H-NMR and $^{13}$C-NMR spectra for Compound 13.

The purified acid Compound 12 (159 mg, 0.30 mmol, 1.0 equiv.) in water (1.0 mL) was treated with pentafluorophenol (331 mg, 1.80 mmol, 6.0 equiv.) in acetonitrile (4 mL) and EDC.HCl (259 mg, 1.35 mmol, 4.5 equiv.) at room temperature for one hour. The mixture was concentrated with silica gel under reduced pressure. The crud was purified by flash chromatography on silica gel by gradient (EtOAc 100% to EtOAc/MeOH 6:4) to afford the ester compound 13 as white solid (62 mg, 0.09 mmol, 30%). Rf=0.50; EtOAc/MeOH 6:4; $^1$H NMR (CD$_3$OD, 600 MHz): δ 4.45 (d, 1H, J=7.5 Hz, H-1'), 4.41 (ddd, 1H, J=12.6, 6.1, 2.8 Hz), 4.19 (d, 1H, J=3.0 Hz), 3.92 (dd, 1H, J=11.0, 3.1 Hz), 3.89-3.77 (m, 3H), 3.74 (m, 4H), 3.68 (s, 1H), 3.52 (m, 4H), 3.06 (t, 1H, J=6.9 Hz), 2.91 (t, 1H, J=6.9 Hz), 2.77 (dt, 2H, J=15.0, 7.1 Hz), 2.68 (t, 1H, J=7.1 Hz), 2.63 (t, 1H, J=7.0 Hz), 1.99 (s, 1H) and 1.95-1.84 ppm (m, 2H); $^{13}$C NMR (CD$_3$OD, 150 MHz): δ 172.7 (NHCO), 168.1 (CO), 104.7 (C-1'), 97.6 (C-1), 77.5, 75.3, 73.3, 71.1, 70.6, 69.0, 68.7, 66.0, 61.4, 61.2, 50.9, 48.9, 34.2, 33.6, 29.0, 28.2, 28.2, 26.4, 26.1, 21.5 and 21.5 ppm; $^{19}$F NMR (CD$_3$OD, 564 MHz): δ −155.12 (m), −161.21 (m), −165.63 (m); ESI$^+$-HRMS: [M+H]$^+$ calcd for C$_{26}$H$_{35}$O$_{13}$NSF$_5$, 696.1744; found, 696.1739. (FIG. 14).

Example 12: PFP-Tn Conjugation to BSA and CRM197

Referring to FIG. 9, the conjugation of PFP-Tn (compound 9) to protein was demonstrated with BSA and CRM197. BSA (fatty acid free, low endotoxin; Sigma) was solubilized at a concentration of 1 mg/mL in each of 5 buffers, each having increased pH: (1) 0.1 M MES and 150 mM NaCl pH 6; (2) Phosphate buffered saline (PBS) pH 7; (3) PBS pH 8; (4) 0.1 M Sodium Carbonate with 150 mM NaCl pH 9; and (5) 0.1 M Sodium Carbonate with 150 mM NaCl pH 10. The conjugation of Tn to BSA was initiated by combining 400 μL (6 nmols) of BSA solution with 60 μL of the respective buffer containing 5, 15, 50, or 200 equivalents of PFP-Tn (compound 9) (20 mM in water) to BSA and agitating by gentle vortexing for 90 min. The resulting BSA-Tn conjugates were then washed with PBS pH 7.4 by centrifugal filtration (MWCO 10 KDa, Amicon). The concentration of proteins was measured by Bradford assay. The conjugate CRM197-Tn was obtained in similar conditions by incubating up to 15 molar equivalents of PFP-Tn (compound 9) with purified CRM197 at 4 mg/mL in 0.4 M sodium phosphate buffer pH 7.2 for 2 h.

The protein-Tn conjugates were analyzed for reactivity to the Tn-specific lectin *Vicia Villosa* (VVA) by Western blot and/or ELISA.

FIG. 15 depicts the reactivity to VVA of BSA-Tn conjugates generated in buffers of pH 6 to 10 and at a ratio of 50 Eq PFP-Tn to BSA. The Western blot in FIG. 15A shows a predominant reactive band in the region of the molecular weight of BSA (about 66.5 kDa), indicating that Tn conjugation occurred in all 5 buffers ranging from pH 6 to 10. A band of higher intensity and slightly slower migration was detected in the pH 8 condition, suggesting a higher level of conjugation of Tn to BSA resulting from a more effective reaction at pH 8 than the other pH's tested. The higher reactivity of BSA-TF pH8 to VVA was also confirmed by ELISA (FIG. 15B).

Figure 15A:
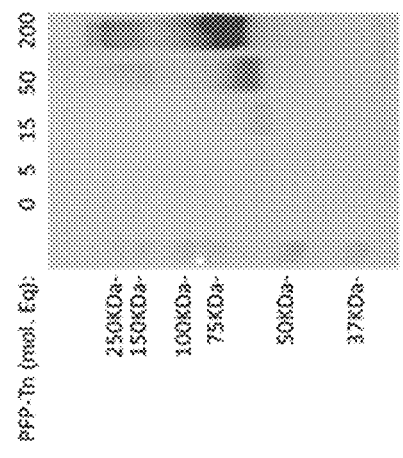
FIG. 15A-15E shows the reactivity of the Tn-recognizing lectin *Vicia Villosa* (VVA) to BSA-Tn (FIGS. 15A-15D) and CRM197-Tn (FIG. 15E) conjugates.
Figure 15B:
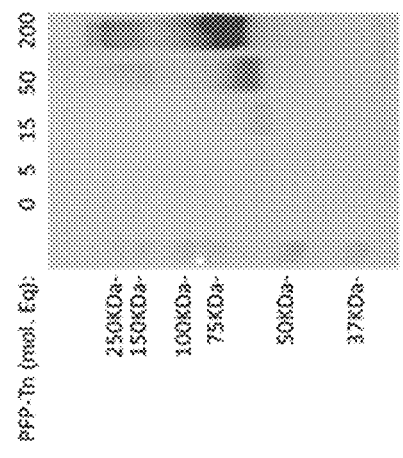
Figure 15C:
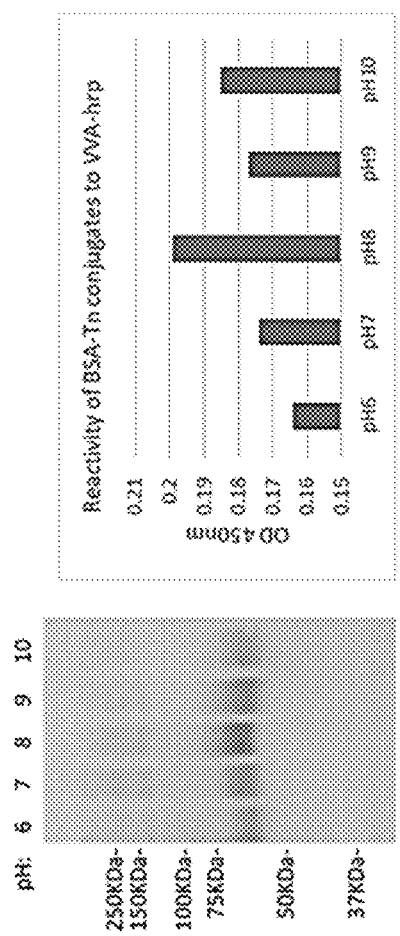
Figure 15D:
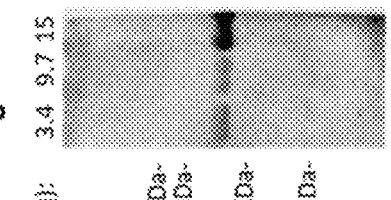

FIG. 15C shows the titration of PFP-Tn (compound 9) on conjugation to BSA at the optimal pH of 8. By Western blot, a VVA reactive BSA-Tn species generated with a minimum of 15 molar equivalent of PFP-Tn to BSA was detected. Increasing the ratio of PFP-Tn to 50 and 200 molar equivalents to BSA resulted in a corresponding increase in band intensity and a slower migration on gel, resulting from a higher level of conjugated Tn to BSA. A correlation between the amount of PFP-Tn and the reactivity of the resulting BSA-Tn conjugate was also observed by ELISA (FIG. 15D). The ELISA further demonstrated that the correlation is linear from 5 to 200 equivalents PFP-Tn, suggesting that the PFP-Tn conjugation sites on BSA were not saturated.

Figure 15E:
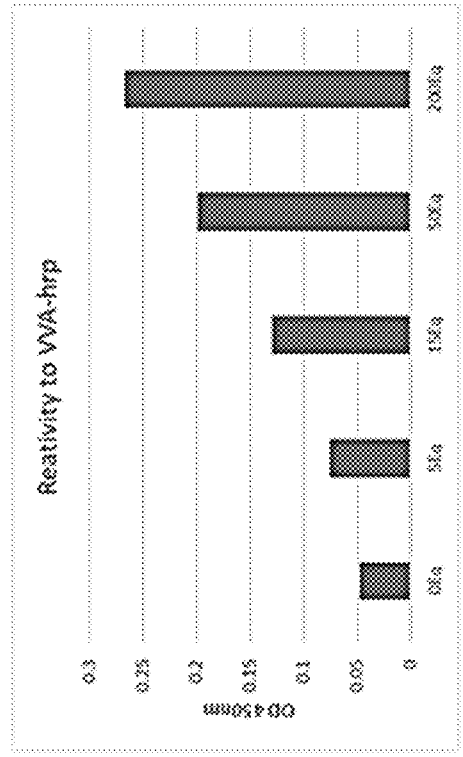

FIG. 15E shows Western blot analysis of CRM197-Tn. The blot revealed a single VVA reactive band in the range of the molecular weight of CRM197 (about 58.4 kDa) for the 3 conjugation ratios of PFP-Tn tested (i.e., 3.4, 9.7, and 15), with the most reactive species of the three generated at the highest PFP-Tn ratio of 15 equivalents.

The mass analysis of the CRM197 conjugated with 15 equivalents of PFP-Tn was further analyzed by mass spectrometry and confirmed the conjugation (data not shown).

Example 13: PFP-TF Conjugation to BSA

The conjugation of PFP-TF (compound 13) to protein was demonstrated with BSA. BSA (fatty acid free, low endotoxin; Sigma) was solubilized at a concentration of 1 mg/mL in PBS pH 8 and 400 μL (6 nmols) was mixed with 60 μL of PBS pH 8 containing 5, 15, 50, or 200 equivalents of PFP-TF (20 mM in water), then agitated by gentle vortexing for 90 min. The resulting BSA-TF conjugates were washed with PBS pH 7.4 by centrifugal filtration (MWCO 10 kDa, Amicon). The concentration of proteins was measured by Bradford assay.

Figure 16B:
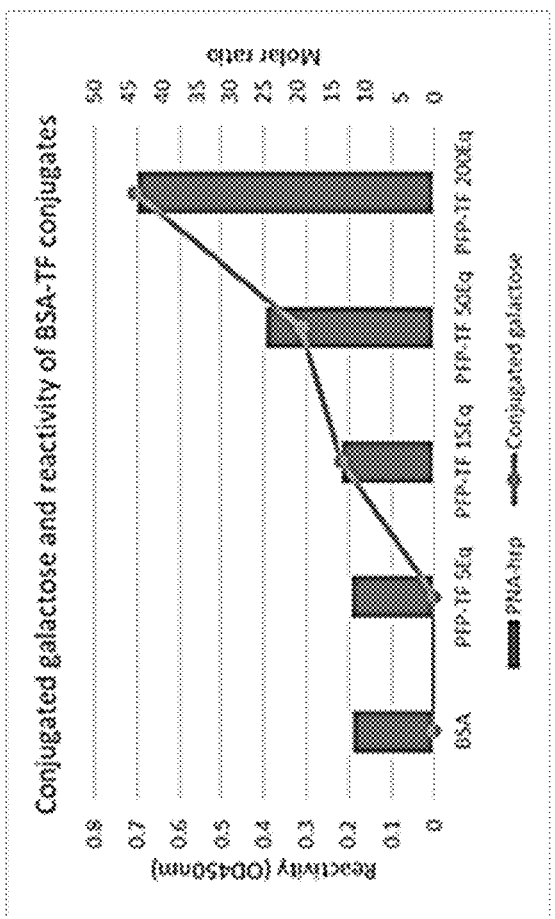
FIGS. 16A and 16B shows the reactivity of the BSA-TF conjugates to the TF-specific lectin Peanut Agglutinin (PNA) and the dosage of the galactose sugar from the conjugated disaccharide TF antigen.
Figure 16A:
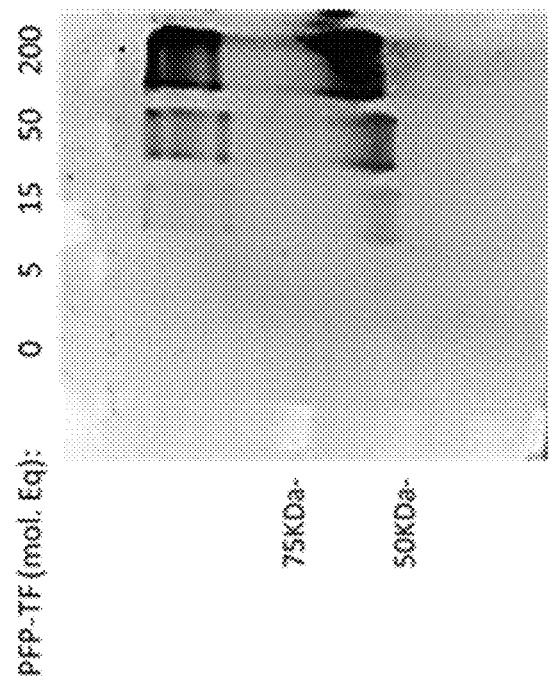

FIG. 16 shows the reactivity of the resulting BSA-TF conjugates to the TF-specific lectin *Peanut Agglutinin* (PNA) and the dosage of the galactose sugar from the conjugated disaccharide TF antigen. The Western blot shown in FIG. 16A revealed a predominant band reactive to PNA in the range of the expected molecular weight of the BSA monomer indicating the coupling of TF to BSA. The gel also showed that increasing the ratio of PFP-TF to 50 and 200 molar equivalents to BSA resulted in a corresponding increase in band intensity and a slower migration on gel, resulting from a higher level of conjugated TF to BSA. A linear correlation between 15-200 equivalents of PFP-TF and the reactivity of the resulting BSA-Tn conjugate was also observed by ELISA (FIG. 16B), suggesting that the PFP-TF conjugation sites on BSA were not saturated under these conditions. The conjugation of TF to BSA was also demonstrated by measuring the galactose associated to BSA by the method of Dubois. The bar graph in FIG. 16B shows that the amount of galactose increases correspondingly with the PNA reactivity of the BSA-TF and reaching a ratio of 45 per BSA when the conjugation is performed with 200 equivalents of PFP-TF.

Example 14: COOH-Tn and COOH-TF Conjugation to CRM197 and dTT

The conjugation of COOH-Tn and COOH-TF to protein was demonstrated with CRM197 and dTT. The COOH-Tn (compound 8) and COOH-TF (compound 12) were first succinimidated by combining the saccharide antigen dissolved in water at 0.1 M, with 2 equivalents each of a 0.1 M aqueous solution of N-(3-dimethylaminopropyl)-N'-ethyl-carbodiimide (EDC, Sigma-Aldrich) and N-hydroxysuccinimide (NHS, Sigma-Aldrich) and vortexing at RT for a minimum of 30 minutes. The resulting chemically reactive antigen was then diluted up to 4 times with PBS pH 8 and the coupling to the protein was initiated by adding 50 equivalents to the protein solution in PBS pH 8 at a concentration of 10 mg/mL. The solution was vortexed for 30-120 minutes before washing the resulting protein-antigen conjugate by membrane filtration (Amicon, MWCO 30,000 Da) with PBS pH 7.4. The concentration of proteins was measured by Bradford assay.

FIG. 17 shows the migration of the protein alone and the resulting conjugates by gel electrophoresis and their reactivity to the lectin VVA (Tn-specific) and PNA (TF-specific) by Western blot and ELISA. The Coomassie stained SDS-PAGE gel (FIG. 17A) of the conjugates show that the conjugated proteins migrate similarly as the native unconjugated protein, indicating the absence of aggregation or degradation as a result of the protein conjugation to Tn or TF. The Western blot (FIG. 17B) shows the specific reactivity the protein conjugates to VVA or PNA lectins, indicating coupling of Tn or TF. The same pattern of specific reactivity to lectins was also observed by ELISA (FIG. 17C).

Example 15: Characterization of the Immunoreactivity of Serums from Mice Immunized with the Neoglycoconjugate dTT-TF The glycoconjugates dTT-TF were prepared as described in Example 14, diluted to 1 mg/mL with PBS pH 7.4 and emulsified with an equal volume of TiterMax™ Gold (SigmaAldrich). 25 µL of the formulation was injected intramuscularly in the left and right thighs of 8-week-old female BALB/c mice every 2 weeks for five immunizations in a total of twelve mice. Mice were pre-bled to collect a sample of pre-immune serum and then bled 1 week after each immunization.

The sera were tested by ELISA to assess the titer of anti-TF or anti-Tn antibodies. 96-well plates (Nunc, Maxisorp™) were coated with the indicated screening antigens: BSA-Tn and BSA-TF (as described in Example 14), or polyacrylamide [PAA]-Tn and PAA-TF (GlycoTech, USA) at a concentration of 1 µg/100 µL in PBS pH 7.4. After 1h of incubation at room temperature, coated wells were washed with PBS-Tween (PBS-T) 0.05% and blocked with PBS-T 0.05%+1% BSA for 30 minutes. After washing with PBS-Tween 0.05%, wells were incubated for 1h with a 1/200 dilution of sera in PBS-Tween 0.05%. Wells were then washed and incubated for 30 minutes with goat anti-mouse IgG-HRP at 1/1000 dilution in PBS-Tween 0.05%. The binding of murine antibody was measured by adding the HRP colorimetric substrate ultra-TMB (Thermo) followed by an equal volume of 0.5M sulfuric acid to stop the reaction. The plate was read in a plate reader at $OD_{450}$. Of the 12 mice that received at least five immunizations with dTT-TF, significant levels of anti-TF antibodies were detected in the sera six mice by ELISA.

TABLE 1

Reactivity of sera from mice immunized 3x with dTT-TF to TF and Tn screening antigens

| Mice sera | | BSA-TF | PAA-TF | BSA-Tn | PAA-Tn |
|---|---|---|---|---|---|
| A1 | Pre-Immune | 0.077 | 0.107 | 0.096 | 0.100 |
| | Immune | 2.501 | 0.762 | 0.824 | 0.650 |
| | Normalized* (FIG. 18) | 32.5 | 7.1 | 8.6 | 6.5 |
| A2 | Pre-Immune | 0.513 | 0.429 | 0.589 | 0.645 |
| | Immune | 2.502 | 2.373 | 2.183 | 0.464 |
| | Normalized* (FIG. 18) | 4.9 | 5.5 | 3.7 | 0.7 |

*(Immune $OD_{450}$)/(Pre-immune $OD_{450}$)

Figure 18:
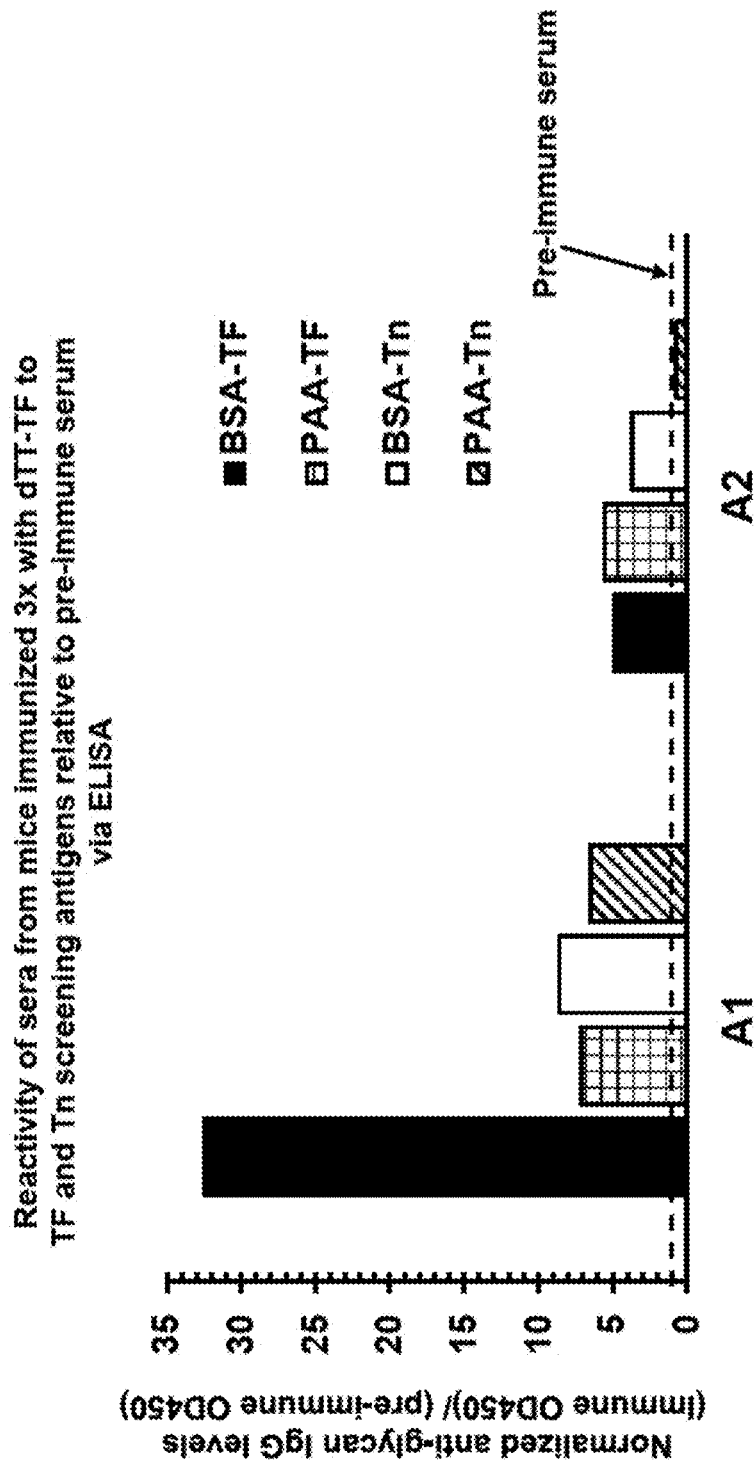
FIG. 18 shows the normalized reactivity of sera from mice immunized three times with dTT-TF to various TF and Tn screening antigens by ELISA.

Table 1 and FIG. 18 show the ELISA results of sera from two mice (A1 and A2) after three immunizations with dTT-TF, as well as normalized data according to their respective pre-immune sera. The results show that sera from mouse A1 reacted with all of the TF and Tn screening antigens (ranging from 6.5- to 32.5-fold increase over corresponding pre-immune sera), with the highest reactivity being observed for BSA-TF (32.5-fold increase over corresponding pre-immune sera). The sera from mouse A2 showed reactivity with both TF screening antigens (BSA-TF and PAA-TF), but only one the Tn antigens that was conjugated to a carrier protein (Tn-BSA). These results show that immunization with the neoglycoconjugate dTT-TF successfully induced the production of antibodies against the TF carbohydrate antigen, independent of the carrier. Furthermore, these results suggest that at least some of the anti-TF antibodies produced are cross-reactive with the Tn antigen, which is a cryptic epitope within TF antigen (FIG. 1).

FIGS. 19A and 19B show an ELISA of serially diluted sera (1:100 to 1:1,000,000) from two mice taken at post-5th immunization with dTT-TF and at 6 weeks following the 5th immunization, using BSA-TF as a screening antigen. The curves show that the antibody titer is not reduced 6 weeks after the last immunization indicating a prolonged antibody half-life. Similar results were observed using PAA-TF as a screening antigen (data not shown).

Example 16: Quantitative O-Glycosylation Profile of SARS-CoV-2 Spike Protein Subunit S1 Characterized by High Resolution Mass Spectrometry S1 Protein Preparation 27 µL of recombinant SARS-CoV-2 S1 subunit with C-terminal His-tag from serum-free cell culture supernatant of transfected HEK293 cells (RayBiotech, USA) in reducing sample buffer was separated by electrophoresis on a 10% SDS-PAGE. The gel was stained with Coomassie blue G-250. The section of lane corresponding to 75 kDa and higher was cut into 10 pieces under a clean bench and each piece cut further into 1 $mm^3$ pieces.

Gel Pieces Preparation

Gel pieces were first washed with water for 5 min and destained twice with a destaining buffer (100 mM sodium thiosulfate, 30 mM potassium ferricyanide) for 15 min. An extra wash of 5 min was performed after destaining with an ammonium bicarbonate buffer (50 mM). Gel pieces were then dehydrated with acetonitrile (ACN). Protein cysteine disulfide groups were reduced by adding the reduction buffer (10 mM Dithiothreiol (DTT), 100 mM ammonium bicarbonate) for 30 min at 40° C. The generated free-sulfhydryl groups were then alkylated to S-carboxyamidomethyl by adding the alkylation buffer (55 mM iodoacetamide, 100 mM ammonium bicarbonate) for 20 min in the dark at 40° C. Gel pieces were then dehydrated and washed at 40° C. by adding acetonitrile for 5 min before discarding all of the reagents.

Proteolytic Digestion and Peptides Extraction Steps

Gel pieces were dried for 5 min at 40° C. and then re-hydrated at 4° C. for 40 min with a trypsin solution (6 ng/µL of trypsin [sequencing grade] from Promega, 25 mM ammonium bicarbonate). Protein digestion was performed at 58° C. for 1 h and stopped by adding 15 µL of 1% formic acid/2% acetonitrile. Supernatant was then transferred into a 96-well plate and peptides extraction was performed with two 30-min extraction steps at room temperature using the extraction buffer (1% formic acid/50% ACN). All peptide extracts were completely dried in a vacuum centrifuge.

LC-MS/MS Analysis

Prior to LC-MS/MS, protein digests were re-solubilized under agitation for 15 min in 10 µL of 1% ACN/0.5% formic acid. A 15 cm long, 75 µm i.d. Self-Pack PicoFrit™ fused silica capillary column (New Objective, Woburn, Mass.) was packed with C18 Jupiter™ (5 µm, 300 Å) reverse-phase material (Phenomenex, Torrance, Calif.). This column was installed on the Easy-nLC™ II system (Proxeon Biosystems, Odense, Denmark) and coupled to the Orbitrap Fusion™ (Thermo-Fisher Scientific, Bremen, Germany) equipped with a Nanospray Flex™ Ion Source (Thermo-Fisher Scientific). The buffers used for chromatography were 0.2% formic acid (buffer A) and 100% acetonitrile/ 0.2% formic acid (buffer B). Peptides were eluted with a two-slope gradient at a flowrate of 250 nL/min. Solvent B first increased from 1 to 35% in 75 min and then from 35 to 86% in 15 min. Nanospray and S-lens voltages were set to 1.3-1.7 kV and 50 V, respectively. Capillary temperature was set to 225° C. Full scan MS survey spectra (360-1560 m/z) in profile mode were acquired in the Orbitrap with a resolution of 120 000 with a target value set at 8e5. A cycle time of 3 seconds was used for the data dependent MS/MS analysis, where the selected precursor ions were fragmented in the HCD (Higher-energy C-trap dissociation) collision cell and analyzed in the Orbitrap with the resolution set at 30 000, the target value at 7e4 and a normalized collision energy at 28 V. A subsequent MS/MS analysis using CID (Collision Induced Dissociation) was performed in the Orbitrap upon detection of oxonium ions. An inclusion list was also used for all know forms of peptide 320-328 of SARS-Cov-2. A second series of analysis was performed on these peptides by using a SIM (Single Ion Monitoring) and targeted MS2 method.

Data Analysis

Protein database searches were performed with Mascot 2.6 (Matrix Science) against the Uniprot protein database (2017-04-11). The mass tolerances for precursor and fragment ions were set to 10 ppm and 0.6 Da, respectively. The enzyme specified was trypsin and one missed cleavage was allowed. Cysteine carbamidomethylation was specified as a fixed modification and methionine oxidation as variable modification. A second series of searches was performed against the SARS-CoV-2 sequence using Mascot 2.6 and Byos 3.8 (Protein Metrics). The enzyme specified was semi-trypsin and one missed cleavage was allowed. Cysteine carbamidomethylation was specified as a fixed modification. Methionine oxidation and all known O-glycosylated forms of peptide 320-328 were used as variable modifications.

FIG. 20 shows the quantitative O-glycosylation profile of peptide VQPTESIVR (SEQ ID NO: 3) from SARS-CoV-2 S1 protein characterized by high-resolution LC-MS/MS of proteins over 75 kDa. FIG. 25 21 shows the same analysis done by high-resolution LC-MS/MS of proteins between 75-100 kDa. The symbols nomenclature for graphical representation of individual glycans are as follows (Varki et al., 2015): yellow square=GalNAc, yellow circle=Gal, purple diamond=Neu5Ac (sialic acid). TF is formed by the disaccharide Gal-GalNAc. The figures show a different pattern of glycosylated-peptide with the predominant species being di-sialyl-TF, and the second most abundant being TF.

Figure 22:
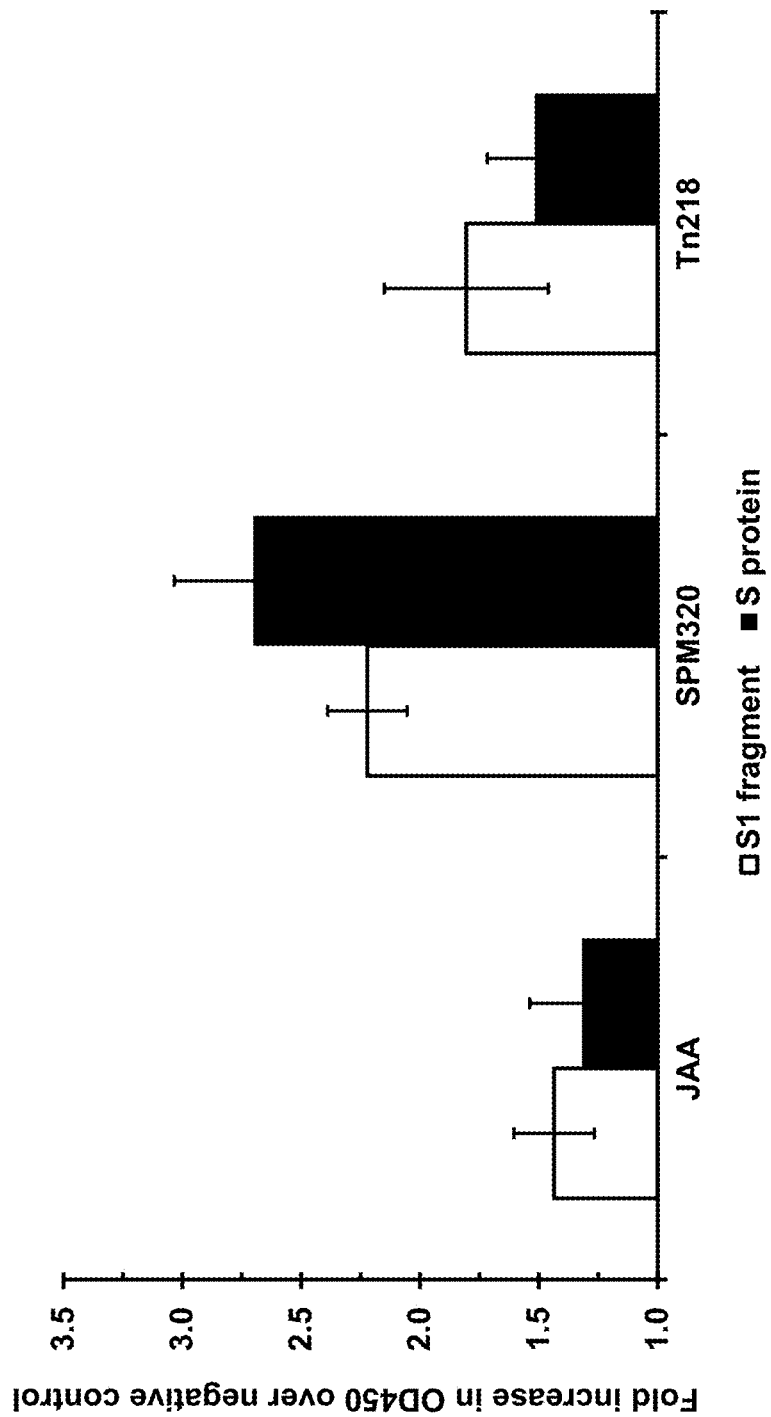
FIG. 22 shows the reactivity by ELISA of anti-TF (JAA-F11 IgG and SPM320 IgM) and anti-Tn (Tn218 IgM) monoclonal antibodies to culture supernatant from mammalian cells transfected with either SARS-CoV-2 S1 protein or full length S protein. Results are shown as fold increases over the same monoclonal antibodies exposed to culture supernatant from corresponding mammalian cells transfected with empty vector.

Example 17: Reactivity of Anti-Tn and Anti-TF Ligands to Recombinant SARS-CoV-2 S1 and S Proteins by ELISA and Western Blot Wells of a 96-well plate were coated for 1h with 100 μL PBS pH 7.4 containing 10 μL of serum-free culture supernatant of mammalian cells transfected with either empty vector or with DNA encoding either recombinant SARS-CoV-2 S1 (S1 subdomain of spike protein; RayBiotech, USA, Cat. No. 230-20407) or S (full length spike protein; NRC, Canada) with a C-terminal His-tag. Wells were then washed with PBS-Tween 0.05% and blocked with PBS-T 0.05%+1% BSA for 30 minutes. The wells were then washed with PBS-T 0.05% and further incubated for 1h with the indicated anti-TF (JAA-F11 IgG, 1 μg/mL; SPM320 IgM, Abnova, Cat. No. MAB13207, 0.2 mg/mL, 1:100 dilution) or anti-Tn (Tn218 IgM, Abnova, Cat. No. MAB6198, 1:100 dilution) antibodies in PBS-T 0.01% followed by incubating 30 minutes with their appropriate FIRP-conjugated secondary antibodies (goat anti-mouse IgG-FIRP or goat anti-mouse IgM-FIRP; Jackson Immuno, 1/1000) in PBS-T. The binding of the ligands was revealed with the HRP colorimetric substrate ultra-TMB (Thermo). The reaction was stopped by adding an equivalent volume of 0.5M sulfuric acid and the optical density was measured at 450 nm on a plate reader (Biotek). Results shown in FIG. 22 are the fold increase of the $OD_{450}$ with supernatant from HEK cells expressing the recombinant S1 or S proteins over the $OD_{450}$ of the supernatant from HEK cells transfected with the empty vector, for each antibody. The fold increases shown represent the means of at least six separate experiments and the error bars represent standard error of the means. The experiment was also repeated using recombinant S1 protein expressed from insect (Sf9) cells (S1-His, Sino-Biological, Cat, No. 40591-V08B1) and the results yielded mean fold increases of 3.32±1.35 with JAA-F11, 5.50±1.80 with SPM320, and 1.77±0.64 with Tn218 (mean of three experiments±SEM).

A similar ELISA experiment as above was performed with a panel of HRP-conjugated lectins using the serum-free culture supernatants of HEK293 cells transfected with empty vector, DNA encoding the S1 protein, or DNA encoding the full-length S protein of SARS-CoV-2 (see above). The lectin panel included lectins from: *Arachis hypogaea* (PNA; Cat. No: H-2301-1), *Vicia villosa* (VVA; Cat. No: H-4601-1), *Salvia sclarea* (SSA; Cat. No: H-3501-1), *Maackia amurensis* (MAA; Cat. No: H-7801-1), *Maclura pomifera* (MPA; Cat. No: H-3901-1). All lectins were purchased from EY Laboratories (CA, USA; 1 mg/mL, HRP-conjugated) and used at 10 μg/mL in PBS-Tween 0.01%. Results shown in FIG. 23 are the fold increase of the $OD_{450}$ with supernatant from HEK cells expressing the recombinant S1 or S proteins over the $OD_{450}$ of the supernatant from HEK cells transfected with the empty vector, for each lectin. The fold increases shown represent the means of at least seven separate experiments and the error bars represent standard error of the means. The experiment was also repeated using recombinant S1 protein expressed from insect (Sf9) cells (S1-His, SinoBiological, Cat, No. 40591-V08B1) and the results yielded mean fold increases of 22.67±12.52 with PNA, 22.51±9.71 with VVA, 3.97±1.09 with SSA, 4.30±1.23 with MAA, and 7.51±3.64 with MPA.

For Western blotting, 2 μL of serum-free culture supernatant of HEK293 cells transfected with DNA encoding SARS-CoV-2 S1 with C-terminal His-tag in reducing sample buffer was separated by SDS-PAGE on a 10% polyacrylamide gel. The proteins were then transferred to a PVDF membrane for analysis by Western blot with anti-glycan lectins, antibodies, and sera. The reactivity of the anti-glycans was compared to that of an anti-His tag antibody in corresponding conditions as a control. Bands detected with PNA, VVA, and the JAA-F11 mAb were similar to those detected with the control anti-His-Tag Ab, suggesting that they recognize the same S1 protein (data not shown). The mouse A1 immune serum (Example 15) also detected S1 strongly as compared to a pool of pre-immune serum.

Collectively, the results in this Example consistently show that the carbohydrate antigens Tn and TF are present on recombinant SARS-CoV-2 S1 and S proteins produced by Example 18: Cellular Inhibition of the Infectivity of Pseudotyped Virus Expressing SARS-CoV-2 S by O-Glycan Ligands FIG. 24 shows the relative infectivity of the pseudotyped lenti-luc-SARS-CoV-2-S virus to 293T cells expressing human angiotensin-converting enzyme 2 (293T-ACE2), the receptor to which S binds. The virus was first pre-incubated for 1h at 37° C. with serial dilutions with the anti-glycan lectins PNA, AIA (jac) [Jacalin lectin (*Artocarpus integrifolia*), and the monoclonal anti-TF antibody JAA-F11. The mixture was then added to 293T cells seeded in 96-well plates and incubated for 2h. The media was then replaced with fresh media and further incubated for 2 days. The luciferase activity was then measured. FIG. 24 shows that the lectins PNA and AIA inhibited—in a concentration-dependent manner—the ability of the pseudotyped lenti-luc-SARS-CoV-2-S virus to infect 293T-ACE2 cells. Only the highest concentration of JAA-F11 showed some inhibition of infectivity.

Interestingly, the AIA (Jacalin) lectin is known to have binding specificities for both the TF and Tn antigens in either their sialylated or unsialylated forms, while the PNA lectin (having binding affinity for terminal beta-galactose) is known to bind TF antigen in its unsialylated form only (Li et al., 2010). Similarly, the JAA-F11 antibody is known to bind only to the unsialylated form of TF antigen. Thus, the more potent inhibitory effect of AIA as compared to PNA and JAA-F11 shown in FIG. 23 is consistent with the distribution of O-glycosylated forms detected on the SARS-CoV-2 S1 protein shown in FIG. 20 and FIG. 21, as well as the relative reactivities of the different anti-Tn and anti-TF ligands shown in FIG. 22 and FIG. 23.

The results in this Example suggest that the SARS-CoV-2-S protein expressed in the context of a pseudotyped viral particle indeed contains surface TF and Tn carbohydrate antigens that are accessible to binding by anti-TF and/or anti-Tn ligands. The results in this Example further suggest ligand binding of O-glycans on the surface of the S protein expressed in the context of a viable pseudoviral particle—and, in particular, binding by the lectins PNA and AIA—may be promising strategies for prophylactic and/or therapeutic interventions against COVID-19.

REFERENCES

Cipolla et al., "Stereoselective synthesis of α-C-glycosides of N-acetylgalactosamine", *Tetrahedron Asymm.* (2000), 11: 295-303.

Cui et al., "Stereocontrolled allylation of 2-amino-2-deoxy sugar derivatives by a free-radical procedure", *Carbohydr. Res.*, (1998), 309: 319-330.

Danishefsky et al., "Development of Globo-H Cancer Vaccine", *Acc. Chem Res.*, (2015), 48(3): 643-652.

Demian et al., "Direct targeted glycation of the free sulfhydryl group of cysteine residue (Cys-34) of BSA. Mapping of the glycation sites of the anti-tumor Thomsen-Friedenreich neoneoglycoconjugate vaccine prepared by Michael addition reaction," *J. Mass Spectrom.*, (2014), 49: 1223-1233.

Dondoni et al., "A new ligation strategy for peptide and protein glycosylation: Photoinduced thiol-ene coupling", *Chem. Eur. J.*, (2009), 15: 11444-11449.

Dondoni et al., "Recent applications in thiol-ene coupling as a click process for glycoconjugation", *Chem. Soc. Rev.*, (2012), 41: 573-586.

Feng et al., "Chemo-enzymatic synthesis of fluorinated 2-N-acetamidosugar nucleotides using UDP-GlcNAc pyrophosphorylase", *Org. Biomol. Chem.* (2004), 2: 1617-1623.

Grant et al., "Analysis of the SARS-CoV-2 Spike Protein Glycan Shield: Implications for Immune Recognition", Preprint. bioRxiv. 2020; 2020.04.07.030445. Published 2020 May 1. doi: 10.1101/2020.04.07.030445

Heimburg et al., "Inhibition of spontaneous breast cancer metastasis by anti-Thomsen-Friedenreich antigen monoclonal antibody JAA-F11.", *Neoplasia* (2006), 8(11): 939-48.

Jeyaprakash et al., "Crystal structure of the jacalin-T-antigen complex and a comparative study of lectin-T-antigen complexes". J Mol Biol. 2002; 321(4):637-645. doi: 10.1016/s0022-2836(02)00674-5

Knapp et al., "Synthesis of α-GalNAc Thioconjugates from an α-GalNAc Mercaptan", *J. Org. Chem.* (2002), 67: 2995-2999.

Li et al., "The Thomsen-Friedenreich Antigen-Binding Lectin Jacalin Interacts with Desmoglein-1 and Abrogates the Pathogenicity of Pemphigus *Foliaceus* Autoantibodies In Vivo", *Journal of Investigative Dermatology* (2010), 130 (12): 2773-2780.

Papadopoulos, "Diazo transfer and click chemistry in the solid phase syntheses of lysine-based glycodendrimers as antagonists against *Escherichia coli* FimH." *Molecular Pharmaceutics* (2012), 9(3): 394-403.

Ress et al., "Synthesis of Double C-Glycoside Analogue of sTn", Journal of Organic Chemistry, (2005), 70(20): 8197-200.

Rittenhouse-Diakun et al., "Development and characterization of monoclonal antibody to T-antigen: (gal beta1-3GalNAc-alpha-O)", *Hybridoma*, (1998), 17: 165-173.

Sanda et al., "N and O glycosylation of the SARS-CoV-2 spike protein", bioRxiv 2020.07.05.187344; doi: https://doi.org/10.1101/2020.07.05.187344.

Sankaranarayanan et al., "A novel mode of carbohydrate recognition in jacalin, a Moraceae plant lectin with a β-prism fold", *Nat Struct Mol Biol*, (1996), 3: 596-603.

Shajahan et al., "Deducing the N- and O-glycosylation profile of the spike protein of novel coronavirus SARS-CoV-2", Glycobiology, (2020), 1-8.

Tati et al., "Humanization of JAA-F11, a Highly Specific Anti-Thomsen-Friedenreich Pancarcinoma Antibody and InVitro Efficacy Analysis", *Neoplasia*, (2017), 19(9): 716-733.

Thompson et al., "Linear synthesis and immunological properties of a fully synthetic vaccine candidate containing a sialylated MUC1 glycopeptide", *Chem. Commun.*, (2015), 51: 10214-10217.

Varki et al., "Symbol Nomenclature for Graphical Representations of Glycans", *Glycobiology*, (2015), 25(12): 1323-4.

Watanabe et al., "Site-specific glycan analysis of the SARS-CoV-2 spike", *Science* (2020), Published online 2020 May 4. doi: 10.1126/science.abb9983.

Wu et al., "Synthesis and Immunological Evaluation of Disaccharide Bearing MUC-1 Glycopeptide Conjugates with Virus-like Particles", *ACS Chemical Biology*, (2019), 14: 2176-2184.

Yang et al., "Enhancement of the Immunogenicity of Synthetic Carbohydrate Vaccines by Chemical Modifications of STn Antigen", ACS Chem. Biol., (2011), 6: 252-259.

The invention claimed is:

1. A process for triggering the production of anti-SARS-CoV-2 antibodies in a subject, the process comprising: providing an immunogenic glycoconjugate comprising one or more carbohydrate antigens conjugated to a carrier protein or peptide, wherein the one or more carbohydrate antigens comprise or consist of unsialylated Thomsen-Friedenreich (TF) antigen, sialylated TF antigen, unsialylated Tn antigen, sialylated Tn antigen, or any combination thereof, and administering the glycoconjugate to the subject with a suitable adjuvant such that antibodies are produced that bind to the one or more carbohydrate antigens present on glycosylated spike (S) protein expressed on SARS-CoV-2 virions.

2. The process of claim 1, wherein the one or more carbohydrate antigens comprise unsialylated Tn antigen and/or unsialylated TF antigen.

3. The process of claim 1, wherein the one or more carbohydrate antigens are conjugated to the carrier protein or peptide under non-denaturing conditions such that the carrier protein or peptide in the glycoconjugate has a native or non-denatured conformation.

4. The process of claim 1, wherein the one or more carbohydrate antigens are conjugated to the carrier protein or peptide at one or more amine groups on the carrier protein or peptide.

5. The process of claim 4, wherein at least some of the one or more amine groups are epsilon amino groups of lysine residues comprised in the carrier protein or peptide.

6. The process of claim 4, wherein the glycoconjugate has the structure:

[Structure: CA—X—(CH₂)ₘ—S—(CH₂)—Y—(  )ₒ—Z—NH—CP]ₚ wherein:
- CA is the carbohydrate antigen;
- CP-NH is the carrier protein or peptide having one or more amine groups;
- X is O, S, NR$_1$, or CH$_2$;
- R$_1$ is H, COH (formamide), COMe, or COEt;
- m is 1, 2, 3, 4, or 5;
- Y is —(CH$_2$)$_n$— or —(OCH$_2$CH$_2$O)$_n$— and n is 0, 1, 2, 3, 4, or 5;
- o is 0, 1, 2, 3, 4, or 5; or o is 0 and Z is —CO— and Y is —(OCH$_2$CH$_2$O)$_n$—; or o is 0 and Z is —SO$_2$— and Y is —(OCH$_2$CH$_2$O)$_n$—;
- Z is —CO—, —NR$_2$SO$_2$—, —OCO—, —NR$_2$CO—, or —NR$_2$CS—;
- R$_2$ is H, Me, or Et; and
- p is an integer corresponding to the total number of carbohydrate antigens conjugated to the carrier protein or peptide at said one or more amine groups.

7. The process of claim 6, wherein the glycoconjugate has the structure:

[Structure: CA—O—(CH₂)₃—S—(CH₂)₂—C(=O)—NH—CP]ₚ

8. The process of claim 1, wherein the one or more carbohydrate antigens are conjugated to the carrier protein or peptide at one or more thiol groups on the carrier protein or peptide.

9. The process of claim 8, wherein at least some of the one or more thiol groups are found on cysteine residues comprised in the carrier protein or peptide.

10. The process of claim 1, wherein the carrier protein or peptide is, is from, or comprises: Tetanus Toxoid (TT), Diphtheria Toxoid (DT), cross-reacting material 197 (CRM197), Meningococcal Outer Membrane Protein Complex (OMPC), *H. influenzae* Protein D (HiD), a cytokine, an immunogenic peptide, Tetanus Toxin 831-844 (SEQ ID NO: 1 or 2), albumin, keyhole limpet hemocyanin (KLH), or an immunogenic fragment thereof.

11. The process of claim 1, wherein the carrier protein or peptide is, is from, or comprises TT or CRM197, or an immunogenic fragment thereof.

12. The process of claim 1, wherein the one or more carbohydrate antigens are covalently conjugated to positions 4 and/or 6 of the peptide of SEQ ID NO: 3, or to a variant of the peptide of SEQ ID NO: 3 comprising a cysteine or lysine at positions 4 and/or 6.

13. The process of claim 1, wherein the carrier protein or peptide comprises an immunogenic fragment of the SARS-CoV-2 S protein sequence of SEQ ID NO: 4, the fragment comprising one or more carbohydrate antigens conjugated to position 323, 325, and/or 678 of SEQ ID NO: 4.

14. The process of claim 1, wherein the carrier protein or peptide comprises an immunogenic fragment of a variant of the SARS-CoV-2 S protein sequence of SEQ ID NO: 4 having a lysine or cysteine at positions 323, 325, and/or 678, the fragment comprising one or more carbohydrate antigens conjugated to the lysine or cysteine residues at position 323, 325, and/or 678 of SEQ ID NO: 4.

15. A SARS-CoV-2 vaccine comprising the glycoconjugate as defined in claim 1, and a pharmaceutically acceptable excipient and/or an adjuvant.

16. A SARS-CoV-2 vaccine comprising the glycoconjugate as defined in claim 2, and a pharmaceutically acceptable excipient and/or an adjuvant.

17. A SARS-CoV-2 vaccine comprising the glycoconjugate as defined in claim 6, and a pharmaceutically acceptable excipient and/or an adjuvant.

18. A SARS-CoV-2 vaccine comprising the glycoconjugate as defined in claim 7, and a pharmaceutically acceptable excipient and/or an adjuvant.

19. A method of treating or reducing the risk of SARS-CoV-2 viral infection in a subject, the method comprising administering to the subject one or more ligands having binding specificity for an O-linked glycan expressed on the SARS-CoV-2 S protein, wherein the O-linked glycan is sialylated TF antigen, unsialylated TF antigen, sialylated Tn antigen, or unsialylated Tn antigen, and wherein the ligand is an antibody, an antibody fragment, or a lectin.

20. An immune complex comprising a SARS-CoV-2 S protein or fragment thereof, expressing an O-linked glycan bound to a ligand having binding specificity for said O-linked glycan, wherein the O-linked glycan is sialylated TF antigen, unsialylated TF antigen, sialylated Tn antigen, or unsialylated Tn antigen, and wherein the ligand is an antibody, an antibody fragment, or a lectin.

* * * * *

UNITED STATES PATENT AND TRADEMARK OFFICE
CERTIFICATE OF CORRECTION

PATENT NO. : 10,973,910 B1  
APPLICATION NO. : 17/025978  
DATED : April 13, 2021  
INVENTOR(S) : Tze Chieh Shiao et al.

It is certified that error appears in the above-identified patent and that said Letters Patent is hereby corrected as shown below:

In the Specification

In Column 10, Line 43, please change "thio-1 inker" to ---thio-linker---;

In Column 16, Line 6, please change "thio-1 inker" to ---thio-linker---;

In Column 17, Line 31, please change "Fieimburg" to ---Heimburg---;

In Column 17, Line 43, please change "thio-1 inker" to ---thio-linker---;

In Column 17, Line 52, please change "thio-1 inker" to ---thio-linker---;

In Column 25, Claim 18, Line 61, please change "thio-1 inker" to ---thio-linker---;

In Column 34, Line 52, please change "(8)" to ---δ---;

In Column 34, Line 52, please change "(7)" to ---*J*---;

In Column 42, Line 50, please change "Q" to ---O---;

In Column 43, Line 19, please change "5" to ---δ---;

In Column 49, Line 45, please change "FIG. 25 21" to ---FIG. 21---;

In Column 50, Line 8, please change "IgG-FIRP" to ---IgG-HRP---; and

In Column 50, Line 8, please change "IgM-FIRP" to ---IgM-HRP---.

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*